United States Patent
Liu et al.

(10) Patent No.: US 7,208,306 B2
(45) Date of Patent: Apr. 24, 2007

(54) COMPOSITIONS EMPLOYING A NOVEL HUMAN PROTEIN PHOSPHATASE

(75) Inventors: Wei Liu, Sudbury, MA (US); Leeying Wu, Lexington, MA (US); Roger Ford, Chalsea, MA (US); Xiaobing Be, Medford, MA (US)

(73) Assignee: Wyeth, Madison, NJ (US)

( * ) Notice: Subject to any disclaimer, the term of this patent is extended or adjusted under 35 U.S.C. 154(b) by 355 days.

(21) Appl. No.: 10/691,529

(22) Filed: Oct. 24, 2003

(65) Prior Publication Data

US 2004/0091926 A1   May 13, 2004

Related U.S. Application Data

(60) Provisional application No. 60/420,757, filed on Oct. 24, 2002.

(51) Int. Cl.
*C12N 9/16* (2006.01)
*C12N 15/00* (2006.01)
*C12N 5/00* (2006.01)
*C12Q 1/68* (2006.01)
*C12P 21/06* (2006.01)
*C07H 21/04* (2006.01)

(52) U.S. Cl. .................. 435/196; 435/6; 435/69.1; 435/320.1; 435/325; 536/23.2

(58) Field of Classification Search ........... 536/23.1, 536/23.2; 435/320.1, 183, 6, 69.1, 325; 424/94.1
See application file for complete search history.

(56) References Cited

U.S. PATENT DOCUMENTS

| | | | |
|---|---|---|---|
| 4,489,710 A | 12/1984 | Spitler | |
| 4,522,811 A | 6/1985 | Eppstein et al. | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 4,751,180 A | 6/1988 | Cousens et al. | |
| 4,935,233 A | 6/1990 | Bell et al. | |
| 5,459,039 A | 10/1995 | Modrich et al. | |
| 5,498,531 A | 3/1996 | Jarrell | |
| 5,919,619 A | 7/1999 | Tullis | |
| 6,506,559 B1 | 1/2003 | Fire et al. | |
| 2004/0038881 A1 | 2/2004 | Bandman et al. | |
| 2005/0196754 A1* | 9/2005 | Drmanac et al. ............ | 435/6 |

FOREIGN PATENT DOCUMENTS

| WO | WO 89/10134 | 11/1989 |
|---|---|---|
| WO | WO 97/07668 | 3/1997 |
| WO | WO 97/07669 | 3/1997 |
| WO | WO 99/14346 | 3/1999 |
| WO | WO 99/27132 | 6/1999 |
| WO | WO 00/44895 | 8/2000 |
| WO | WO 00/63364 | 10/2000 |
| WO | WO 00/73469 A2 | 12/2000 |
| WO | WO 01/29058 | 4/2001 |
| WO | WO 01/36646 | 5/2001 |
| WO | WO 01/66594 A2 | 9/2001 |
| WO | WO 01/68836 | 9/2001 |
| WO | WO 01/70949 | 9/2001 |
| WO | WO 01/75067 A | 10/2001 |
| WO | WO 01/75164 | 10/2001 |
| WO | WO 01/92513 | 12/2001 |
| WO | WO 02/08399 | 1/2002 |
| WO | WO 02/18557 A2 | 3/2002 |
| WO | WO 02/24924 | 3/2002 |
| WO | WO 02/24924 A | 3/2002 |
| WO | WO 02/46384 A2 | 6/2002 |
| WO | WO 02/081731 A2 | 10/2002 |
| WO | WO 03/050084 A2 | 6/2003 |

OTHER PUBLICATIONS

Seffernick et al., Melamine deaminase and atrazine chlorohydrolase: 98 percent identical but functionally different. J. Bacteriol. 283(8); 2405-2410, 2001.*

Altschul et al.; "*Gapped Blast and PSI-Blast: a New Generation of Protein Database Search Programs*", Nucleic Acids Research, 1997, pp. 3389-3402, vol. 25, No. 17, Oxford University Press.

Berger P. et al.; "*Loss of Phosphatase Activity in Myotubularin-Related Protein 2 is Associated With Charcot-Marie Tooth Disease Type 4B1*", Human Molecular Genetics, 2002, pp. 1569-1579, vol. 11, No. 13, Oxford University Press.

Boe R. et al.; "*The Protein Phosphatase Inhibitor Okadaic Acid Induces Morphological Changes Typical of Apoptosis in Mammalian Cells*", Experimental Cell Research 195, 1991, pp. 237-246, Academic Press, Inc.

Bottini N. et al.; "*Low-Molecular-Weight Protein Tyrosine Phosphatase and Human Disease: in Search of Biochemical Mechanisms*", Archivum Immunologiae et Therapiae Experimentalis, 2002 pp. 95-104, vol. 50.

Brown-Shimer et al.; "*Effect of Protein Tyrosine Phosphatase 1b Expression on Transformation by the Human neu Oncogene*", Cancer Research, 52, 1992, pp. 478-48.

(Continued)

*Primary Examiner*—Rebecca E. Prouty
*Assistant Examiner*—Ganapathirama Raghu
(74) *Attorney, Agent, or Firm*—Kirkpatrick & Lockhart Preston Gates Ellis LLP

(57) ABSTRACT

This invention provides compositions, organisms and methodologies employing a novel human gene encoding a protein that has sequence homology to a consensus sequence of calcineurin-like phosphoesterase family are disclosed. The novel protein is encoded by a human gene comprising 4 exons. The human gene is localized in the 10p15 locus of human chromosome 10. The sequence similarities between the novel human protein and the consensus sequence of calcineurin-like phosphoesterases indicate that the novel human protein may function as a calcineurin-like protein phosphatase.

1 Claim, 2 Drawing Sheets

OTHER PUBLICATIONS

Chen et al.; "The Myotonic Dystrophy Kinase-Related Cdc42-Binding Kinase is Involved in the Regulation of Neurite Outgrowth in PC12 Cells", The Journal of Biological Chemistry 1999, pp. 19901-19905, vol. 274, No. 28, The American Society for Biochemistry and Molecular Biology, Inc.

Delagrave et al.; "Recursive Ensemble Mutagenesis", Protein Engineering, 1993, pp. 327-331, Vol. 6 No. 3, Oxford University Press.

Dong et al.; "Cdc42 Antagonizes Inductive Action of cAMP on Cell Shape, Via Effects of the Myotonic Dystropht Kinase-Related Cdc42-Binding Kinase (MRCK) on Myosin Light Chain Phosphorylation", European Journal of Cell Biology Apr. 2002, pp. 231-242, vol. 81.

Engelman et al.; "Identifying Nonpolar Transbilayer Helices in Amino Acid Sequences of Membrane Proteins", Ann. Rev. Biophys. Chem. 1986, pp. 321-353, vol. 15, Annual Reviews Inc.

Florea et al.; "A Computer Program for Aligning a cDNA Sequence with a Genomic DNA Sequence", Genome Research 1998, pp. 967-974, vol. 8, Cold Spring Harbor Laboratory Press.

Gossen et al.; "Transcriptional Activation by Tetracyclines in Mammalian Cells", Science Jun. 23, 1995, pp. 1766-1769, vol. 268.

Guatelli et al.; "Isothermal, In Vitro Amplification of Nucleic Acids by a Multienzyme Reaction Modeled After Retroviral Replication", Proc. Natl. Acad. Sci. USA, Mar. 1990, pp. 1874-1878, vol. 87.

Haseloff et al.; "Simple RNA Ezymes With New and Highly Specific Endoribonuclease Activities", Nature, Aug. 18, 1988, pp. 585-591, vol. 334.

Hyrup et al.; "Peptide Nucleic Acids (PNA): Synthesis, Properties and Potential Applications", Bioorganic & Medicinal Chemistry, 1996, pp. 5-23, vol. 4, No. 1, Elsevier Science Ltd., Great Britain.

Ishida et al.; "Treatment of Myeloid Leukemic Cells With the Phosphatase Inhibitor Okadaic Acid Induces Cell Cycle Arrest at Either G1/S or G2/M Depending on Dose", Journal of Cellular Physiology, 1992, pp. 484-492.

Janssens et al.; "Protein Phosphatase 2A: a Highly Regulated Family of Serine/Threonine Phosphatases Implicated in Cell Growth and Signaliing", Biochem, J., 353, 2001, pp. 417-443.

Kedra et al.; "The Germinal Center Kinase Gene and a Novel CDC25-Like Gene are Located in the Vicinity of the PYGM Gene on 11q13", Hum. Genet., 1997, pp. 611-619, vol. 100.

Keen et al.; Rapid Detection of Single Base Mismatches as Heteroduplexes on Hydrolink Gels, Trends in Genetics, 1997, p. 5, vol. 7.

Kwoh et al.; "Transcription-Based Amplification System and Detection of Amplified Human Immunodeficiency Virus Type 1 With a Bead-Based Sandwich Hybridization Format", Proc. Natl. Acad. Sci. USA, Feb. 1989, pp. 1173-1177, vol. 86.

Lam et al.; "Characterization of a Monoclonal Antibody Panel Shows That the Myotonic Dystrophy Protein Kinase, DMPK, is Expressed Almost Exclusively in Muscle and Heart", Human Molecular Genetics, 2000, pp. 2167-2173, vol. 9, No. 4, Oxford University Press.

Lee et a.; "Expression of Small Interfering RNAs Targeted Against HIV-1 rev Transcripts in Human Cells", Nature Biotechnology, May 2002, pp. 500505, vol. 19.

Leung et al.; "Myotonic Dystrophy Kinase-Related Cdc42-Binding Kinase Acts as a Cdc42 Effector in Promoting Cytoskeletal Reorganization", Molecular and Cellular Biology, Jan. 1998, pp. 130-140, vol. 18, No. 1, American Society for Microbiology.

Lizardi et al.; "Exponential Amplification of Recombinant-RNA Hybridization Probes", Biotechnology, Oct. 1988, pp. 1197-1202. vol. 6.

Maratea et al.; "Deletion and Fusion Analysis of the Phage ⱷx174 Lysis Gene E", 1985, pp. 39-46, vol. 40, Elsevier Science Publishers.

Meyers et al.; "Optimal Alignments in Linear Space", Cabios, 1988, pp. 11-17, vol. 4, No. 1, Press Limited, Oxford England.

Murphy et al.; "Genetic Construction, Expression, and Melanoma-Selective Cytotoxicity of a Diphtheria Toxin-Related α-Melanoma-Stimulating Hormone Fusion Protein", Proc. Natl. Aca. Sci. USA, Nov. 1986, pp. 8258-8262, VO. 83.

Needleman et al.; "A General Method Applicable to the Search for Similarities in the Amino Acid Sequence of Tow Proteins", J. Mol. Bio., 1970, pp. 443-453, vol. 48.

No et al.; "Ecdysone-Inducible Gene Expression in Mammalian Cells and Transgenic Mice", Proc. Natl. Acad. Sci. USA, Apr. 1996, pp. 3346-3351, vol. 93.

Nomura et al.; "Enhancement by Cyclosporin a of Taxol-Induced Apoptosis of Human Urinary Bladder Cancer Cells", Urol Res, 2002, pp. 102-111, vol. 30.

O'Gorman et al.; "Recombinase-Mediated Gene Activation and Site-Specific Integration in Mammalian Cells", Science, Mar. 1991, pp. 1351-1355.

Rosenbaum et al.; "Temperature-Gradient Gel Electrophoresis", Biophysical Chemistry, 1987, pp. 235-246, vol. 26.

Saiki et al.; "Genetic Analysis of Amplified DNA with Immobilized Sequence-Specific Oligonucleotide Probes", Proc. Natl. Acad. Sci. USA, Aug. 1989, pp. 6230-6234, vol. 86.

Straub et al.; "Genome-Wide Scans of Three Independent Sets of 90 Irish Multiplex Schizophrenia Families and Follow-Up of Selected Regions in all Families Provides Evidence for Multiple Susceptibility Genes", Mol. Psychiatry, 2002, pp. 542-559, vol. 7, No. 6.

Sui et al.; "A DNA Vector-Based RNAi Technology to Suppress Gene Expression in Mammalian Cells", Proc. Natl. Acad. Sci., Apr. 16, 2002, pp. 5515-5520, vol. 99, No. 8.

Tan et al.; "Phosphorylation of a Novel Myosin Binding SubUnit of Protein Phosphatase 1 Reveals a Conserved Mechanism in the Regulation of Actin Cytoskeleton", The Journal of Biological Chemistry, 2001, pp. 21209-21216, vol. 276, No. 24.

Tan et al.; "Intermolecular and Intramolecular Interactions Regulate Catalytic Activity of Myotonic Dystrophy Kinase-Related Cdc42-Binding Kinase α", Molecular and Cellular Biology, Apr. 2001, pp. 2767-2778, vol. 21, No. 8.

Wang et al.; "Ligand-Inducible and Liver-Specific Target Gene Expression in Transgenic Mice", Nature Biotechnology, Mar. 1997, pp. 239-243, vol. 15.

Wary et al.; "A Homozygous Deletion Within the Carbonic Anhydrase-Like Domain of the Ptprg Gene in Murine L-Cells", Cancer Research, Apr. 1, 1993, pp. 478-482, vol. 53.

Wilmut et al.; "Viable Offspring Derived From Fetal and Adult Mammalian Cells", Letters to Nature, Feb. 1997, pp. 810-813, vol. 385.

Ye et al.; "Regulated Delivery of Therapeutic Proteins After In Vivo Somatic Cell Gene Transfer", Science, Jan. 1999, pp. 88-91, vol. 283.

Zhao et a.; "Reversible Modification of Tissue-Type Plasminogen Activator by Methyphosphonate Esters", Bioorganic & Medicinal Chemistry, 1996, pp. 523-529, vol. 4.

Zy; "Protein Tyrosine Phosphatases: Structure and Function, Substrate Specificity, and Inhibitor Developmen", Annu Rev Pharmacol Toxicol, 2002, pp. 209-234, vol. 42.

Hayashi, K. et al., "Activity and substrate specificity of the murine STK2 Serine/Threonine kinase that is structurally related to the mitotic regulator protein NIMA of Aspergillus nidulans," Biochem. Biophys. Res. Commun., 264(2):449-56 (1999).

Database GenEmbl, on STN, AN AF021935, Leung, T. et al., "Myotonic Dystrophy Kinase-Related Cdc42-Binding Kinase Acts as a Cdc42 Effector in Promoting Cytoskeletal Reorganization, " Sequence Comparison, pp. 18-21.

Collins, F.S., "Generation and initial analysis of more than 15,000 full-length human and mouse cDNA sequences," Proc. Natl. Acad. Sci. USA, 99(26):16899-16903 (2002).

Database GenCore on STN, AN AAD34299, Bandman, O. et al., Database N Geneseq Jan. 29, 2004 (WO 02/18557-A2), Mar. 7, 2002, Sequence Comparison, pp. 1-4.

Aravind, et al., "Phosphoesterase Domains Associated with DNA Polymerases of Diverse Origins," Nucleic Acids Research, vol. 26, No. 16, pp. 3746-3754 (1998).

Engelman, et al., "Identifying Nonpolar Transbilayer Helices in Amino Acid Sequences of Membrane Protein," Ann. Rev. Biophys. Biophys. Chem., 15: 321-53 (1986).

Myers, et al., "Detection of Single Base Substitutions by Ribonuclease Cleavage at Mismatches in RNA: DNA Duplexes," Science, vol. 230, pp. 2-6.

Needleman, et al., "A General Method Applicable to the Search for Similarities in the Amino Acid Sequence of Two Proteins," J. Mol. Biol. 48: 443-453 (1970).

Wary, et al., A Homozygous Deletion Within the Carbonic Anhydrase-Like Domain of the *PTPRG* Gene in Murine L-Cells[1], Cancer Research, 53, 1498-1502 (1993).

PCT International Search Report, dated Jul. 6, 2004.

* cited by examiner

```
Query:   47   DLALGLDWLTKVSFDPACDLLISVGDLVDRGAENVECLELITMPWFRA------VRGNHE   100
Sbjct:   15   DLDELLLLLLELLGEPKPDLVLFLGDLVDRGPPSLEVLLLLFALKLKLPGPVYLVRGNHD    74

Query:  101   QMMIDG-------LSEYGNVNHWLENGGVWFFSLDYEKEVLAKALVHKSASLPFVIELVT   153
Sbjct:   75   FDSGNSVLGFLLECAGFPYVLANVGDLVEIVGLSSLYGKGGGNVWELFLELFDLLLLAAL   134

Query:  154   AERKIVICHADYPHNEYAFDKPVPKDMVIWNRERVSDAQDGIVSPIAGADLFIFGHTP    211
Sbjct:  135   VDGKILLVHGPLSPDLDSGDDIVLFGPEVLEELLKKN---------GVDLVLRGHTH    182
```

FIG. 1

COMPOSITIONS EMPLOYING A NOVEL HUMAN PROTEIN PHOSPHATASE

The present invention incorporates by reference U.S. Provisional Application Ser. No. 60/420,757, filed Oct. 24, 2002 and entitled "Compositions, Organisms and Methodologies Employing a Novel Human Phosphatase."

FIELD OF THE INVENTION

The present invention relates to compositions, organisms and methodologies employing a novel human protein phosphatase, calcineurin-like protein phosphatase 1 (CLPP1), which has 91% sequence homology to the consensus sequence of the calcineurin-like phosphoesterase family. This invention can be used for diagnosing, prognosing, and treating phosphatase-related diseases and, in particular, diseases associated with aberrant expression of CLPP1.

BACKGROUND OF THE INVENTION

Protein phosphorylation/dephosphorylation plays a central role in the regulation of a variety of cell functions, such as cell proliferation, differentiation, and signaling processes. Uncontrolled signaling has been implicated in a variety of disease conditions including inflammation, cancer, arteriosclerosis, and psoriasis. It is estimated that more than 1,000 of the 10,000 proteins active in a typical mammalian cell are phosphorylated. As is well-known in the art, high energy phosphate, which drives activation, is generally transferred from adenosine triphosphate molecules (ATP) to a particular protein by protein kinases and removed from that protein by protein phosphatases.

The presence or absence of a phosphate moiety modulates protein function in multiple ways. A common mechanism involves changes in the catalytic properties (Vmax and Km) of an enzyme, leading to its activation or inactivation.

A second widely recognized mechanism involves promoting protein-protein interactions. An example of this is the tyrosine autophosphorylation of the ligand-activated EGF receptor tyrosine phosphatase. This event triggers the high-affinity binding to the phosphotyrosine residue on the receptor's C-terminal intracellular domain to the SH2 motif of an adaptor molecule Grb2. Grb2, in turn, binds through its SH3 motif to a second adaptor molecule, such as SHC. The formation of this ternary complex activates the signaling events that are responsible for the biological effects of EGF. Serine and threonine phosphorylation events also have been recently recognized to exert their biological function through protein-protein interaction events that are mediated by the high-affinity binding of phosphoserine and phosphothreonine to WW motifs present in a large variety of proteins.

A third important outcome of protein phosphorylation is changes in the subcellular localization of the substrate. As an example, nuclear import and export events in a large diversity of proteins are regulated by protein phosphorylation.

Reversible protein phosphorylation is an essential regulatory mechanism in many cellular processes. While the post-translational modification alters the properties of key regulatory proteins involved in various biochemical pathways, protein kinases and phosphatases themselves are subject to control through the action of extracellular signals such as hormones and growth factors. Although much attention has been paid to the regulation of protein kinases, it is now apparent that protein phosphatases are also highly regulated enzymes that play an equally important role in the control of protein phosphorylation.

Protein phosphatases may be roughly divided into three families based on their substrate: the serine/threonine (S/T) phosphatases, the tyrosine phosphatases, (PTP), and dual specificity phosphatases.

Serine/threonine (S/T) protein phosphatases (PPases) catalyse the dephosphorylation of phosphoserine and phosphothreonine residues. Their action is opposed to that of a large number of serine/threonine protein kinases. In mammalian tissues four different types of PPase have been identified and are known as PP1, PP2A, PP2B and PP2C. Except for PP2C, these enzymes are evolutionary related. The catalytic regions of the proteins are well conserved and have a slow mutation rate, suggesting that major changes in these regions are highly detrimental.

Protein tyrosine phosphatases (PTPs) catalyse the dephosphorylation of phosphotyrosine residues. PTPs represent a large family of enzymes that play a very important role in cellular signaling within and between cells. PTPs work antagonistically with protein tyrosine kinases (PTKs) to regulate signal transduction in a cell.

A few protein phosphatases have dual specificity and dephosphorylate serine/threonine and tyrosine residues. This family now includes major regulators of growth cycle such as p80cdc25, as well as phosphatases that regulate the mitogen-activated protein kinase pathway.

SUMMARY OF THE INVENTION

The present invention discloses compositions, organisms and methodologies employing a new human gene that encodes a protein sharing sequence homology with the calcineurin-like phosphoesterase family. The gene is localized in locus 10p15 of human chromosome 10. This new gene is hereinafter referred to as human calcineurin-like protein phosphatase 1 (CLPP1) gene, and its encoded protein(s) is referred to as CLPP1 or CLPP1 phosphatase.

The amino acid residues 47–211 of CLPP1 show 91.3% sequence alignment with the consensus sequences of the calcineurin-like phosphoesterase family. This family includes a diverse range of phosphoesterases, including protein phosphoserine phosphatases, nucleotidases, sphingomyelin phosphodiesterases and 2'–3' cAMP phosphodiesterases as well as nucleases such as bacterial SbcD or yeast MRE11. The utility of calcineurin-like phosphoesterase family members are known in the art. The unique peptide sequence of CLPP1, and nucleic acid sequences that encode the peptides, can be used as models for the development of human therapeutic targets, aid in the identification of therapeutic proteins, and serve as targets for the development of human therapeutic agents that modulate phosphatase activity in cells and tissues that express the phosphatase.

In one aspect, the invention provides isolated polynucleotides comprising a nucleotide sequence encoding CLPP1 or a variant of CLPP1.

In another aspect, the invention provides isolated polypeptides comprising the amino acid sequence of CLPP1 or a variant of CLPP1.

In yet another aspect, the invention provides agents that modulate expression level of CLPP1 gene or an activity of CLPP1.

The invention also provides methods for (a) detecting polynucleotides comprising a nucleotide sequence encoding CLPP1 or a variant of CLPP1 and (b) detecting polypeptides comprising an amino acid sequence of CLPP1 or a variant of CLPP1 in a biological sample.

The invention further provides methods for screening agents that modulate expression level of CLPP1 gene or an activity of CLPP1. The invention further provides cell lines harboring the CLPP1 gene, animals transgenic for CLPP1 gene, and animals with interrupted CLPP1 gene (CLPP1 knockout animals). These cell lines and animals can be used to study the functions of CLPP1.

In still another aspect, the invention provides polynucleotides capable of inhibiting CLPP1 gene expression by RNA interference.

The invention further provides methods of inhibiting CLPP1 gene expression by introducing siRNA's or other RNAi sequences into target cells.

The preferred embodiments of the inventions are described below in the Detailed Description of the Invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

It is further intended that the inventions not be limited only to the specific structure, material or acts that are described in the preferred embodiments, but include any and all structures, materials or methods that perform the claimed function, along with any and all known or later-developed equivalent structures, materials or methods for performing the claimed function.

Further examples exist throughout the disclosure, and it is not applicant's intention to exclude from the scope of his invention the use of structures, materials, or methods that are not expressly identified in the specification, but nonetheless are capable of performing a claimed function.

BRIEF DESCRIPTION OF THE DRAWINGS

The inventions of this application are better understood in conjunction with the following drawings, in which:

FIG. 1 compares amino acid residues 47 to 211 of CLPP1 (SEQ ID NO:2) to the consensus sequences of the calcineurin-like phosphoesterase family (SEQ ID NO:304).

DETAILED DESCRIPTION OF THE INVENTION

Figure 2:
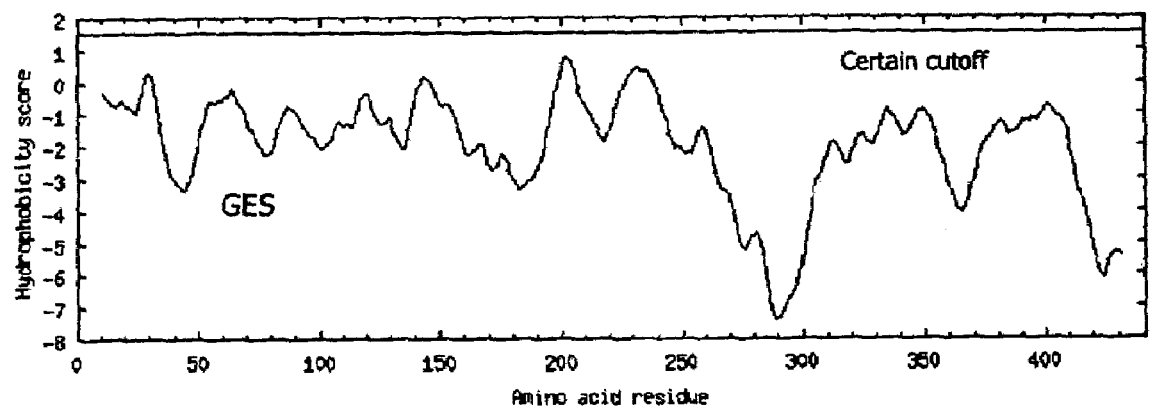
FIG. 2 shows the hydrophobicity profile of CLPP1.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The present invention is based on the sequence information obtained from a newly-developed genomic prediction pipeline. Briefly, the X-ray crystal structures of the catalytic domains of protein phosphatases were collected and aligned together according to their structural identity/similarities. The alignment was converted into a "scoring matrix" which carried the structural profile of the phosphatase catalytic domains. This scoring matrix was then used to search the Celera Human Genome database and pull out sequences that have phosphatase catalytic domains.

Based on this analysis, the present invention provides the amino acid sequence of a human peptide containing a phosphatase domain that is highly homologous to the consensus sequences of the calcineurin-like phosphoserine family, cDNA sequences and genomic sequences that encode the phosphatase peptide, and information about the closest art known protein/peptide/domain that has structural or sequence homology to the phosphatase of the present invention.

The peptide of the present invention may be used for the development of commercially important products and services. Various aspects of the invention are described in detail in the following subsections. It should of course be understood that the use of subsections is not meant to limit the invention. Rather, each subsection applies to any aspect of the invention, as is appropriate.

Definitions and Terms

To facilitate the understanding of the present invention, a number of terms and phrases are defined below:

As used herein, a polynucleotide or a polypeptide is "isolated" if it is removed from its native environment. For instance, a polynucleotide or a polypeptide is isolated through a purification process such that the polynucleotide or polypeptide is substantially free of cellular material or free of chemical precursors. The polynucleotide/polypeptide of the present invention can be purified to homogeneity or other degrees of purity. The level of purification will be based on the intended use. As appreciated by one of ordinary skill in the art, a polynucleotide/polypeptide can perform its desired function(s) even in the presence of considerable amounts of other components or molecules.

In some uses, a polynucleotide/polypeptide that is "substantially free of cellular material" includes preparations which have less than about 30% (by weight) other polynucleotides/polypeptides including contaminating polynucleotides/polypeptides. For instance, the preparations can have less than about 20%, less than about 10%, or less than about 5% other polynucleotides/polypeptides. If a polynucleotide/polypeptide preparation is recombinantly produced, it can be substantially free of culture medium, i.e., culture medium components representing less than about 20% by weight of the polynucleotide/polypeptide preparation.

The language "substantially free of chemical precursors" includes preparations in which the polynucleotide/polypeptide is separated from chemical precursors or other chemicals that are involved in the synthesis of the polynucleotide/polypeptide. In one embodiment, the language "substantially free of chemical precursors" includes kinase preparations having less than about 30% (by weight), less than about 20% (by weight), less than about 10% (by weight), or less than about 5% (by weight) chemical precursors or other chemicals used in the synthesis.

A "polynucleotide" can include any number of nucleotides. For instance, a polynucleotide can have at least 10, 20, 25, 30, 40, 50, 100 or more nucleotides. A polynucleotide can be DNA or RNA, double-stranded or single-stranded. A polynucleotide encodes a polypeptide if the polypeptide is capable of being transcribed and/or translated from the polynucleotide. Transcriptional and/or translational regulatory sequences, such as promoter and/or enhancer(s), can be added to the polynucleotide before said transcription and/or translation occurs. Moreover, if the polynucleotide is singled-stranded, the corresponding double-stranded DNA containing the original polynucleotide and its complementary sequence can be prepared before said transcription and/or translation.

As used herein, "a variant of a polynucleotide" refers to a polynucleotide that differs from the original polynucleotide by one or more substitutions, additions, and/or deletions. For instance, a variant of a polynucleotide can have 1, 2, 5, 10, 15, 20, 25 or more nucleotide substitutions, additions or deletions. Preferably, the modification(s) is in-frame, i.e., the modified polynucleotide can be transcribed and translated to the original or intended stop codon. If the original polynucleotide encodes a polypeptide with a biological activity, the polypeptide encoded by a variant of the original polynucleotide variants substantially retains such activity. Preferably, the biological activity is reduced/enhanced by less than 50%, or more preferably, less than 20%, relative to the original activity.

A variant of a polynucleotide can be a polynucleotide that is capable of hybridizing to the original polynucleotide, or the complementary sequence thereof, under reduced stringent conditions, preferably stringent conditions, or more preferably, highly stringent conditions. Examples of conditions of different stringency are listed in Table 1. Highly stringent conditions are those that are at least as stringent as conditions A–F; stringent conditions are at least as stringent as conditions G–L; and reduced stringency conditions are at least as stringent as conditions M–R. As used in Table 1, hybridization is carried out under a given hybridization condition for about 2 hours, followed by two 15-minute washes under the corresponding washing condition(s).

TABLE 1

Stringency Conditions

| Stringency Condition | Polynucleotide Hybrid | Hybrid Length (bp)[1] | Hybridization Temperature and Buffer[H] | Wash Temp. and Buffer[H] |
|---|---|---|---|---|
| A | DNA:DNA | >50 | 65° C.; 1xSSC -or- 42° C.; 1xSSC, 50% formamide | 65° C.; 0.3xSSC |
| B | DNA:DNA | <50 | $T_B^*$; 1xSSC | $T_B^*$; 1xSSC |
| C | DNA:RNA | >50 | 67° C.; 1xSSC -or- 45° C.; 1xSSC, 50% formamide | 67° C.; 0.3xSSC |
| D | DNA:RNA | <50 | $T_D^*$; 1xSSC | $T_D^*$; 1xSSC |
| E | RNA:RNA | >50 | 70° C.; 1xSSC -or- 50° C.; 1xSSC, 50% formamide | 70° C.; 0.3xSSC |
| F | RNA:RNA | <50 | $T_F^*$; 1xSSC | $T_F^*$; 1xSSC |
| G | DNA:DNA | >50 | 65° C.; 4xSSC -or- 42° C.; 4xSSC, 50% formamide | 65° C.; 1xSSC |
| H | DNA:DNA | <50 | $T_H^*$; 4xSSC | $T_H^*$; 4xSSC |
| I | DNA:RNA | >50 | 67° C.; 4xSSC -or- 45° C.; 4xSSC, 50% formamide | 67° C.; 1xSSC |
| J | DNA:RNA | <50 | $T_J^*$; 4xSSC | $T_J^*$; 4xSSC |
| K | RNA:RNA | >50 | 70° C.; 4xSSC -or- 50° C.; 4xSSC, 50% formamide | 67° C.; 1xSSC |
| L | RNA:RNA | <50 | $T_L^*$; 2xSSC | $T_L^*$; 2xSSC |
| M | DNA:DNA | >50 | 50° C.; 4xSSC -or- 40° C.; 6xSSC, 50% formamide | 50° C.; 2xSSC |
| N | DNA:DNA | <50 | $T_N^*$; 6xSSC | $T_N^*$; 6xSSC |
| O | DNA:RNA | >50 | 55° C.; 4xSSC -or- 42° C.; 6xSSC, 50% formamide | 55° C.; 2xSSC |
| P | DNA:RNA | <50 | $T_P^*$; 6xSSC | $T_P^*$; 6xSSC |
| Q | RNA:RNA | >50 | 60° C.; 4xSSC -or- 45° C.; 6xSSC, 50% formamide | 60° C.; 2xSSC |
| R | RNA:RNA | <50 | $T_R^*$; 4xSSC | $T_R^*$; 4xSSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[H]SSPE (1xSSPE is 0.15 M NaCl, 10 mM $NaH_2PO_4$, and 1.25 mM EDTA, pH 7.4) can be substituted for SSC (1xSSC is 0.15 M NaCl and 15 mM sodium citrate) in the hybridization and wash buffers.
$T_B^*$–$T_R^*$The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.) = 2(\# \text{ of } A + T \text{ bases}) + 4(\# \text{ of } G + C \text{ bases})$. For hybrids between 18 and 49 base pairs in length, $T_m(° C.) = 81.5 + 16.6(\log_{10} Na^+) + 0.41(\% G + C) - (600/N)$, where N is the number of bases in the hybrid, and $Na^+$ is the molar concentration of sodium ions in the hybridization buffer ($Na^+$ for 1xSSC = 0.165 M).

It will be appreciated by those of ordinary skill in the art that, as a result of the degeneracy of the genetic code, there are many polynucleotide variants that encode the same polypeptide. Some of these polynucleotide variants bear minimal sequence homology to the original polynucleotide. Nonetheless, polynucleotides that vary due to differences in codon usage are specifically contemplated by the present invention.

As used herein, a "polypeptide" can include any number of amino acid residues. For instance, a polypeptide can have at least 5, 10, 15, 20, 30, 40, 50 or more amino acid residues.

As used herein, a "variant of a polypeptide" is a polypeptide that differs from the original polypeptide by one or more substitutions, deletions, and/or insertions. Preferably, these modifications do not substantially change (e.g. reduce or enhance) the original biological function of the polypeptide. For instance, a variant can reduce or enhance or maintain the biological activities of the original polypeptide. Preferably, the biological activities of the variant is reduced or enhanced by less than 50%, or more preferably, less than 20%, relative to the original polypeptide.

Similarly, the ability of a variant to react with antigen-specific antisera can be enhanced or reduced by less than 50%, preferably less than 20%, relative to the original polypeptide. These variants can be prepared and evaluated by modifying the original polypeptide sequence and then determining the reactivity of the modified polypeptide with the antigen-specific antibodies or antisera.

Preferably, a variant polypeptide contains one or more conservative substitutions. A "conservative substitution" is one in which an amino acid is substituted for another amino acid which has similar properties, such that one skilled in the art would expect that the secondary structure and hydropathic nature of the substituted polypeptide will not be substantially changed. Conservative amino acid substitutions can be made on the basis of similarity in polarity, charge, solubility, hydrophobicity, hydrophilicity and/or the amphipathic nature of the residues. Negatively charged amino acids include aspartic acid and glutamic acid, and positively charged amino acids include lysine and arginine. Amino acids having uncharged polar head groups and similar hydrophilicity values include leucine, isoleucine and valine, or glycine and alanine, or asparagine and glutamine, or serine, threonine, phenylalanine and tyrosine. Other groups of amino acids that can produce conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A polypeptide variant can also contain nonconservative changes.

Polypeptide variants can be prepared by the deletion and/or addition of amino acids that have minimal influence on the biological activity, immunogenicity, secondary structure and/or hydropathic nature of the polypeptide. Variants can be prepared, for instance by substituting, modifying, deleting or adding one or more amino acids residues in the original sequence. Polypeptide variants preferably exhibit at least about 70%, more preferably at least about 90%, and most preferably at least about 95% sequence homology to the original polypeptide.

Polypeptide variants include polypeptides that are modified from the original polypeptides either by a natural process, such as a post-translational modification, or by a chemical modification. These modifications are well known in the art. Modifications can occur anywhere in the polypeptide, including the backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides may be branched, for example, as a result of ubiquitination, and they may be cyclic, with or without branching. Cyclic, branched, and branched cyclic polypeptides can result from natural post-translational processes or be made through synthetic methods. Suitable modifications for this invention include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, the term "modulation" includes up-regulation, induction, stimulation, potentiation, inhibition, down-regulation or suppression, or relief of inhibition.

A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

As used herein, a "disease-free" human refers to a human who does not have CLPP1-related diseases. Disease-free cells, tissues or samples refer to cells, tissues or samples obtained from disease-free human(s).

A polynucleotide is "capable of hybridizing" to a gene if the polynucleotide can hybridize to at least one of the following sequences: (1) the sequence of a RNA transcript of the gene, (2) the complementary sequence of a RNA transcript of the gene, (3) the cDNA sequence of a RNA transcript of the gene, (4) the complementary sequence of the cDNA sequence of a RNA transcript of the gene, (5) a genomic sequence of the gene, and (6) the complementary sequence of a genomic sequence of the gene.

As used herein, sequence identity or percentage alignment in an alignment can be determined by the standard protein-protein or nucleotide-nucleotide BLAST programs (i.e., blastp or blastn, respectively). Sequence identity or percentage alignment can also be determined by the BLAST2 program. Suitable BLAST programs can be found at the BLAST web site maintained by the National Center of Biotechnology Information (NCBI) (National Library of Medicine, USA).

Human CLPP1 Gene and CLPP1 Phosphatase

The present invention identifies a new human gene (CLPP1 gene) that encodes a protein containing sequences highly homologous to the consensus sequence of the calcineurin-like phosphoesterase family. The nucleotide sequence encoding CLPP1 and the amino acid sequence of CLPP1 are depicted in SEQ ID NOS:1 and 2, respectively. The CLPP1 gene is localized in locus 10p15 of human chromosome 10. Specifically, the CLPP1 gene is located between genes LOC119379 and LOC159671, and overlaps with gene LOC159669.

Human chromosome loci 10p15 and the neighboring regions have been associated with multiple diseases, including but not limited to, prostate cancer, glioma, melanoma, primary open-angle glaucoma, primary endometrial carcinoma, multiple sclerosis, schizophrenia, and partial DiGeorge syndrome. It has been suggested that the distal end of the short arm of chromosome 10 harbors at least one tumor suppressor gene.

Human CLPP1 gene has 4 exons. The exons are mapped to the nucleotide sequences of human chromosome 10 in Celera genomic database (SEQ ID NO:3). The exons are also mapped to nucleotides 4200965 to 4203759 of human chromosome 10 in the Entrez Human Genome Sequence Database maintained by NCBI. Table 2 lists the location of each of these 4 exons in the genomic sequence SEQ ID NO:3. Table 2 also illustrates the corresponding location of each exon in the CLPP1-coding sequence SEQ ID NO:1.

TABLE 2

Exons in Human CLPP1 Gene

| Exon Numbers | Corresponding Sequence in SEQ ID NO: 3 | Corresponding Sequence in SEQ ID NO: 1 |
| --- | --- | --- |
| 1 | 1–55 | 1–55 |
| 2 | 789–898 | 56–165 |
| 3 | 1589–2131 | 166–708 |
| 4 | 2178–2795 | 709–1326 |

A conserved domain search using RPS-BLAST program (RPS-BLAST 2.2.3 [Apr. 24, 2002], available at the BLAST web site maintained by NCBI), showed that CLPP1 contained sequences homologous to a consensus sequence of a family of protein phosphatases.

Specifically, the amino acid residues 47 to 211 of CLPP1 are highly homologous to the consensus sequence of the calcineurin-like phosphoesterase family (pfam00149). This family includes a diverse range of phosphoesterases, including protein phosphoserine phosphatases, nucleotidases, sphingomyelin phosphodiesterases and 2'–3' cAMP phosphodiesterases as well as nucleases such as bacterial SbcD or yeast MRE11. The most conserved regions in this family center around the metal chelating residues. FIG. 1 shows that the two sequences share 91.3% alignment with a score of 51.5 bits and an E value of $6 \times 10^{-8}$. The "Query" denotes the sequence of CLPP1, and "Sbjct" refers to the sequence being compared to the CLPP1 sequence.

In addition, CLPP1 also shares partial sequence homologies to a number of ser/thr phosphatases, including but are not limited to, Bacteriophage lambda ser/thr protein phosphatase (Entrez accession number: P03772, 75% alignment to amino acid residues 55–242 of CLPP1), E. coli ser/thr protein phosphatase (Entrez accession number: NC002695, 74% alignment to amino acid residues 55–242 of CLPP1), E. coli phosphoprotein phosphatase 1 (Entrez accession number: AP002559, 47% alignment to amino acid residues 60–239 of CLPP1), and S. typhimurium protein phosphatase B (Entrez accession number: AY049951, 42% alignment to amino acid residues 43–239 of CLPP1).

FIG. 2 shows the hydrophobicity profile of CLPP1. The hydrophobicity analysis indicates that CLPP1 phosphatase is not likely a membrane or transmembrane protein.

BLAST analysis showed that CLPP1 is identical in both amino acid and nucleotide sequences to a hypothetical human protein XP_100270 (Entrez accession number: XM100270), which was predicted from NCBI contig NT024115 by automated computational analysis using gene prediction method GenomeScan.

The existence and expression of CLPP1 gene in humans are supported by various EST sequences. For instance, nucleotides 1–57 of SEQ ID NO:1 are supported by the EST sequences disclosed under NCBI EST database accession number BI829819; nucleotides 172–815 of SEQ ID NO:1 are supported by the EST sequence disclosed under NCBI DNA patent database accession numbers AAS65776, AAS65777, and AAS82423; nucleotides 763–1308 of SEQ ID NO: 1 are supported by the EST sequences disclosed under ENSEMBL database accession number ENST00000266954.

Utility of CLPP1 Gene and CLPP1 Phosphatase

As the counterpart of protein kinases, protein phosphatases are involved in the regulation of many critical biological processes. The protein phosphorylation/dephosphorylation cycle is one of the major regulatory mechanisms employed by eukaryotic cells to control cellular activities including growth and differentiation, cell-to-cell contacts, the cell cycle, and oncogenesis. For example, cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of certain residues on proteins.

Based on their substrate specificity, protein phosphatases may be roughly divided into three families: serine/threonine (S/T) phosphatases, tyrosine phosphatases, (PTPs), and dual specificity phosphatases (DSPs).

Serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP1, PP2A, PP2B, and PP2C.

PP1 is a major eukaryotic protein serine/threonine phosphatase that regulates an enormous variety of cellular functions through the interaction of its catalytic subunit (PP1c) with over fifty different established or putative regulatory subunits. PP1 dephosphorylates many of the proteins phosphorylated by cyclic AMP-dependent protein phosphatase and is therefore an important regulator of many cyclic AMP mediated, hormone responses in cells. Most of these PP1c targets interact with a small hydrophobic groove on the surface of PP1c through a short conserved binding motif, the RVxF motif, which is often preceded by further basic residues. Weaker interactions may subsequently enhance binding and modulate PP1 activity/specificity in a variety of ways. Several putative targeting subunits do not possess an RVxF motif but nevertheless interact with the same region of PP1c. In addition, several 'modulator' proteins bind to PP1 c but do not possess a domain targeting them to a specific location. Most are potent inhibitors of PP1c and possess at least two sites for interaction with PP1c, one of which is identical or similar to the RVxF motif. Regulation of PP1c in response to extracellular and intracellular signals occurs mostly through changes in the levels, conformation or phosphorylation status of targeting subunits. Understanding of the mode of action of PP1c complexes may facilitate development of drugs that target particular PP1c complexes and thereby modulate the phosphorylation state of a very limited subset of proteins.

PP2A is the main phosphatase responsible for reversing the phosphorylations of serine/threonine phosphatases. All forms of PP2A contain a catalytic subunit (PP2Ac) which forms a stable complex with the structural subunit PR65/A. The heterodimer PP2Ac-PR65/A associates with regulatory proteins, termed variable subunits, in order to form trimeric holoenzymes attributed with distinct substrate specificity and targeted to different subcellular compartments. PP2Ac activity can be modulated by reversible phosphorylation on Tyr307 and methylation on C-terminal Leu309. Studies on PP2A have shown that this enzyme may be implicated in the regulation of metabolism, transcription, RNA splicing, translation, differentiation, cell cycle, oncogenic transformation and signal transduction.

PP2B, or calcineurin (Cn), is a $Ca^{2+}$-activated phosphatase; it is involved in the regulation of such diverse cellular functions as ion channel regulation, neuronal transmission, gene transcription, muscle glycogen metabolism, and lymphocyte activation.

PP2C is a $Mg^{2+}$-dependent phosphatase which participates in a wide variety of functions including regulating cyclic AMP-activated protein-phosphatase activity, $Ca^{2+}$-dependent signal transduction, tRNA splicing, and signal transmission related to heat shock responses. PP2C is a monomeric protein with a molecular mass of about 40–45 kd. One alpha and several beta isoforms of PP2C have been identified.

Protein tyrosine phosphatases (PTPs) remove a phosphate moiety from phosphotyrosine. Their substrates include elements of signal transduction pathway such as receptors, transcription factors or ion channels, as well as structural proteins such as filaments and cellular motors. PTPs regulate cell differentiation and are also involved in malignant transformation. PTP1B, a major phosphatase of breast cancer cell lines, activates an oncogene, c-src. Regulatory networks of PTPs can be extensive and redundant, with one enzyme being able to complement others. The sequence provided by the present invention can be used to isolate a possible group of interrelated PTPs. Specific inhibitors of protein phosphatases are being developed. Especially promising are the drugs that target PTPs in hematopoietic and lymphoid tissues; such drugs can be used to treat various malignant conditions.

Dual-specificity phosphatases (DSPs) are important for regulating mitogenic signal transduction processes that occur, for example, in the cell cycle and in extracellular stimulation pathways. DSPs may be involved in regulating meiosis and may also play an important role in regulating the differentiation of testicular germ cells during spermatogenesis.

The levels of protein phosphorylation required for normal cell growth and differentiation at any time are achieved through the coordinated action of protein kinases and phosphatases. Depending on the cellular context, these two types of enzymes may either antagonize or cooperate with each other during signal transduction. An imbalance between these enzymes may impair normal cell functions leading to metabolic disorders and cellular transformation.

Protein kinases have been a major target for drug action and development. A January 2002 survey of ongoing clinical trials in the USA revealed more than 100 clinical trials involving the modulation of kinases. Trials are ongoing in a wide variety of therapeutic indications including asthma, Parkinson's, inflammation, psoriasis, rheumatoid arthritis, spinal cord injuries, muscle conditions, osteoporosis, graft versus host disease, cardiovascular disorders, autoimmune disorders, retinal detachment, stroke, epilepsy, ischemia/reperfusion, breast cancer, ovarian cancer, glioblastoma, non-Hodgkin's lymphoma, colorectal cancer, non-small cell lung cancer, brain cancer, Kaposi's sarcoma, pancreatic cancer, liver cancer, and other tumors. Protein phosphatases are among the many modulators of kinase activity.

For example, the overexpression of PTKs, such as HER2, can play a decisive role in the development of cancer and that antibodies capable of blocking the activity of this enzyme can abrogate tumor growth. Blocking the signal transduction capability of tyrosine phosphatases such as Flk-1 and the PDGF receptor have been shown to block tumor growth in animal models.

The importance of phosphatases in the etiology of diseases has been well established. Malfunction of phosphatase activity has been associated with a number of human disorders. For example, the gene for human RPTPγ has been localized to chromosome 3p21 which is a segment frequently altered in renal and small lung carcinoma (Wary et al., Cancer Res 52:478–482, 1993). Loss of phosphatase activity in myotubularin-related protein 2 is associated with Charcot-Marie-Tooth disease type 4B1 (Berger P. et al., Hum Mol Genet 11:1569–79, 2002). There is also evidence linking the low-molecular-weight protein tyrosine phosphatase (LMPTP) to several common diseases, including allergy, asthma, obesity, myocardial hypertrophy, and Alzheimer's disease (Bottini N et al., Arch Immunol Ther Exp (Warsz) 50:95–104, 2002)

Regulation of signal transduction by cytokines and association of signal molecules with protooncogenes and tumor suppressor genes have been the subjects of intense research. Recent genetic and biochemical studies indicate that protein phosphatases, which play an important role in signal transduction process, represent a novel platform for drug discovery. Detailed knowledge of protein phosphatase substrate specificity and the wealth of structure data on protein phosphatases provide a solid foundation for rational phosphatase inhibitor design. Many therapeutic strategies can now be developed through the synthesis of compounds which activate or inactivate protein phosphatases.

The ability of phosphatase inhibitors to interfere with aberrant cell activity has been demonstrated. For example, the naturally occurring serine/threonine phosphatase inhibitor okadaic acid has been shown to induce apoptosis in myeloid leukemia cells (Ishida Y. et al., J. Cell. Physiol. 150:484, 1992) and in rat hepatocytes, rat pituitary adenoma cell, human mammary carcinoma cells and human neuroblastoma cells (Boe R. et al., Exp. Cell Res. 195:237, 1991). It is also well known that the immunosuppressive activity of cyclosporine A, a commonly used immunosuppressor in organ transplantation, is mediated by inhibiting calcineurin phosphatase. Recently, cyclosporin A was found to enhance taxol-induced apoptosis of human urinary bladder cancer cells (Nomura T. et al., Urol Res 30:102–11, 2002). The study suggests that the effect of cyclosporin A is at least partly due to the inhibition of calcineurin activity and the loss of the antiapoptotic function of Bcl-2 via the enhancement of phosphorylation and the reduction of expression.

In summary, phosphatase proteins are a major target for drug action and development. Accordingly, it is valuable to the field of pharmaceutical development to identify and characterize previously unknown members of phosphatase proteins. The present invention advances the state of the art by providing a novel human phosphatase protein that has sequence similarities to calcineurin-like phosphatases family. Specifically, the phosphatase domain in CLPP1 shares a 91.3% sequence identity with the consensus sequences of the calcineurin-like phosphatases. This domain, either in its native form or in a mutant form, can be used to affect the function of the corresponding domain in other phosphatases. The phosphatase domain in CLPP1 can be used to dephosphorylate suitable substrates.

The CLPP1 gene and the gene products can be used as molecular markers for diagnosing, prognosing, and monitoring the treatment of disorders related to the aberrant expression of CLPP1. The gene provided by the present invention can be expressed in yeast to identify possible interactors and substrates; this can be done by means of a complementation assay or a two-hybrid experiment. In addition, the CLPP1 gene can be used to screen for potential agents or drugs capable of enhancing or inhibiting the CLPP1 gene expression in human cells. The CLPP1 gene products (polynucleotide and polypeptide) can be used to screen for potential agents or drugs capable of enhancing or inhibiting CLPP1 activity. Artificially synthesized enzymes as well as derived peptides can be used to activate or inhibit cellular processes modulated by CLPP1. Immunoassay or PCR may be used to measure the concentration of CLPP1 and detect abnormally developing tissue or cancerous growth. Furthermore, various therapeutic methods for treating disorders related to the aberrant expression of CLPP1 can be designed based on the CLPP1 gene, its variants, or the agents/drugs that affect the expression of the CLPP1 gene or the activity of the CLPP1 gene products.

The following subsections illustrate examples of the utilities of human CLPP1 gene and CLPP1 phosphatase. Various changes and modifications within the scope of the present invention will become apparent to those skilled in the art from the present description.

Polynucleotides and Variants thereof

One aspect of the invention pertains to isolated polynucleotide probes capable of hybridizing to the CLPP1 gene or its transcripts, such as CLPP1 mRNAs. These probes can be used to detect the expression level of the CLPP1 gene in human tissue or cells. The present invention also contemplates polynucleotide fragments for use as PCR primers for the amplification or mutation of the CLPP1 gene or the CLPP1-coding sequences. Another aspect of the invention pertains to isolated polynucleotides that encode CLPP1, or a fragment or mutant thereof. These polynucleotides can be used for expressing CLPP1, or a fragment or mutant thereof. The protein products thus expressed can be used to screen for agents/drugs that modulate an activity of CLPP1. In addition, these polynucleotides can be used to designing gene therapy vectors which target the expression of the CLPP1 gene or an activity of CLPP1 in humans.

A polynucleotide comprising SEQ ID NO:1 or SEQ ID NO:3 can be prepared using standard molecular biology techniques as appreciated by one of ordinary skill in the art. For instance, primers derived from the 5' and 3' ends of SEQ ID NO:1 can be used to amplify mRNAs isolated from human tissues. The cDNA thus produced contains SEQ ID NO:1. Likewise, primers for amplifying the human genomic sequence containing SEQ ID NO:3 can be designed and used to prepare the genomic sequence of the CLPP1 gene. A variant (such as a homolog) or a fragment of SEQ ID NO:1 or SEQ ID NO:3 can be similarly prepared. Alternatively, probes can be designed to screen for cDNA or genomic sequence libraries in order to identify polynucleotide molecules comprising the full-length or fragments of SEQ ID NO:1 or SEQ ID NO:3. The molecules thus identified can be used to create suitable vectors comprising the full-length SEQ ID NO:1 or SEQ ID NO:3.

Polynucleotides capable of hybridizing to the CLPP1 gene can be prepared by standard synthetic techniques, e.g., using an automated DNA synthesizer. Preferably, the polynucleotide probes can hybridize to the CLPP1 gene under reduced stringent conditions, stringent conditions, or highly stringent conditions. In one embodiment, the polynucleotides comprise at least 15, 20, 25, 30, 50, 100, 150, 200, 250, 300, 350, 400, 450, 500, 550, 600, 650, 700, 750, 800, 850, 900, 950, 1000 or more consecutive nucleotides of SEQ ID NO:1. Any fragments of SEQ ID NO:1 and SEQ ID NO:3 may be used as hybridization probes or PCR primers for the CLPP1 gene or its transcripts. The probes/primers can be substantially purified.

In a preferred embodiment, the hybridization probes for the CLPP1 gene comprise a label group. The label group can be a radioisotope, a fluorescent compound, an enzyme, or an enzyme co-factor. Probes thus labeled can be used as part of a diagnostic kit for determining the expression level of the CLPP1 gene in human tissues.

This invention encompasses human CLPP1 gene homologs in other species. These homologs can be determined by search different sequence databases, such as the Entrez/GenBank sequence databases maintained by the NCBI. The invention also encompasses polynucleotide molecules which are structurally different from the molecules described above, but have the substantially same properties as the molecules described above. Such molecules include allelic variants, which will be described below in greater detail.

DNA sequence polymorphism in human CLPP1 gene exists among different individuals due to natural allelic variations. An allele is one of a group of genes which occur alternatively at a given genetic locus. DNA polymorphisms that affect the RNA expression level of the CLPP1 gene can also exist, e.g. through affecting the regulation or degradation of expression of the gene. The present invention contemplates all allelic variants of human CLPP1 gene. Allelic variants and other homologs of the CLPP1 gene can be isolated using probes/primers derived from SEQ ID NO:1 or SEQ ID NO:3.

It should, of course, be understood that SEQ ID NO:1 and SEQ ID NO:3 can be modified. The modified polynucleotides can comprise one or more mutations. These mutations can be substitutions, additions or deletions of 1, 2, 3, 5, 10, 15, 20 or more nucleotide residues in SEQ ID NO:1 or SEQ ID NO:3. Standard techniques can be used, such as site-directed mutagenesis or PCR-mediated mutagenesis. Preferably, these mutations create conservative amino acid substitutions. Alternatively, mutations can be introduced randomly along all or part of the CLPP1 gene or its cDNA, such as by saturation mutagenesis. Following mutagenesis, the encoded proteins can be expressed recombinantly and their activities can be determined.

In one embodiment, nucleotide substitutions leading to amino acid substitutions at "non-essential" amino acid residues can be introduced. A "non-essential" amino acid residue is a residue that can be altered without changing the biological activity of the protein. In contrast, an "essential" amino acid residue is required for the biological activity of the protein. Amino acid residues that are conserved among allelic variants or homologs of the CLPP1 gene from different species preferably are not changed in the present invention.

Accordingly, another aspect of the invention pertains to CLPP1 proteins that contain changes in amino acid residues that are not essential for the biological activity of CLPP1. These proteins differ in amino acid sequence from the original human CLPP1, but retain its biological activity. In one embodiment, the modified protein comprises an amino acid sequence at least about 85%, 90%, 95%, 98% or more homologous to SEQ ID NO:2.

In another embodiment, CLPP1 proteins contain mutations in amino acid residues which result in inhibition of CLPP1 activity. These mutated CLPP1 proteins can be used to inhibit CLPP1 activity in patients with disorders related to the aberrant expression of CLPP1.

A polynucleotide of this invention can be further modified to increase its stability in vivo. Possible modifications include, but are not limited to, the addition of flanking sequences at the 5' and/or 3' ends; the use of phosphorothioate or 2-o-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

Polynucleotide molecules which are antisense to the CLPP1 gene can be prepared. An "antisense" polynucleotide comprises a nucleotide sequence which is complementary to a "sense" polynucleotide which encodes a protein. An antisense polynucleotide can bind via hydrogen bonds to the sense polynucleotide.

Antisense polynucleotides of the invention can be designed according to the rules of Watson and Crick base pairing. The antisense polynucleotide molecule can be complementary to the entire coding region or part of the coding region of the CLPP1 gene. The antisense polynucleotide molecule can also be complementary to a "noncoding region" in the coding strand of the CLPP1 gene. Preferably, the antisense polynucleotide is an oligonucleotide which is antisense to only a portion of the CLPP1 gene. An antisense polynucleotide can be, for example, about 5, 10, 15, 20, 25, 30, 35, 40, 45 or 50 nucleotides in length. An antisense polynucleotide of the invention can be constructed using chemical synthesis and enzymatic ligation reactions as appreciated by one of ordinary skill in the art. For example, an antisense polynucleotide can be chemically synthesized using naturally occurring nucleotides or variously modified nucleotides designed to increase the biological stability of the molecules or to increase the physical stability of the duplex formed between the antisense and sense polynucleotides. Examples of modified nucleotides which can be used to generate the antisense polynucleotide include 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyl adenosine, unacil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, (acp3)w, and 2,6-diaminopurine. Phosphorothioate derivatives and acridine substituted nucleotides can also be used. Alternatively, the antisense polynucleotide can be produced biologically using an expression vector into which a polynucleotide has been subcloned in an antisense orientation (i.e., RNA transcribed from the inserted polynucleotide will be of an antisense orientation to the target polynucleotide of interest).

The antisense polynucleotides of the invention can be administered to a subject or applied in situ such that they hybridize or bind to cellular mRNAs and/or genomic DNAs that encode CLPP1, thereby inhibiting the expression of CLPP1. The hybridization can result in a stable duplex via conventional nucleotide complementarity. An example route for administering antisense polynucleotides includes direct injection at a tissue site. Antisense polynucleotides can also be modified first, and then administered systemically. For example, for systemic administration, antisense molecules can be modified such that they specifically bind to receptors or antigens expressed on a selected cell surface. Suitable modifications include linking the antisense polynucleotides to peptides or antibodies which bind to the cell surface receptors or antigens. In addition, the antisense polynucleotides can be delivered to cells using vectors. To achieve sufficient intracellular concentrations of the antisense molecules, strong pol II or pol III promoters may be used in the vectors.

In one embodiment, the antisense polynucleotides are α-anomeric polynucleotides. An α-anomeric polynucleotide molecule forms specific double-stranded hybrid with a complementary RNA in which, contrary to the usual β-units, the strands run parallel to each other. The antisense polynucleotide molecule can also comprise a 2-o-methylribonucleotide or a chimeric RNA-DNA analogue.

In another embodiment, the antisense polynucleotide is a ribozyme. Ribozymes are catalytic RNA molecules with ribonuclease activity which are capable of cleaving a single-stranded polynucleotide, such as an mRNA, to which they have a complementary region. Thus, ribozymes (e.g., hammerhead ribozymes described in Haselhoif and Gerlach Nature 334:585–591, 1988) can be used to catalytically cleave mRNA transcripts of CLPP1 in order to inhibit its expression. A ribozyme having specificity for the CLPP1 gene or its transcripts can be designed based upon SEQ ID NO:1 or 3. mRNAs transcribed from the CLPP1 gene can be used to select from a pool of RNA molecules a catalytic RNA having a specific ribonuclease activity.

Alternatively, the expression of the CLPP1 gene can be inhibited by using nucleotide sequences complementary to the regulatory region (e.g., the promoter and/or enhancers). These nucleotide sequences can form triple helical structures that prevent transcription of the gene in the target cells.

Expression of the CLPP1 gene can also be inhibited using RNA interference ("RNAi"). RNAi is a phenomenon in which the introduction of double-stranded RNA (dsRNA) into certain organisms or cell types causes degradation of the homologous mRNA. First discovered in the nematode *Caenorhabditis elegans*, RNAi has since been found to operate in a wide range of organisms. For example, in mammalian cells, introduction of long dsRNA (>30 nucleotides) can initiate a potent antiviral response, exemplified by nonspecific inhibition of protein synthesis and RNA degradation. RNA interference provides a mechanism of gene silencing at the mRNA level. In recent years, RNAi has become an endogenous and potent gene-specific silencing technique that uses double-stranded RNAs (dsRNA) to mark a particular transcript for degradation in vivo. It also offers an efficient and broadly applicable approach for gene knockout. In addition, RNAi technology can be used for therapeutic purposes. For example, RNAi targeting Fas-mediated apoptosis has been shown to protect mice from fulminant hepatitis. RNAi technology has been disclosed in numerous publications, such as U.S. Pat. Nos. 5,919,619, 6,506,559 and PCT Publication Nos. WO99/14346, WO01/70949, WO01/36646, WO00/63364, WO00/44895, WO01/75164, WO01/92513, WO01/68836 and WO01/29058.

A sequence capable of inhibiting gene expression by RNA interference can have any length. For instance, the sequence can have at least 10, 15, 20, 25, 30, 35, 40, 45, 50, 100, or more consecutive nucleotides. The sequence can be dsRNA or any other type of polynucleotide, provided that the sequence can form a functional silencing complex to degrade the target mRNA transcript.

In one embodiment, the sequence comprises or consists of a short interfering RNA (siRNA). The siRNA can be dsRNA having 19–25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence-specific mRNA degradation results in gene silencing.

At least two ways can be employed to achieve siRNA-mediated gene silencing. First, siRNAs can be synthesized in vitro and introduced into cells to transiently suppress gene expression. Synthetic siRNA provides an easy and efficient way to achieve RNAi. siRNA are duplexes of short mixed oligonucleotides which can include, for example, 19 nucleotides with symmetric dinucleotide 3' overhangs. Using synthetic 21 bp siRNA duplexes (e.g., 19 RNA bases followed by a UU or dTdT 3' overhang), sequence-specific gene silencing can be achieved in mammalian cells. These siRNAs can specifically suppress targeted gene translation in mammalian cells without activation of DNA-dependent protein kinase (PKR) by longer dsRNA, which may result in non-specific repression of translation of many proteins.

Second, siRNAs can be expressed in vivo from vectors. This approach can be used to stably express siRNAs in cells or transgenic animals. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (e.g., UU) to hairpin siRNAs—a feature that is helpful for siRNA function. The Pol III expression vectors can also be used to create transgenic mice that express siRNA.

In another embodiment, siRNAs can be expressed in a tissue-specific manner. Under this approach, long double-stranded RNAs (dsRNAs) are first expressed from a promoter (such as CMV (pol II)) in the nuclei of selected cell lines or transgenic mice. The long dsRNAs are processed into siRNAs in the nuclei (e.g., by Dicer). The siRNAs exit from the nuclei and mediate gene-specific silencing. A similar approach can be used in conjunction with tissue-specific promoters to create tissue-specific knockdown mice.

Any 3' dinucleotide overhang, such as UU, can be used for siRNA design. In some cases, G residues in the overhang are avoided because of the potential for the siRNA to be cleaved by RNase at single-stranded G residues.

With regard to the siRNA sequence itself, it has been found that siRNAs with 30–50% GC content can be more active than those with a higher G/C content in certain cases. Moreover, since a 4–6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database (human, mouse, rat, etc.). Any target sequences with more than 16–17 contiguous base pairs of homology to other coding sequences may be eliminated from consideration in certain cases.

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., Proc. Natl. Acad. Sci. USA 99: 5515–5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., Nature Biotechnology 20:500–505, 2002).

In another embodiment, the hairpin siRNA expression cassette is constructed to contain the sense strand of the target, followed by a short spacer, the antisense strand of the target, and 5–6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In still yet another embodiment, the target sequence for RNAi is a 21-mer sequence fragment selected from SEQ ID NO:1. The 5' end of the target sequence has dinucleotide "NA," where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a role. Exemplary RNAi target sequences identified according to the above-described criteria ("relaxed" criteria) are illustrated in Table 3. The siRNA sequences for each target sequence (listed in the row as the target sequence and including the sense strand and the antisense strand) are also indicated in Table 3.

Additional criteria can also be used for RNAi target sequence design. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases is excluded.

Furthermore, the remaining 19-mer sequence can be selected to have low sequence homology to other human genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected. During the search, the e-value may be set at a stringent value (such as "1"). Exemplary target sequences derived using these additional conditions ("stringent" criteria) are shown in Table 4. The siRNA sequences for each target sequence (listed in the same row as the target sequence and including the sense strand and the antisense strand) are also indicated in Table 4.

The effectiveness of the siRNA sequences listed in Tables 3 and 4, as well as any other RNAi sequence derived according to the present invention, can be evaluated using various methods known in the art. For instance, a siRNA sequence of the present invention can be introduced into a cell that expresses the CLPP1 gene. The polypeptide or mRNA level of the CLPP1 gene in the cell can be detected. A substantial change in the expression level of the CLPP1 gene before and after the introduction of the siRNA sequence is indicative of the effectiveness of the siRNA sequence in suppressing the expression of the CLPP1 gene. In one specific example, the expression levels of other genes are also monitored before and after the introduction of the siRNA sequence. A siRNA sequence which has inhibitory effect on CLPP1 gene expression but does not significantly affect the expression of other genes can be selected. In another specific example, multiple siRNA or other RNAi sequences can be introduced into the same target cell. These siRNA or RNAi sequences specifically inhibit CLPP1 gene expression but not the expression of other genes. In yet another specific example, siRNA or other RNAi sequences that inhibit the expression of both the CLPP1 gene and other gene or genes can be used.

TABLE 3

Exemplary RNAi Target Sequences in the CLPP1 Gene and the Corresponding siRNAs (Under Relaxed Criteria)

| Target Sequence | siRNA Sense Strand | siRNA Antisense Strand |
|---|---|---|
| SEQ ID NO: 4 | SEQ ID NO: 5 | SEQ ID NO: 6 |
| SEQ ID NO: 7 | SEQ ID NO: 8 | SEQ ID NO: 9 |
| SEQ ID NO: 10 | SEQ ID NO: 11 | SEQ ID NO: 12 |
| SEQ ID NO: 13 | SEQ ID NO: 14 | SEQ ID NO: 15 |
| SEQ ID NO: 16 | SEQ ID NO: 17 | SEQ ID NO: 18 |
| SEQ ID NO: 19 | SEQ ID NO: 20 | SEQ ID NO: 21 |
| SEQ ID NO: 22 | SEQ ID NO: 23 | SEQ ID NO: 24 |
| SEQ ID NO: 25 | SEQ ID NO: 26 | SEQ ID NO: 27 |
| SEQ ID NO: 28 | SEQ ID NO: 29 | SEQ ID NO: 30 |
| SEQ ID NO: 31 | SEQ ID NO: 32 | SEQ ID NO: 33 |
| SEQ ID NO: 34 | SEQ ID NO: 35 | SEQ ID NO: 36 |
| SEQ ID NO: 37 | SEQ ID NO: 38 | SEQ ID NO: 39 |
| SEQ ID NO: 40 | SEQ ID NO: 41 | SEQ ID NO: 42 |
| SEQ ID NO: 43 | SEQ ID NO: 44 | SEQ ID NO: 45 |
| SEQ ID NO: 46 | SEQ ID NO: 47 | SEQ ID NO: 48 |
| SEQ ID NO: 49 | SEQ ID NO: 50 | SEQ ID NO: 51 |
| SEQ ID NO: 52 | SEQ ID NO: 53 | SEQ ID NO: 54 |
| SEQ ID NO: 55 | SEQ ID NO: 56 | SEQ ID NO: 57 |
| SEQ ID NO: 58 | SEQ ID NO: 59 | SEQ ID NO: 60 |
| SEQ ID NO: 61 | SEQ ID NO: 62 | SEQ ID NO: 63 |
| SEQ ID NO: 64 | SEQ ID NO: 65 | SEQ ID NO: 66 |
| SEQ ID NO: 67 | SEQ ID NO: 68 | SEQ ID NO: 69 |
| SEQ ID NO: 70 | SEQ ID NO: 71 | SEQ ID NO: 72 |
| SEQ ID NO: 73 | SEQ ID NO: 74 | SEQ ID NO: 75 |
| SEQ ID NO: 76 | SEQ ID NO: 77 | SEQ ID NO: 78 |

TABLE 3-continued

Exemplary RNAi Target Sequences in the CLPP1 Gene and the Corresponding siRNAs (Under Relaxed Criteria)

| Target Sequence | siRNA Sense Strand | siRNA Antisense Strand |
|---|---|---|
| SEQ ID NO: 79 | SEQ ID NO: 80 | SEQ ID NO: 81 |
| SEQ ID NO: 82 | SEQ ID NO: 83 | SEQ ID NO: 84 |
| SEQ ID NO: 85 | SEQ ID NO: 86 | SEQ ID NO: 87 |
| SEQ ID NO: 88 | SEQ ID NO: 89 | SEQ ID NO: 90 |
| SEQ ID NO: 91 | SEQ ID NO: 92 | SEQ ID NO: 93 |
| SEQ ID NO: 94 | SEQ ID NO: 95 | SEQ ID NO: 96 |
| SEQ ID NO: 97 | SEQ ID NO: 98 | SEQ ID NO: 99 |
| SEQ ID NO: 100 | SEQ ID NO: 101 | SEQ ID NO: 102 |
| SEQ ID NO: 103 | SEQ ID NO: 104 | SEQ ID NO: 105 |
| SEQ ID NO: 106 | SEQ ID NO: 107 | SEQ ID NO: 108 |
| SEQ ID NO: 109 | SEQ ID NO: 110 | SEQ ID NO: 111 |
| SEQ ID NO: 112 | SEQ ID NO: 113 | SEQ ID NO: 114 |
| SEQ ID NO: 115 | SEQ ID NO: 116 | SEQ ID NO: 117 |
| SEQ ID NO: 118 | SEQ ID NO: 119 | SEQ ID NO: 120 |
| SEQ ID NO: 121 | SEQ ID NO: 122 | SEQ ID NO: 123 |
| SEQ ID NO: 124 | SEQ ID NO: 125 | SEQ ID NO: 126 |
| SEQ ID NO: 127 | SEQ ID NO: 128 | SEQ ID NO: 129 |
| SEQ ID NO: 130 | SEQ ID NO: 131 | SEQ ID NO: 132 |
| SEQ ID NO: 133 | SEQ ID NO: 134 | SEQ ID NO: 135 |
| SEQ ID NO: 136 | SEQ ID NO: 137 | SEQ ID NO: 138 |
| SEQ ID NO: 139 | SEQ ID NO: 140 | SEQ ID NO: 141 |
| SEQ ID NO: 142 | SEQ ID NO: 143 | SEQ ID NO: 144 |
| SEQ ID NO: 145 | SEQ ID NO: 146 | SEQ ID NO: 147 |
| SEQ ID NO: 148 | SEQ ID NO: 149 | SEQ ID NO: 150 |
| SEQ ID NO: 151 | SEQ ID NO: 152 | SEQ ID NO: 153 |
| SEQ ID NO: 154 | SEQ ID NO: 155 | SEQ ID NO: 156 |
| SEQ ID NO: 157 | SEQ ID NO: 158 | SEQ ID NO: 159 |
| SEQ ID NO: 160 | SEQ ID NO: 161 | SEQ ID NO: 162 |
| SEQ ID NO: 163 | SEQ ID NO: 164 | SEQ ID NO: 165 |
| SEQ ID NO: 166 | SEQ ID NO: 167 | SEQ ID NO: 168 |
| SEQ ID NO: 169 | SEQ ID NO: 170 | SEQ ID NO: 171 |
| SEQ ID NO: 172 | SEQ ID NO: 173 | SEQ ID NO: 174 |
| SEQ ID NO: 175 | SEQ ID NO: 176 | SEQ ID NO: 177 |
| SEQ ID NO: 178 | SEQ ID NO: 179 | SEQ ID NO: 180 |
| SEQ ID NO: 181 | SEQ ID NO: 182 | SEQ ID NO: 183 |
| SEQ ID NO: 184 | SEQ ID NO: 185 | SEQ ID NO: 186 |
| SEQ ID NO: 187 | SEQ ID NO: 188 | SEQ ID NO: 189 |
| SEQ ID NO: 190 | SEQ ID NO: 191 | SEQ ID NO: 192 |
| SEQ ID NO: 193 | SEQ ID NO: 194 | SEQ ID NO: 195 |
| SEQ ID NO: 196 | SEQ ID NO: 197 | SEQ ID NO: 198 |
| SEQ ID NO: 199 | SEQ ID NO: 200 | SEQ ID NO: 201 |
| SEQ ID NO: 202 | SEQ ID NO: 203 | SEQ ID NO: 204 |
| SEQ ID NO: 205 | SEQ ID NO: 206 | SEQ ID NO: 207 |
| SEQ ID NO: 208 | SEQ ID NO: 209 | SEQ ID NO: 210 |
| SEQ ID NO: 211 | SEQ ID NO: 212 | SEQ ID NO: 213 |
| SEQ ID NO: 214 | SEQ ID NO: 215 | SEQ ID NO: 216 |
| SEQ ID NO: 217 | SEQ ID NO: 218 | SEQ ID NO: 219 |
| SEQ ID NO: 220 | SEQ ID NO: 221 | SEQ ID NO: 222 |
| SEQ ID NO: 223 | SEQ ID NO: 224 | SEQ ID NO: 225 |
| SEQ ID NO: 226 | SEQ ID NO: 227 | SEQ ID NO: 228 |
| SEQ ID NO: 229 | SEQ ID NO: 230 | SEQ ID NO: 231 |
| SEQ ID NO: 232 | SEQ ID NO: 233 | SEQ ID NO: 234 |
| SEQ ID NO: 235 | SEQ ID NO: 236 | SEQ ID NO: 237 |
| SEQ ID NO: 238 | SEQ ID NO: 239 | SEQ ID NO: 240 |
| SEQ ID NO: 241 | SEQ ID NO: 242 | SEQ ID NO: 243 |
| SEQ ID NO: 244 | SEQ ID NO: 245 | SEQ ID NO: 246 |
| SEQ ID NO: 247 | SEQ ID NO: 248 | SEQ ID NO: 249 |
| SEQ ID NO: 250 | SEQ ID NO: 251 | SEQ ID NO: 252 |
| SEQ ID NO: 253 | SEQ ID NO: 254 | SEQ ID NO: 255 |
| SEQ ID NO: 256 | SEQ ID NO: 257 | SEQ ID NO: 258 |
| SEQ ID NO: 259 | SEQ ID NO: 260 | SEQ ID NO: 261 |
| SEQ ID NO: 262 | SEQ ID NO: 263 | SEQ ID NO: 264 |
| SEQ ID NO: 265 | SEQ ID NO: 266 | SEQ ID NO: 267 |
| SEQ ID NO: 268 | SEQ ID NO: 269 | SEQ ID NO: 270 |

TABLE 4

Exemplary RNAi Target Sequences in the CLPP1 Gene and the Corresponding siRNAs (Under Stringent Criteria)

| Target Sequence | siRNA Sense Strand | siRNA Antisense Strand |
|---|---|---|
| SEQ ID NO: 271 | SEQ ID NO: 272 | SEQ ID NO: 273 |
| SEQ ID NO: 274 | SEQ ID NO: 275 | SEQ ID NO: 276 |
| SEQ ID NO: 277 | SEQ ID NO: 278 | SEQ ID NO: 279 |
| SEQ ID NO: 280 | SEQ ID NO: 281 | SEQ ID NO: 282 |
| SEQ ID NO: 283 | SEQ ID NO: 284 | SEQ ID NO: 285 |
| SEQ ID NO: 286 | SEQ ID NO: 287 | SEQ ID NO: 288 |
| SEQ ID NO: 289 | SEQ ID NO: 290 | SEQ ID NO: 291 |
| SEQ ID NO: 292 | SEQ ID NO: 293 | SEQ ID NO: 294 |
| SEQ ID NO: 295 | SEQ ID NO: 296 | SEQ ID NO: 297 |
| SEQ ID NO: 298 | SEQ ID NO: 299 | SEQ ID NO: 300 |
| SEQ ID NO: 301 | SEQ ID NO: 302 | SEQ ID NO: 303 |

In yet another embodiment, the polynucleotides of the present invention can be modified at the base moiety, sugar moiety or phosphate backbone to improve the stability, hybridization, or solubility of the molecules. For instance, the deoxyribose phosphate backbone of the polynucleotide molecules can be modified to generate peptide polynucleotides (see Hyrup et al., Bioorganic & Medicinal Chemistry 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. PNA oligomers can be synthesized using standard solid phase peptide synthesis protocols.

PNAs can be used in therapeutic and diagnostic applications. For example, PNAs can be used as antisense agents for sequence-specific modulation of the CLPP1 gene expression. PNAs can also be used in the analysis of single base pair mutations in a gene, (e.g., by PNA-directed PCR clamping); as artificial restriction enzymes when used in combination with other enzymes, (e.g., S1 nucleases); or as probes or primers for DNA sequencing or hybridization.

In one embodiment, PNAs can be modified to enhance their stability or cellular uptake by attaching lipophilic or other helper groups to PNA, by the formation of PNA-DNA chimeras, or by the use of liposomes or other drug delivery techniques known in the art. For example, PNA-DNA chimeras of the polynucleotides of the invention can be generated. These chimeras allow DNA recognition enzymes, such as RNase H and DNA polymerases, to interact with the DNA portion while the PNA portion provides high binding affinity and specificity. PNA-DNA chimeras can be linked using linkers of appropriate lengths which are selected based on base stacking, number of bonds between the nucleobases, and orientations. The PNA-DNA chimeras can be synthesized as follows. A DNA chain is synthesized on a solid support using standard phosphoramidite coupling chemistry and modified nucleoside analogs. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

In other embodiments, the polynucleotides of this invention may include other appended groups such as peptides (e.g., for targeting host cell receptors in vivo), or agents facilitating transportation across the cell membrane or the blood-kidney barrier (see e.g., PCT Publication No. WO89/10134). In addition, polynucleotides can be modified using hybridization-triggered cleavage agents or intercalating agents. To this end, the polynucleotides can be conjugated to another molecule (e.g., a peptide, hybridization triggered cross-linking agent, transport agent, or hybridization-triggered cleavage agent). Furthermore, the polynucleotide can be detectably labeled.

Polypeptides and Variants thereof

Several aspects of the invention pertain to isolated CLPP1 polypeptides and mutated CLPP1 polypeptides capable of inhibiting normal CLPP1 activity. The present invention also contemplates immunogenic polypeptide fragments suitable for raising anti-CLPP1 antibodies.

In one embodiment, native CLPP1 polypeptides can be isolated from cells or tissue sources by using standard protein purification techniques. Standard purification methods include electrophoresis, molecular, immunological and chromatographic techniques. Specific examples include ion exchange, hydrophobic, affinity or reverse-phase HPLC chromatography, and chromatofocusing. In one embodiment, CLPP1 polypeptides are purified using a standard affinity column coupled with anti-CLPP1 antibodies. Ultrafiltration and diafiltration techniques can also be used. The degree of purification depends on the purpose of the use of the CLPP1 polypeptides. In some instances, purification is not necessary.

In another embodiment, CLPP1 polypeptides or mutated CLPP1 polypeptides capable of inhibiting normal CLPP1 activity are produced by recombinant DNA techniques. Alternative to recombinant expression, CLPP1 polypeptides or mutated CLPP1 polypeptides can be synthesized chemically using standard peptide synthesis techniques.

The invention provides CLPP1 polypeptides encoded by the human CLPP1 gene, or homologs thereof. The polypeptides of this invention can be substantially homologous to human CLPP1 (SEQ ID NO:2). Preferably, these polypeptides retain the biological activity of the native CLPP1. In one embodiment, the polypeptides comprise an amino acid sequence which is at least about 85%, 90%, 95%, 98% or more homologous to SEQ ID NO:2.

Comparison of sequences and determination of percent identity between two sequences can be accomplished using a mathematical algorithm. The percent identity between two amino acid sequences can be determined using the Needleman and Wunsch (J. Mol. Biol. 48:444–453, 1970) algorithm, or the GAP program in the GCG software package which uses either a Blossom 62 matrix or a PAM250 matrix, and a gap weight of 16, 14, 12, 10, 8, 6, or 4 and a length weight of 1, 2, 3, 4, 5, or 6. The percent identity between two nucleotide sequences can be determined using the GAP program in the GCG software package, which uses a NWSgapdna.CMP matrix and a gap weight of 40, 50, 60, 70, or 80 and a length weight of 1, 2, 3, 4, 5, or 6. The percent identity between two amino acid or nucleotide sequences can also be determined using the algorithm of E. Meyers and W. Miller (CABIOS, 4:11–17, 1989) which has been incorporated into the ALIGN program (version 2.0), or the pairwise BLAST program available at NCBI's BLAST web site.

The polypeptide and polynucleotide sequences of the present invention can be used as query sequences for searching public databases in order to identify similar sequences. The search can be conducted using BLAST programs, such as the protein BLAST, nucleotide BLAST, pairwise BLAST, and genomic BLAST, that are available at the BLAST web site maintained by the NCBI. When using BLAST programs, the default parameters of the respective programs can also be used.

The invention further provides chimeric or fusion CLPP1 polypeptides. A fusion CLPP1 polypeptide contains an CLPP1-related polypeptide and a non-CLPP1 polypeptide. The CLPP1-related polypeptides include all or a portion of SEQ ID NO:2 or its variant. A peptide linker sequence can be employed to separate the CLPP1-related polypeptide from the non-CLPP1 polypeptide components by a distance sufficient to ensure that each polypeptide folds into its native secondary and tertiary structures. Such a peptide linker sequence is incorporated into the fusion protein using standard techniques well known in the art. Suitable peptide linker sequences can be chosen based on the following factors: (1) their ability to adopt a flexible extended conformation; (2) their inability to adopt a secondary structure that could interact with functional epitopes on the CLPP1-related polypeptide and non-CLPP1 polypeptide; and (3) the lack of hydrophobic or charged residues that might react with the polypeptide functional epitopes. Preferred peptide linker sequences contain Gly, Asn and Ser residues. Other near neutral amino acids, such as Thr and Ala can also be used in the linker sequence. Amino acid sequences suitable as linkers include those disclosed in Maratea et al., Gene 40:39–46, 1985; Murphy et al., Proc. Natl. Acad. Sci. USA 83:8258–8262, 1986; and U.S. Pat. Nos. 4,935,233 and 4,751,180. The linker sequences may be from 1 to about 50 amino acids in length. Linker sequences are not required when the CLPP1-related polypeptide or the non-CLPP1 polypeptide has non-essential N-terminal amino acid regions that can be used to separate the respective functional domains and thereby prevent steric interference.

In one embodiment, the fusion protein is a GST-CLPP1 fusion protein in which an CLPP1-related sequence, such as SEQ ID NO:2, is fused to the C-terminus of the GST sequence. This fusion protein can facilitate the purification of the recombinant CLPP1.

The CLPP1-fusion proteins of the invention can be incorporated into pharmaceutical compositions and administered to a subject. The CLPP1-fusion proteins can be used to affect the bioavailability of an CLPP1 substrate. The CLPP1-fusion proteins can also be used for the treatment or prevention of damages caused by (i) aberrant modification or mutation of CLPP1, or (ii) aberrant post-translational modification of CLPP1. It is also conceivable that a fusion protein containing a normal or mutated CLPP1 polypeptide, or a fragment thereof, can be used to inhibit CLPP1 activity in a human subject.

Moreover, the CLPP1-fusion proteins can be used as immunogens to produce anti-CLPP1 antibodies. They can also be used to purify CLPP1 ligands and to screen for molecules capable of inhibiting the interaction between CLPP1 and its substrates.

Preferably, the CLPP1-chimeric or fusion proteins of the invention are produced using standard recombinant DNA techniques. Commercially available expression vectors which encode a fusion moiety (e.g., a GST polypeptide) can be used.

A signal sequence can be used to facilitate secretion and isolation of the secreted protein or other proteins of interest. Signal sequences are typically characterized by a core of hydrophobic amino acids which are generally cleaved from the mature protein. Such signal peptides contain processing sites that allow cleavage of the signal sequence from the mature proteins as they pass through the secretory pathway.

The present invention encompasses CLPP1 polypeptides having a signal sequence, or the polynucleotide sequences encoding the same.

The present invention also pertains to CLPP1 mutants which function as antagonists to CLPP1. In one embodiment, antagonists of CLPP1 are used as therapeutic agents. For example, a mutant of CLPP1 that forms a non-functional dimer with a wide-type CLPP1 (the so-called dominant negative mutant) can decrease the activity of CLPP1 and may ameliorate diseases in a subject wherein CLPP1 are abnormally increased in level or activity. Dominant negative CLPP1 mutants can be generated by mutagenesis, as appreciated by one skilled in the art.

CLPP1 mutants which function as either CLPP1 agonists or antagonists can be identified by screening combinatorial libraries of mutants. A variegated library of CLPP1 mutants can be produced by, for example, enzymatically ligating a mixture of synthetic oligonucleotides into gene sequences such that a degenerate set of potential CLPP1 sequences is expressible as individual polypeptides, or alternatively, as a set of larger fusion proteins containing the set of CLPP1 sequences therein. There are a variety of methods which can be used to produce libraries of potential CLPP1 mutants from a degenerate oligonucleotide sequence. A degenerate gene sequence can be chemically synthesized using an automatic DNA synthesizer. The synthetic gene can then be ligated into an appropriate expression vector.

In one embodiment, a library of coding sequences can be generated using nucleases. For instance, double stranded PCR fragments of the CLPP1 coding sequence can be treated by a nuclease which produces about one nick per molecule. The double-stranded DNAs then are subject to a cycle of denaturing and re-naturing. The newly reformed DNAs, which may include sense/antisense pairs from different nicked products, are treated with S1 nuclease to remove single stranded portions. Using this method, an expression library which encodes N-terminal, C-terminal or internal fragments of CLPP1 can be derived.

In addition, recursive ensemble mutagenesis (REM), a technique which enhances the frequency of functional mutants in the libraries, can be used to prepare CLPP1 mutants (Delgrave et al., Protein Engineering 6:327–331, 1993).

CLPP1 fragments, or variants thereof, can also be generated using synthetic means, such as solid-phase synthesis methods. Preferably, the synthesized fragment has less than about 100 amino acids, or preferably, less than about 50 amino acids. fragments, or variants thereof, can also be generated using synthetic means, such as solid-phase synthesis methods. Preferably, the synthesized fragment has less than about 100 amino acids, or preferably, less than about 50 amino acids.

Antibodies

In accordance with another aspect of the present invention, antibodies specific to CLPP1 or its variants are prepared. An antibody is considered to bind "specifically" to an antigen if the binding affinity between the antibody and the antigen is equal to, or greater than $10^5$ $M^{-1}$. The antibodies can be monoclonal or polyclonal. Preferably, the antibodies are monoclonal. More preferably, the antibodies are humanized antibodies.

Polyclonal anti-CLPP1 antibodies can be prepared by immunizing a suitable subject with CLPP1 or fragments thereof. The anti-CLPP1 antibody titer in the immunized subject can be monitored over the time using standard techniques, such as ELISA. The anti-CLPP1 antibody can be isolated from the immunized subject using well known techniques.

In one embodiment, hybridomas capable of producing anti-CLPP1 antibodies are prepared. Purified CLPP1 or its variants, or fragments thereof, are used to immunize a vertebrate, such as a mammal. Suitable mammals include mice, rabbits and sheep. Preferably, the fragment used for immunization comprises at least 8 amino acid residues, more preferably at least 12 amino acid residues, highly preferably at least 16 amino acid residues, and most preferably at least 20 amino acid residues.

Immunogenic fragments (epitopes) of CLPP1 can be identified using well known techniques. In general, any fragment of SEQ ID NO:2 can be used to raise antibodies specific to CLPP1. Preferred epitopes are regions that are located on the surface of CLPP1. These regions are usually hydrophilic.

Splenocytes are isolated from the immunized vertebrate and fused with an immortalized cell line (such as a myeloma) to form hybridomas. Preferably, the immortal cell line is derived from the same mammalian species as the lymphocytes. For example, murine hybridomas can be made by fusing an immortalized mouse cell line with lymphocytes isolated from a mouse that is immunized with an immunogenic preparation of the present invention. Preferred immortalized cell lines include mouse myeloma cell lines that are sensitive to culture medium containing hypoxanthine, aminopterin and thymidine ("HAT medium"). Suitable myeloma cell lines include, but are not limited to, the P3-NS1/1-Ag4-1, P3-x63-Ag8.653 or Sp210-Ag14 myeloma lines, all of which are available from ATCC. In one embodiment, HAT-sensitive mouse myeloma cells are fused to mouse splenocytes using polyethylene glycol ("PEG"). Hybridoma cells thus produced are selected against HAT medium, which kills unfused or unproductively fused myeloma cells. Hybridoma cells which produce monoclonal anti-CLPP1 antibodies are then detected by screening the hybridoma culture supernatants.

A monoclonal anti-CLPP1 antibody can also be prepared by screening a recombinant combinatorial immunoglobulin library (e.g., an antibody phage display library). Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

The anti-CLPP1 antibodies of the present invention also include "single-chain Fv" or "scFv." The scFv fragments comprise the $V_H$ and $V_L$ domains of an antibody. Generally, the scFv polypeptide further comprises a polypeptide linker between the $V_H$ and $V_L$ domains. The polypeptide linker enables the scFv to form the desired structure for antigen binding. Additionally, recombinant anti-CLPP1 antibodies, such as chimeric and humanized monoclonal antibodies, can be prepared, as appreciated by one of ordinary skill in the art.

Humanized antibodies are particularly desirable for therapeutic treatment of human subjects. Humanized forms of non-human (e.g., murine) antibodies are chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. Humanized antibodies are derived from human immunoglobulins in which the residues forming the complementary determining regions (CDRs) are replaced by the residues from CDRs of a non-human antibody, such as a mouse, rat or rabbit antibody having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. The humanized antibody can comprise at least one or two variable domains, in which all or substantially all of the CDR regions correspond to those of a non-human immunoglobulin and all or substantially all of the constant regions are those of a human immunoglobulin consensus sequence. The humanized antibody preferably comprises at least a portion of an immunoglobulin constant region (Fc) of a human immunoglobulin.

Humanized antibodies can be produced using transgenic mice which are incapable of expressing endogenous immunoglobulin heavy and light chains but can express human heavy and light chains. The transgenic mice are immunized in the normal fashion with a selected antigen. Monoclonal antibodies directed against the antigen can be obtained using conventional hybridoma technology. The human immunoglobulin transgenes harbored in the transgenic mice rearrange during B cell differentiation, and subsequently undergo class switching and somatic mutation. Using this technique, therapeutically useful IgG, IgA and IgE antibodies can be prepared.

In addition, humanized antibodies which recognize a selected epitope can be generated using a technique referred to as "guided selection." In this approach a selected non-human monoclonal antibody, e.g., a murine antibody, is used to guide the selection of a humanized antibody recognizing the same epitope.

In a preferred embodiment, the antibodies to CLPP1 are capable of reducing or eliminating the biological function of CLPP1. Preferably, the antibodies reduce at least 25% of CLPP1 activity. More preferably, the antibodies reduce at least about 50% of the activity. Highly preferably, the antibodies reduce about 95–100% of CLPP1 activity.

Anti-CLPP1 antibodies can be used to isolate CLPP1. Suitable methods include affinity chromatography and immunoprecipitation. Moreover, anti-CLPP1 antibodies can be used to evaluate the expression level of CLPP1. Anti-CLPP1 antibodies can also be used to monitor CLPP1 level as part of a clinical testing procedure, or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include $^{125}$I, $^{131}$I, $^{35}$S or $^{3}$H.

Anti-CLPP1 antibodies are also useful for targeting a therapeutic agent/drug to a particular cell or tissue. The therapeutic agent/drug may be coupled to an antibody, either covalently or non-covalently. For instance, a therapeutic agent can be coupled to an antibody via a linker group. A linker group can function as a spacer to separate the antibody from the agent so as to avoid interference with antibody's binding capabilities. The linker group can also serve to increase the chemical reactivity of a substituent on the agent or the antibody, and thus increase the coupling efficiency. A variety of bifunctional or polyfunctional reagents, either homo- or hetero-functional (such as those described in the catalog of the Pierce Chemical Co., Rockford, Ill.), can be employed as the linker group. Coupling may be effected, for example, through amino groups, carboxyl groups, sulfhydryl groups or oxidized carbohydrate residues. There are numerous references describing this methodology. See, e.g., U.S. Pat. No. 4,671,958.

Where a therapeutic agent is more potent when free from the antibody, it may be desirable to use a linker group which is cleavable during or upon internalization into the target cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), or by acid-catalyzed hydrolysis (e.g., U.S. Pat. No. 4,569,789).

It may also be desirable to couple more than one agent to an antibody. In one embodiment, multiple agents are coupled to one antibody molecule. In another embodiment, at least two different types of agents are coupled to one antibody. Regardless of the particular embodiment, immunoconjugates coupled with more than one agent can be prepared in a variety of ways, as appreciated by one of ordinary skill in the art.

Vectors, Expression Vectors and Gene Delivery Vectors

Another aspect of the invention pertains to vectors containing a polynucleotide encoding CLPP1 or a portion thereof. One type of vector is a "plasmid," which includes a circular double stranded DNA into which additional DNA segments can be introduced. Vectors also include expression vectors and gene delivery vectors.

The expression vectors of the present invention comprise a polynucleotide encoding CLPP1 or a portion thereof. The expression vectors also include one or more regulatory sequences operably linked to the polynucleotide being expressed. These regulatory sequences are selected based on the type of host cells. It will be appreciated by those skilled in the art that the design of the expression vector depends on such factors as the choice of the host cells and the desired expression levels. CLPP1 can be expressed in bacterial cells such as E. coli, insect cells (using baculovirus expression vectors), yeast cells or mammalian cells. The expression vector can also be transcribed and translated in vitro, for example, by using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Suitable cleavage enzymes include Factor Xa, thrombin and enterokinase. Examples of fusion expression vectors include pGEX (Pharmacia Piscataway, N.J.), pMAL (New England Biolabs, Beverly, Mass.) and pRITS (Pharmacia, Piscataway, N.J.). Purified fusion proteins can be utilized in CLPP1 activity assays, or to generate antibodies specific for CLPP1.

Examples of suitable inducible non-fusion E. coli expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HSLE174(DE3) from a resident prophage harboring a T7 gn1 gene under the transcriptional control of the lacUV 5 promoter.

One strategy to maximize recombinant protein expression in E. coli is to express the protein in host bacteria that have an impaired capacity to proteolytically cleave the recombinant protein. Another strategy is to alter the polynucleotide sequence encoding the protein so that the individual codons for each amino acid are those preferentially utilized in E. coli.

In another embodiment, the CLPP1 expression vector is a yeast expression vector. Examples of yeast expression vectors include pYepSec1, pMFa, pJRY88, pYES2 (Invitrogen Corporation, San Diego, Calif.), and picZ (Invitrogen Corp, San Diego, Calif.).

Alternatively, CLPP1 or its variant can be expressed in insect cells using baculovirus expression vectors. Suitable baculovirus vectors include the pAc series and the pVL series.

In yet another embodiment, CLPP1 or its variant is expressed in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, adenovirus 2, cytomegalovirus and Simian Virus 40.

In another embodiment, the mammalian expression vector contains tissue-specific regulatory elements. Examples of suitable tissue-specific promoters include the liver-specific albumin promoter, lymphoid-specific promoters, promoters of T cell receptors and immunoglobulins, neuron-specific promoters (e.g., the neurofilament promoter), pancreas-specific promoters, and mammary gland-specific promoters (e.g., milk whey promoter). Developmentally-regulated promoters are also contemplated, which include, for example, the α-fetoprotein promoter.

The present invention also provides a recombinant expression vector comprising a polynucleotide which encodes CLPP1 but is cloned into the expression vector in an antisense orientation. Regulatory sequences that are operatively linked to the antisense-oriented polynucleotide can be chosen to direct continuous expression of the antisense RNA molecule in a variety of cell types. Suitable regulatory sequences include viral promoters and/or enhancers. Regulatory sequences can also be chosen to direct constitutive, tissue specific or cell type specific expression of the antisense RNA. The antisense expression vector can be in the form of a recombinant plasmid, phagemid, or attenuated virus in which antisense polynucleotides are produced under the control of a highly efficient regulatory region.

The present invention further provides gene delivery vehicles for delivering polynucleotides to mammals. A polynucleotide sequence of the invention can be administered either locally or systemically via a gene delivery vehicle. Expression of the polynucleotide can be induced using endogenous mammalian or heterologous promoters. Expression of the polynucleotide in vivo can be either constituted or regulated. The gene delivery vehicles preferably are viral vectors, including retroviral, lentiviral, adenoviral, adeno-associated viral (AAV), herpes viral, or alphavirus vectors. The viral vectors can also be astrovirus, coronavirus, orthomyxovirus, papovavirus, paramyxovirus, parvovirus, picornavirus, poxvirus, or togavirus vectors.

Delivery of gene therapy constructs is not limited to the above mentioned viral vectors. Other delivery methods can also be employed. These methods include nucleic acid expression vectors, polycationic condensed DNA linked or unlinked to killed adenovirus, ligand linked DNA, liposome-DNA conjugates, gene guns, ionizing radiation, nucleic charge neutralization, or fusion with cell membranes. Naked DNA can also be employed. Uptake efficiency of the naked DNA may be improved using biodegradable latex beads. This method can be further improved by treating the beads to increase their hydrophobicity.

Regulatable Expression Systems

Another aspect of the present invention pertains to the use of regulatable expression systems to express desirable polynucleotides or polypeptides in cells. Systems suitable for this invention are briefly described below:

Tet-on/off system. The Tet-system is based on two regulatory elements derived from the tetracycline-resistance operon of the *E. coli* Tn10 transposon: the tet repressor protein (TetR) and the Tet operator DNA sequence (tetO) to which TetR binds (Gossen et al., Science 268: 1766–1769, 1995). The system consists of two components, a "regulator" and a "reporter" plasmid. The "regulator" plasmid encodes a hybrid protein containing a mutated Tet repressor (rtetR) fused to the VP16 activation domain of herpes simplex virus. The "reporter" plasmid contains a tet-responsive element (TRE), which controls the "reporter" gene of choice. The rtetR-VP16 fusion protein can only bind to the TRE, therefore activating the transcription of the "reporter" gene in the presence of tetracycline. The system has been incorporated into a number of viral vectors including retrovirus, adenovirus and AAV.

Ecdysone system. The ecdysone system is based on the molting induction system found in *Drosophila*, but modified for inducible expression in mammalian cells. The system uses an analog of the *Drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., Proc. Natl. Acad. Sci. USA 93: 3346–3351, 1996).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., Nat. Biotech 15: 239–243, 1997).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons (Ye et al., Science 283: 88–91, 1999).

Detection Methods

In patients with disorders related to the aberrant expression of CLPP1. The expression level of CLPP1 can be used as an indicator for detecting the presence of CLPP1-related diseases in humans. Detection and measurement of the relative amount of the CLPP1 gene product can be carried out using various methods known in the art.

Typical methodologies for detecting the transcription level of a gene include extracting RNA from a cell or tissue sample, hybridizing a labeled probe to the extracted RNA or derivative thereof (such as cDNA or cRNA), and detecting the probe. Suitable methods include Northern Blot and quantitative RCR or RT-PCR. In situ hybridization can also be used to detect the transcription level of the CLPP1 gene in human tissues.

Typical methodologies for detecting a polypeptide include extracting proteins from a cell or tissue sample, binding an antibody to the target polypeptide and detecting the antibody. Suitable methods include enzyme linked immunosorbent assays (ELISAs), Western blots, immunoprecipitations, and immunofluorescence. The antibody can be polyclonal, or preferably, monoclonal. The antibody can be an intact antibody, or a fragment thereof (e.g. Fab or F(ab')$_2$). The antibody can be labeled with a radioisotope, a fluorescent compound, an enzyme, an enzyme co-factor, or a detectable ligand. The term "labeled," with regard to a probe or antibody, is intended to encompass direct labeling such as through covalent coupling, as well as indirect labeling such as being mediated by another reagent which is directly labeled. Examples of indirect labeling include labeling a primary antibody using a fluorescently labeled secondary antibody, or attaching a DNA probe with a biotin which can be detected, for example, by a fluorescence-labeled streptavidin.

Preferably, the binding affinity of the antibody to CLPP1 is at least $10^5$ M$^{-1}$. More preferably, the binding affinity is at least $10^6$ M$^{-1}$. Other methods such as electrophoresis, chromatography or direct sequencing can also be used to detect the amount of a polypeptide in a biological sample. Anti-CLPP1 antibodies can also be directly introduced into a subject. The antibody can be labeled with a radioactive marker whose presence and location in the subject can be detected using standard imaging techniques.

In one embodiment, the genomic copies of the CLPP1 gene in the genome of a human subject may indicate the presence or predisposition of a disease. Detection of the presence or number of copies of the CLPP1 gene in the genome can be performed using methods known in the art. For instance, it can be assessed using Southern Blot. The probes for Southern Blot can be labeled with a radioisotope, a fluorescent compound, an enzyme, or an enzyme co-factor.

In the field of diagnostic assays, the above-described detection methods can be used to determine the severity of CLPP1-related diseases. A biological sample is isolated from a test subject, and the presence, quantity and/or activity of CLPP1 in the sample relative to a normal or control sample is evaluated. The expression level of CLPP1 in the biological sample can indicate the presence or severity of CLPP1-related diseases in the test subject. The term "biological sample" is intended to include tissues, cells or biological fluids isolated from the subject. A preferred biological sample is a serum sample isolated from the subject using conventional means.

Screening Methods

The present invention also provides methods for identifying CLPP1 modulators. Suitable modulators include compounds or agents comprising therapeutic moieties, such as peptides, peptidomimetics, peptoids, polynucleotides, small molecules or other drugs. These moieties can either bind to CLPP1, or have a modulatory (e.g. stimulatory or inhibitory) effect on the activity of CLPP1. In one embodiment, the moieties have a modulatory effect on the interactions of CLPP1 with one or more of its natural substrates. These moieties can also exert a modulatory effect on the expression of CLPP1. The screen assays of the present invention comprise detecting the interactions between CLPP1 and test components.

The test compounds of the present invention can be either small molecules or bioactive agents. In a preferred embodiment, the test compound is a small organic or inorganic molecule. In another preferred embodiment, the test compound is a polypeptides, oligopeptides, polysaccharides, nucleotides or polynucleotides.

In accordance with one aspect of this invention, methods for screening for compounds that inhibit the biological activities of CLPP1 are provided. Pharmaceutical compositions comprising these compounds can subsequently be prepared. The screening method comprises (1) contacting a sample with a compound, and (2) comparing expression profile or biological activity of CLPP1 in the sample to determine whether the compound substantially decreases the expression level or activities of CLPP1. The screening method can be carried out either in vivo or in vitro.

The present invention further includes a method for screening for compounds capable of modulating the binding between CLPP1 and a binding partner. As used herein, the term "binding partner" refers to a bioactive agent which serves as either a substrate for CLPP1, or a ligand having a binding affinity to CLPP1. The bioactive agent may be selected from a variety of naturally-occurring or synthetic compounds, proteins, peptides, polysaccharides, nucleotides or polynucleotides.

Inhibitors of the expression, activity or binding ability of CLPP1 may be used as therapeutic compositions. These inhibitors can be formulated in suitable pharmaceutical compositions, as described herein below.

The present invention also provides methods for conducting high-throughput screening for compounds capable of inhibiting activity or expression of CLPP1. In one embodiment, the high-throughput screening method involves contacting test compounds with CLPP1, and then detecting the effect of the test compounds on CLPP1. Functional assays, such as cytosensor microphysiometer-based assays, calcium flux assays (e.g. FLIPR®, Molecular Devices Corp, Sunnyvale, Calif.), or the TUNEL assay, can be employed to measure CLPP1 cellular activity. Fluorescence-based techniques can be used for high-throughput and ultra high-throughput screening. They include, but are not limited to, BRET® and FRET® (both by Packard Instrument Co., Meriden, Conn.).

In a preferred embodiment, the high-throughput screening assay uses label-free plasmon resonance technology as provided by BIACORE® systems (Biacore International AB, Uppsala, Sweden). Plasmon free resonance occurs when surface plasmon waves are excited at a metal/liquid interface. By reflecting directed light from the surface as a result of contact with a sample, the surface plasmon resonance causes a change in the refractive index at the surface layer. The refractive index change for a given change of mass concentration at the surface layer is similar for many bioactive agents (including proteins, peptides, lipids and polynucleotides), and since the BIACORE® sensor surface can be functionalized to bind a variety of these bioactive agents, detection of a wide selection of test compounds can thus be accomplished.

Monitoring Efficay of a Drug during Clinical Trials

Using the CLPP1 detection methods of this invention, the efficacy of a therapeutic agent for CLPP1-related diseases can be monitored during clinical trials. The therapeutic agent may be a drug, small molecule, agonist, antagonist, peptidomimetic, protein, peptide, or polynucleotide. The changes in the expression or activity of the CLPP1 gene in response to the treatment of the agent can be used to evaluate the therapeutic effect of the agent on patients with CLPP1-related diseases. In addition, the expression or activity of CLPP1 in response to the agent can be measured at various points during the clinical trial.

In a preferred embodiment, the method for monitoring the effectiveness of the therapeutic agent includes the steps of (i) obtaining a pre-administration sample from a subject; (ii) detecting the level of expression or activity of CLPP1 in the pre-administration sample; (iii) obtaining one or more post-administration samples from the subject; (iv) detecting the level of expression or activity of CLPP1 in the post-administration samples; (v) comparing the level of expression or activity of CLPP1 in the pre-administration sample to the level of expression or activity of CLPP1 in the post administration samples. The dose or frequency of the administration of the agent may be adjusted based on the effectiveness of the agent in a particular patient. Therefore, CLPP1 expression or activity can be used as an indicator of the effectiveness of a therapeutic agent for CLPP1-related diseases, even if the agent does not produce an observable phenotypic response.

Prognostic Assays

The detection methods described herein can be used to identify subjects having or at risk of developing CLPP1-related diseases. In addition, the detection methods can be used to determine whether an agent (e.g., an agonist, antagonist, peptidomimetic, protein, peptide, polynucleotide, small molecule, or other drug candidate) can be administered to a subject for effectively treating or preventing CLPP1-related diseases.

CLPP1 expression profiles at different progression stages of CLPP1-related diseases can be established. In addition, CLPP1 expression profiles in different patients who have different responses to a drug treatment are determined. A pattern may emerge such that a particular expression profile may be correlated to an increased likelihood of a poor prognosis. Therefore, the prognostic assay of the present invention may be used to determine whether a subject undergoing a treatment for a CLPP1-related disease has a poor outlook for long term survival or disease progression. Preferably, prognosis is performed shortly after diagnosis, such as within a few days after diagnosis. The result of prognosis can then be used to devise individualized treatment program, thereby enhancing the effectiveness of the treatment as well as the likelihood of long-term survival and well being.

The method of the invention can also be used to detect genetic alterations in the CLPP1 gene, thereby determining if a subject with the altered gene is at risk for damages characterized by aberrant regulation in CLPP1 activity or expression. In a preferred embodiment, the method includes detecting the presence or absence of a genetic alteration that affects the integrity of the CLPP1 gene, or detecting the aberrant expression of the CLPP1 gene. The genetic alteration can be detected by ascertaining the existence of at least one of the following: 1) deletion of one or more nucleotides from the CLPP1 gene; 2) addition of one or more nucleotides to the CLPP1 gene; 3) substitution of one or more nucleotides of the CLPP1 gene, 4) a chromosomal rearrangement in the CLPP1 gene; 5) alteration in the level of a messenger RNA transcript of the CLPP1 gene, 6) aberrant modification of the CLPP1 gene, 7) the presence of a non-wild type splicing pattern of a messenger RNA transcript of the CLPP1 gene, 8) non-wild type level CLPP1, 9) allelic loss of a CLPP1 gene, and 10) inappropriate post-translational modification of CLPP1.

In one embodiment, detection of the alteration involves the use of a probe/primer in a polymerase chain reaction (such as anchor PCR or RACE PCR) or alternatively, in a ligation chain reaction (LCR). LCR can be particularly useful for detecting point mutations in the CLPP1 gene. This method includes the steps of collecting a sample from a subject, isolating polynucleotides (e.g., genomic DNA, mRNA, or both) from the sample, contacting the polynucleotide with one or more primers which specifically hybridize to the CLPP1 gene or gene product, and detecting the presence or absence of an amplification product, or detecting the size of the amplification product and comparing its length to a control. It is understood that PCR and/or LCR can be used as a preliminary amplification step in conjunction with any other techniques described herein.

Alternative amplification methods include: self sustained sequence replication (Guatelli et al., Proc. Natl. Acad. Sci. USA 87:1874–1878, 1990), transcriptional amplification system (Kwoh et al., Proc. Natl. Acad. Sci. USA 86:1173–1177, 1989), and Q-Beta Replicase (Lizardi, et al., Bio-Technology 6:1197, 1988).

In another embodiment, mutations in the CLPP1 gene can be identified using restriction enzymes. Differences in restriction enzyme digestion patterns indicates mutation(s) in the CLPP1 gene or its transcripts. Moreover, sequence specific ribozymes can be used to detect the presence of specific mutations. See, for example, U.S. Pat. No. 5,498,531.

In yet another embodiment, genetic mutations in the CLPP1 gene can be identified using high density arrays which contain a large number of oligonucleotides probes. For example, genetic mutations in the CLPP1 gene can be identified in two dimensional arrays. In this example, a first hybridization array of probes is used to scan through long stretches of DNA in a sample and a control in order to identify base changes between the two sequences. This step allows the identification of point mutations. This step is followed by a second hybridization array that allows the characterization of specific mutations by using smaller and specialized probe arrays which are complementary to all variants or mutations detected. Each mutation array is composed of parallel probe sets, one complementary to the wild-type gene and the other complementary to the mutant gene.

In still another embodiment, any sequencing reactions known in the art can be used to directly sequence the CLPP1 gene in order to detect mutations. It is contemplated that any automated sequencing procedures can be utilized, including sequencing by mass spectrometry.

In one embodiment, protection from cleavage agents is used to detect mismatched bases in RNA/RNA or RNA/DNA heteroduplexes. In general, the "mismatch cleavage" technique involves forming heteroduplexes by hybridizing a RNA or DNA (labeled) containing the wild-type CLPP1 gene sequence to a potentially mutant RNA or DNA obtained from a tissue sample. The double-stranded duplexes are treated with an agent which cleaves single-stranded regions of the duplex. The agent may be RNase (for RNA/DNA duplexes), or S1 nuclease (for DNA/DNA hybrids). In one case, either DNA/DNA or RNA/DNA duplexes are treated with piperidine and hydroxylamine, or piperidine and osmium tetroxide, in order to digest mismatched regions. After the digestion, the resulting material is separated by size on a denaturing polyacrylamide gel from which the site(s) of mutation may be determined.

In a preferred embodiment, the mismatch cleavage reaction employs one or more proteins that recognize mismatched base pairs in double-stranded DNA. Examples of these proteins include "DNA mismatch repair" enzymes. For instance, the mutY enzyme of *E. coli* cleaves A at G/A mismatches, and the thymidine DNA glycosylase from HeLa cells cleaves T at G/T mismatches. In one case, cDNAs are prepared from mRNAs isolated from test cells. The cDNAs are then hybridized to a probe derived from the CLPP1 gene. The duplex thus formed is treated with a DNA mismatch repair enzyme, and the cleavage products, if any, can be detected from electrophoresis protocols or the like. See e.g., U.S. Pat. No. 5,459,039.

In another embodiment, alterations in electrophoretic mobility are used to identify mutations in the CLPP1 gene. Differences in electrophoretic mobility between mutant and wild type polynucleotides can be detected using single strand conformation polymorphism (SSCP). The resulting alteration in electrophoretic mobility enables the detection of a single base change. The DNA fragments can be labeled or detected with probes. In one case, the sensitivity of the assay is enhanced by using RNA, in which the secondary structure is more sensitive to a change in sequence. In a preferred embodiment, the assay utilizes heteroduplex analysis to separate double stranded heteroduplex molecules on the basis of changes in electrophoretic mobility (Keen et al., Trends Genet 7:5, 1991).

In yet another embodiment, the movement of mutant or wild-type fragments is evaluated using denaturing gradient gel electrophoresis (DGGE). For this purpose, DNA fragments can be modified to insure that they do not completely denature. For instance, a GC clamp of approximately 40 GC-rich base pairs can be added to the DNA fragment using PCR. In a further embodiment, a temperature gradient is used in place of a denaturing gradient (Rosenbaum and Reissner Biophys, Chem 265:12753, 1987).

Examples of other techniques for detecting point mutations include, but are not limited to, selective oligonucleotide hybridization, selective amplification, or selective primer extension. In one embodiment, oligonucleotide primers for specific amplification carry the mutation of interest in the center of the molecule (so that amplification depends on differential hybridization) or at the extreme 3' end of one primer where, under appropriate conditions, mismatch can prevent or reduce polymerase extension. See e.g., Saiki et al., Proc. Natl. Acad. Sci. USA 86:6230, 1989. In addition, it may be desirable to introduce a novel restriction site in the region of the mutation to create cleavage-based detection.

The methods described herein can be performed using prepackaged diagnostic kits which comprise at least one polynucleotide probe or one antibody of the present invention. These kits can be used in clinical settings to diagnose subjects exhibiting symptoms or family history of a CLPP1-related disease. Any cell type or tissue in which CLPP1 is expressed can be used for prognostic or diagnostic purposes.

Prophylactic Methods

This invention also provides methods for preventing diseases associated with aberrant CLPP1 expression or activity. The methods comprise administering to a target subject an agent which modulates CLPP1 expression or activity.

Subjects at risk of diseases which are caused by or attributed to aberrant CLPP1 expression or activity can be identified using the diagnostic or prognostic assays described herein. A prophylactic agent can be administered prior to the manifestation of CLPP1-related disease symptoms in order to prevent or delay CLPP1-related diseases. Suitable prophylactic agents include mutant CLPP1 proteins, CLPP1 antagonist agents, or CLPP1 antisense polynucleotides.

The prophylactic methods of this invention can be specifically tailored or modified, based on knowledge obtained from the study of pharmacogenomics. Pharmacogenomics includes the application of genomics technologies, such as gene sequencing, statistical genetics, and gene expression analysis, to drugs which are either in clinical development or on the market. Pharmacogenomics can be used to determine a subject's response to a drug (e.g., a subject's "drug response phenotype" or "drug response genotype"). Thus, another aspect of this invention is to provide methods for tailoring an individual's prophylactic or therapeutic treatment using CLPP1 modulators according to the individual's drug response genotype. Pharmacogenomics allows a clinician or physician to target prophylactic or therapeutic treatments to subjects who will most benefit from the treatment and to avoid treatment of subjects who will experience toxic drug-related side effects.

One pharmacogenomics approach to identify genes that predict drug response, known as "a genome-wide association," relies primarily on a high-resolution map of the human genome consisting of already known gene-related sites (e.g., a "bi-allelic" gene marker map which consists of 60,000–100,000 polymorphic or variable sites on the human genome, each of which has two variants). Such a high-resolution genetic map can be compared to a map of the genome of each of a statistically substantial number of subjects taking part in a Phase II/III drug trial in order to identify genes associated with a particular observed drug response or side effect. Alternatively, such a high resolution map can be generated from a combination of some ten-million known single nucleotide polymorphisms (SNPS) in the human genome. A "SNP" is a common alteration that occurs in a single nucleotide base in a stretch of DNA. For example, a SNP may occur once per every 1000 bases of DNA. A SNP may be involved in a disease process. However, the vast majority of SNPs may be not related to diseases. Given a genetic map based on the occurrence of SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the CLPP1 gene to SNP maps of patients with CLPP1-related diseases may facilitate the identification of drug-response-prediction genes.

Alternatively, the "candidate gene approach" can be utilized to identify genes that predict drug response. According to this method, if a gene that encodes a drug target is known, all common variants of that gene can be easily identified in the population. It then can be determined if a particular drug response is associated with one version of the gene versus another.

The activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYPZC19) has provided an explanation as to why some subjects do not obtain the expected drug effects or show exaggerated drug response and serious toxicity after taking the standard and safe dose of a drug. These polymorphisms are expressed in two phenotypes in the population, extensive metabolizer and poor metabolizer. The prevalence of poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response. The other extreme are the so called ultra-rapid metabolizers who do not respond to standard doses. Recently, the molecular basis of ultra-rapid metabolism has been identified to be due to CYP2D6 gene amplification.

In one embodiment, the "gene expression profiling" method can be utilized to identify genes that predict drug response. In this regard, the gene expression profile of an animal dosed with a drug can give an indication of whether the gene pathways related to toxicity have been turned on.

Information generated from the above pharmacogenomics approaches can be used to determine the appropriate dosage or treatment regimen suitable for a particular individual. This knowledge can avoid adverse reactions or therapeutic failure, and therefore enhance therapeutic or prophylactic efficiency when treating a subject with an CLPP1 modulator.

Therapeutic Methods

As described above, the present invention includes therapeutic methods for treating a subject at risk for, susceptible to, or diagnosed with CLPP1-related diseases. The therapeutic methods can be individually tailored based on the subject's drug, response genotype. Typically, the therapeutic methods comprise modulating the expression or activity of CLPP1 in the subject. In one embodiment, the method comprises contacting a plurality of cells in the subject with an agent that inhibits the expression or activity of CLPP1. Suitable agents include polynucleotides (e.g., an antisense oligonucleotides of CLPP1), polypeptides (e.g., a dominant negative mutant of CLPP1), or polysaccharides, naturally-occurring target molecules of CLPP1 protein (e.g., an CLPP1 protein substrate or receptor), anti-CLPP1 antibodies, CLPP1 antagonists, or other small organic and inorganic molecule. They may also include vectors comprising polynucleotides encoding CLPP1 inhibitors or antisense sequences. Moreover, the agents can be anti-CLPP1 antibodies conjugated with therapeutic moieties. Suitable agents can be identified using the screening assays of the present invention.

Pharmaceutical Compositions

The present invention is further directed to pharmaceutical compositions comprising an CLPP1 modulator and a pharmaceutically acceptable carrier. As used herein, a "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active modulator (e.g., an anti-CLPP1 antibody, an CLPP1 activity inhibitor, or a gene therapy vector expressing antisense nucleotide to CLPP1) in the required amount in an appropriate solvent, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Kits

The invention also encompasses kits for detecting the presence of a CLPP1 gene product in a biological sample. An example kit comprises reagents for assessing expression of CLPP1 at mRNA or protein level. Preferably, the reagents include an antibody or fragment thereof, wherein the antibody or fragment specifically binds to CLPP1. Optionally, the kits may comprise a polynucleotide probe capable of specifically binding to a transcript of the CLPP1 gene. The kit may also contain means for determining the amount of CLPP1 protein or mRNA in the test sample, and/or means for comparing the amount of CLPP1 protein or mRNA in the test sample to a control or standard. The compound or agent can be packaged in a suitable container.

The invention further provides kits for assessing the suitability of each of a plurality of compounds for inhibiting CLPP1-related diseases in cells or human subjects. Such kits include a plurality of compounds to be tested, and a reagent (such as an antibody specific to CLPP1 proteins, or a polynucleotide probe or primer capable of hybridizing to the CLPP1 gene) for assessing expression of CLPP1.

It should be understood that the above-described embodiments are given by way illustration, not limitation. Various changes and modifications within the spirit and scope of the present invention will become apparent to those skilled in the art from the present description.

Host Cells

Another aspect of the invention pertains to host cells into which a polynucleotide molecule of the invention is introduced, e.g., a CLPP1 gene or homolog thereof, within an expression vector, a gene delivery vector, or a polynucleotide molecule of the invention containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CLPP1 gene can be expressed in bacterial cells such as *E. coli*, insect cells, yeast or mammalian cells (such as Chinese hamster ovary cells (CHO), COS cells, Fischer 344 rat cells, HLA-B27 rat cells, HeLa cells, A549 cells, or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DAKD-dextran-mediated transfection, lipofection, or electroporation.

For stable transfection of mammalian cells, it is known that, depending upon the expression vector and transfection technique used, only a small fraction of cells may integrate the foreign DNA into their genome. In order to identify and select these integrants, a gene that encodes a selectable flag (e.g., resistance to antibiotics) is generally introduced into the host cells along with the gene of interest. Preferred selectable flags include those which confer resistance to drugs, such as G418, hygromycin and methotrexate. Polynucleotides encoding a selectable flag can be introduced into a host cell by the same vector as that encoding CLPP1 or can be introduced by a separate vector. Cells stably transfected with the introduced polynucleotide can be identified by drug selection (e.g., cells that have incorporated the selectable flag gene will survive, while the other cells die).

A host cell of the invention, such as a prokaryotic or eukaryotic host cell in culture, can be used to produce (i.e., express) CLPP1. Accordingly, the invention further provides methods for producing CLPP1 using the host cells of the invention. In one embodiment, the method comprises culturing the host cell of invention (into which a recombinant expression vector containing a CLPP1 gene has been introduced) in a suitable medium such that CLPP1 is produced. In another embodiment, the method further comprises isolating CLPP1 from the medium or the host cell.

Transgenic and Knockout Animals

The host cells of the invention can also be used to produce non-human transgenic animals. For example, in one embodiment, a host cell of the invention is a fertilized oocyte or an embryonic stem cell into which CLPP1-coding sequences have been introduced. Such host cells can then be used to create non-human transgenic animals in which exogenous sequences encoding CLPP1 have been introduced into their genome or homologous recombinant animals in which endogenous sequences encoding CLPP1 have been altered. Such animals are useful for studying the function and/or activity of CLPP1 and for identifying and/or evaluating modulators of CLPP1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" or "knockout animal" is a non-human animal, preferably a mammal, more preferably a mouse, in which an endogenous CLPP1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing an CLPP1-encoding polynucleotide into the mate pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of CLPP1 to particular cells. Methods for generating transgenic animals via embryo manipulation and microinjection, particularly animals such as mice, have become conventional in the art. Similar methods are used for production of other transgenic animals. A transgenic founder animal can be identified based upon the presence of a transgene of the invention in its genome and/or expression of mRNA corresponding to a gene of the invention in tissues or cells of the animals. A transgenic founder animal can then be used to breed additional animals carrying the transgene. Moreover, transgenic animals carrying a transgene encoding CLPP1 can further be bred to other transgenic animals carrying other transgenes.

To create a homologous recombinant animal (knockout animal), a vector is prepared which contains at least a portion of a gene of the invention into which a deletion, addition or substitution has been introduced to thereby alter, e.g., functionally disrupt, the gene. The gene can be a human gene, but more preferably, is a non-human homolog of a human gene of the invention (e.g., a homolog of the CLPP1 gene). For example, a mouse gene can be used to construct a homologous recombination polynucleotide molecule, e.g., a vector, suitable for altering an endogenous gene of the invention in the mouse genome. In a preferred embodiment, the homologous recombination polynucleotide molecule is designed such that, upon homologous recombination, the endogenous gene of the invention is functionally disrupted (i.e., no longer encodes a functional protein; also referred to as a "knockout" vector). Alternatively, the homologous recombination polynucleotide molecule can be designed such that, upon homologous recombination, the endogenous gene is mutated or otherwise altered but still encodes functional protein (e.g., the upstream regulatory region can be altered to thereby alter the expression of the endogenous CLPP1 gene). In the homologous recombination polynucleotide molecule, the altered portion of the gene of the invention is flanked at its 5' and 3' ends by additional polynucleotide sequence of the gene of the invention to allow for homologous recombination to occur between the exogenous gene carried by the homologous recombination polynucleotide molecule and an endogenous gene in a cell, e.g., an embryonic stem cell. The additional flanking polynucleotide sequence is of sufficient length for successful homologous recombination with the endogenous gene. Typically, several kilobases of flanking DNA (both at the 5' and 3' ends) are included in the homologous recombination polynucleotide molecule. The homologous recombination polynucleotide molecule is introduced into embryonic stem cells by electroporation. The cells in which the introduced gene has homologously recombined with the endogenous gene are selected. The selected cells can then be injected into a blastocyst of an animal (e.g., a mouse) to form aggregation chimeras. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the homologously recombined DNA. Methods for constructing homologous recombination polynucleotide molecules, e.g., vectors, or homologous recombinant animals are well known in the art.

In another embodiment, transgenic non-human animals can be produced which contain selected systems which allow for regulated expression of the transgene. One example of such a system is the cre/loxP recombinase system of bacteriophage Pl . Another example of a recombinase system is the FLP recombinase system of *Saccharomyces cerevisiae* (see e.g., O'Gorman et al., Science 251: 1351–1355, 1991). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al., Nature 385:810–813, 1997, and PCT International Publication Nos. WO97/07668 and WO97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

EXAMPLES

Example 1

Identification of CLPP1 Sequence in Human Genome Database

The nucleic acid sequence of CLPP1 is obtained from a newly developed genomic prediction pipeline. Briefly, the X-ray crystal structures of the catalytic domains of protein phosphatase were collected and aligned together according to their structural identity/similarities. The alignment was converted into a "scoring matrix" which carried the structural profile of the phosphatase catalytic domains. This scoring matrix was then used to search the Celera Human Genome database for sequences that have phosphatase catalytic domains.

Example 2

BLAST Analysis

Sequence alignments between CLPP1 and other sequences in GenBank database were performed using the standard protein-protein BLAST(blastp), standard nucleotide-nucleotide BLAST(blastn), BLAST2 Sequences, and human genome BLAST programs that are available at NCBI's BLAST website.

A standard protein-protein BLAST search in the "nr" database (available at NCBI's BLAST website) with "Filter" setting unchecked, "Expect" setting at 10.0, "Word Size" setting at 3, "Matrix" setting at BLOSUM62, "Gap costs" setting at Existence:11 and Extension:1, revealed that CCPP1 is identical to a hypothetical human protein LOC159669 (Entrez accession number: XM100270), which was predicted from NCBI contig NT024115 by automated computational analysis using gene prediction method GenomeScan. In addition, CLPP1 also share sequence homologies to a number of proteins, including but are not limited to, Bacteriophage lambda ser/thr protein phosphatase (Entrez accession number: P03772, 75% alignment to amino acid residues 55–242 of CLPP1), *E. coli* ser/thr protein phosphatase (Entrez accession number: NC002695, 74% alignment to amino acid residues 55–242 of CLPP1), an unknown protein encoded by prophage CP-933K (Entrez accession number: AE005256, 72% alignment to amino acid residues 102–242 of CLPP1), *E. coli* phosphoprotein phosphatase 1 (Entrez accession number: AP002559, 47% alignment to amino acid residues 60–239 of CLPP1), and *S. typhimurium* protein phosphatase B (Entrez accession number: AY049951, 42% alignment to amino acid residues 43–239 of CLPP1).

A domain search was performed within the standard protein-protein BLAST search with the RPS-BLAST 2.2.3 [Apr. 24, 2002] program. The amino acid residues 47 to 211 of CLPP1 are highly homologous to the consensus sequence of the calcineurin-like phosphoesterase family (pfam00149). This family includes a diverse range of phosphoesterases, including protein phosphoserine phosphatases, nucleotidases, sphingomyelin phosphodiesterases and 2'-3' cAMP phosphodiesterases as well as nucleases such as bacterial SbcD or yeast MRE11. The most conserved regions in this family centre around the metal chelating residues.

A standard nucleotide-nucleotide BLAST search in the "pat" database (available at NCBI's BLAST website) with "Filter" setting unchecked, "Expect" setting at 10.0, "Word Size" setting at 3, identified significant alignment of CLPP1 nucleotide sequence to a fragment of Sequence 29 from PCT patent application WO99/27132 (Entrez accession number: A95298, 99% alignment to nucleotides 771–1326 of CLPP1), and a fragment of Sequence 14 from PCT patent application WO02/24924 (Entrez accession number: AX406967, 100% alignment to nucleotides 168–708 of CLPP1).

A human genome search was carried out using blastn program with Expect setting at 0.01, Filter setting at default, Descriptions setting at 100, and Alignment settings at 100. The CLPP1 gene was mapped to or near locus 10p15 of human chromosome 10. Specifically, CLPP1 gene is located between genes LOC119379 and LOC159671, and overlaps with gene LOC159669.

Human CLPP1 gene has 4 exons. The exons are mapped to nucleotides 4200965 to 4203759 in human chromosome 10 of the Entrez Human Genome Sequence Database maintained by NCBI. The relative location of the exons in the genomic sequence is listed in Table 2.

Example 3

Hydrophobicity Analysis

The hydrophobicity profile of CLPP1 sequence (FIG. 2) was generated using the GES (Goldman, Engelman and Steitz) hydrophobicity scale (Engelman et al., Ann. Rev. Biophys. Biophys. Chem. 15:321–353, 1986.) Briefly, the GES scale is used to identify nonpolar transbilayer helices. The curve is the average of a residue-specific hydrophobicity scale over a window of 20 residues. When the line is in the upper half of the frame (positive), it indicates a hydrophobic region and when it is in the lower half (negative), a hydrophilic region.

In FIG. 2, the X-axis represents the length of the protein in amino acids (aa), while the Y-axis represents the GES score. The curve line shows the GES pattern of the entire protein, while the strait line represents certain cutoff for potential membrane spanning domains. The hydrophobicity profile indicates that CLPP1 is probably not a membrane protein.

Having described preferred embodiments of compositions, organisms and methodologies employing a novel human gene CLPP1 (which are intended to be illustrative and not limiting), it is noted that modifications and variations can be made by persons skilled in the art in light of the above teachings. Therefore, it is understood that changes may be made in the particular embodiments disclosed which are within the scope of what is described as defined by the appended claims.

SEQUENCE LISTING

<160> NUMBER OF SEQ ID NOS: 303

<210> SEQ ID NO 1
<211> LENGTH: 1326
<212> TYPE: DNA
<213> ORGANISM: Homo sapiens

<400> SEQUENCE: 1

```
atgcccctc gcgccccggc ctcggcgccc gctcccggct ccagcgcgcc tgcacgttac      60
cgtttaggcc tgtccgtgtt cgtgcgtggc ataggcacgc tggctctacc tggtaggcgg    120
ctacgcgaca ctcggtctga tctagcgctc ggactagact ggctgacaaa ggtttcgttc    180
gaccctgcgt gtgatttgct gatttcggtt ggagaccttg ttgaccgcgg cgcggaaaac    240
gtcgagtgcc tggagctgat tactatgcct tggttccggg ctgtgcgagg taaccatgag    300
cagatgatga ttgatgggct atcggagtat ggaaacgtta accactggct ggaaaacggc    360
ggcgtgtggt tcttcagtct tgattatgaa aaagaggtgc tggctaaggc tctggttcat    420
aaaatcggcca gcctgccatt cgtcatcgag ctggttaccg ctgaacgtaa aatcgttatc    480
tgccacgctg actacccgca taacgaatat gcgttcgaca gccggtcccc gaaagacatg    540
gtcatctgga tcgtgaacg ggttagcgac gctcaggacg gcattgtctc gccgatagct    600
ggtgctgatc tgtttatctt cggccacacc cctgcgcgcc agcccctgaa gtatgccaac    660
cagatgtaca tcgatactgg tgccgtgttc tgcggaaacc tcacgctgtg caaagtatgc    720
ggtgaatact tcgtgccgaa attccacgac atccggatcc ggtggtgcag cccggagcat    780
ggcgcaatcc tcgcaatgga agaacgcaag aaggacaacg tgaaagccgc ggctaagcgc    840
atcaaggagc aaaaagaggc tgaaaaggac gggcgcaaac gccgcaagga gcggctggca    900
gagctcaggc cagacggata ctacaaggct caggctcaga aagctttcaa cgcctttatc    960
cgtgcgcgcg acgccgattt gccatgcatc agctgcggcg agaccaatcc gcctgatctg   1020
catggtggcc agtgggattg cggccatttc aagacagtag gtgcttaccc tgaactgcgc   1080
tttgaagaac gcaacgccca taagcagtgc aaatcctgta atgccggagc tggcaagtac   1140
accgccaaag aggcgaccgt ggcgcagcaa tacgaagctg ggttggtcgc tcgttacggt   1200
cagggatacg tcaactggct caatggtccc cacgaaatga ccaactaccg ccgtgaagac   1260
ttcatccgga tccgggatga gtaccgcgac aagctcaaag cactgaaaca gcgggaggca   1320
gcatga                                                              1326
```

<210> SEQ ID NO 2
<211> LENGTH: 441
<212> TYPE: PRT
<213> ORGANISM: Homo sapiens

<400> SEQUENCE: 2

```
Met Pro Pro Arg Ala Pro Ala Ser Ala Pro Ala Gly Ser Ser Ala
1               5                   10                  15

Pro Ala Arg Tyr Arg Leu Gly Leu Ser Val Phe Val Arg Gly Ile Gly
            20                  25                  30

Thr Leu Ala Leu Pro Gly Arg Arg Leu Arg Asp Thr Arg Ser Asp Leu
        35                  40                  45

Ala Leu Gly Leu Asp Trp Leu Thr Lys Val Ser Phe Asp Pro Ala Cys
    50                  55                  60

Asp Leu Leu Ile Ser Val Gly Asp Leu Val Asp Arg Gly Ala Glu Asn
```

```
                65                  70                  75                  80
        Val Glu Cys Leu Glu Leu Ile Thr Met Pro Trp Phe Arg Ala Val Arg
                        85                  90                  95

Gly Asn His Glu Gln Met Met Ile Asp Gly Leu Ser Glu Tyr Gly Asn
                100                 105                 110

Val Asn His Trp Leu Glu Asn Gly Gly Val Trp Phe Ser Leu Asp
                115                 120                 125

Tyr Glu Lys Glu Val Leu Ala Lys Ala Leu Val His Lys Ser Ala Ser
                130                 135                 140

Leu Pro Phe Val Ile Glu Leu Val Thr Ala Glu Arg Lys Ile Val Ile
        145                 150                 155                 160

Cys His Ala Asp Tyr Pro His Asn Glu Tyr Ala Phe Asp Lys Pro Val
                        165                 170                 175

Pro Lys Asp Met Val Ile Trp Asn Arg Glu Arg Val Ser Asp Ala Gln
                        180                 185                 190

Asp Gly Ile Val Ser Pro Ile Ala Gly Ala Asp Leu Phe Ile Phe Gly
                        195                 200                 205

His Thr Pro Ala Arg Gln Pro Leu Lys Tyr Ala Asn Gln Met Tyr Ile
                210                 215                 220

Asp Thr Gly Ala Val Phe Cys Gly Asn Leu Thr Leu Cys Lys Val Cys
        225                 230                 235                 240

Gly Glu Tyr Phe Val Pro Lys Phe His Asp Ile Arg Ile Arg Trp Cys
                        245                 250                 255

Ser Pro Glu His Gly Ala Ile Leu Ala Met Glu Glu Arg Lys Lys Asp
                        260                 265                 270

Asn Val Lys Ala Ala Lys Arg Ile Lys Glu Gln Lys Glu Ala Glu
                275                 280                 285

Lys Asp Gly Arg Lys Arg Lys Glu Arg Leu Ala Glu Leu Arg Pro
        290                 295                 300

Asp Gly Tyr Tyr Lys Ala Gln Ala Gln Lys Ala Phe Asn Ala Phe Ile
        305                 310                 315                 320

Arg Ala Arg Asp Ala Asp Leu Pro Cys Ile Ser Cys Gly Glu Thr Asn
                        325                 330                 335

Pro Pro Asp Leu His Gly Gly Gln Trp Asp Cys Gly His Phe Lys Thr
                        340                 345                 350

Val Gly Ala Tyr Pro Glu Leu Arg Phe Glu Glu Arg Asn Ala His Lys
                        355                 360                 365

Gln Cys Lys Ser Cys Asn Ala Gly Ala Gly Lys Tyr Thr Ala Lys Glu
                        370                 375                 380

Ala Thr Val Ala Gln Gln Tyr Glu Ala Gly Leu Val Ala Arg Tyr Gly
        385                 390                 395                 400

Gln Gly Tyr Val Asn Trp Leu Asn Gly Pro His Glu Met Thr Asn Tyr
                        405                 410                 415

Arg Arg Glu Asp Phe Ile Arg Ile Arg Asp Glu Tyr Arg Asp Lys Leu
                        420                 425                 430

Lys Ala Leu Lys Gln Arg Glu Ala Ala
                435                 440

<210> SEQ ID NO 3
<211> LENGTH: 2795
<212> TYPE: DNA
<213> ORGANISM: Homo sapiens
<220> FEATURE:
<221> NAME/KEY: misc_feature
<222> LOCATION: (1478)..(1577)
```

<223> OTHER INFORMATION: N = A, T, C or G

<400> SEQUENCE: 3

| | | | | |
|---|---|---|---|---|
| atgcccctc | gcgccccggc | ctcggcgccc | gctcccggct | ccagcgcgcc tgcacgtacg | 60 |
| tagccttcac | gtgtgtgtgg | atacggagtg | catgtgtgga | gacagaggaa tatgctccaa | 120 |
| caaatttcgg | atagaggcgc | cgaagacagg | acgtggggaa | ggtaggagcc gcgtgcacgg | 180 |
| ctccggcccc | gggcgggagg | cggccgcgag | ccgggccggc | cgcgcgcaag tccggcgcca | 240 |
| gccgctagag | cccccagtgc | gcggcccggc | cgcggggcgc | ctcgacccga cacaataaac | 300 |
| tccgagggcg | ggcgggccga | ggggccggtg | gggccgatcg | gtcgcccccgc gcgcatcgcc | 360 |
| atgtgagcgg | ttgccgcggc | ttctcgggga | cccaactttc | ccgggcggcg gcgcccaact | 420 |
| tcccgccgcc | cgctccggcc | ccgtaggccc | gcggcgccag | gggaagacgc gagtaagtgc | 480 |
| gggcggcggt | gccctcccgg | ccctcacccc | gcacgcggcg | acctcggccg cctagctctc | 540 |
| ccttcgctca | tggcgcgacc | gctggcgtct | ctctgcaggt | ggagctctta caaatcatgg | 600 |
| tcgcccctcg | agacccggat | gcccttcgc | tgcggagacc | ggcgtgcggt gtgtccggag | 660 |
| cgggtgggga | tgacggggat | tggtagggta | gagtaggctc | tggccagtgg atgacgtgat | 720 |
| gtgattgctg | gctttgtagt | cgtctcactc | tctttccctc | ctctcgtctc cgttcttcac | 780 |
| tgcatcaggt | taccgtttag | gcctgtccgt | gttcgtgcgt | ggcataggca cgctggctct | 840 |
| acctggtagg | cggctacgcg | acactcggtc | tgatctagcg | ctcggactag actggctggt | 900 |
| accggagtca | cctgcattct | atatttggtt | gcgggcaata | tgtctcgtta ctccttctac | 960 |
| tgtctgtgtc | gtttttcctg | tgtcctcatt | gcacccttt | ctatgagctc tcttttcttc | 1020 |
| ctcactacat | ggcttacatc | ttaataccat | gccagcctct | acctcgtcat actctctaac | 1080 |
| tctactatgt | aatatacgaa | tactgagcaa | tatatcctac | tgtccggact caagctccag | 1140 |
| cgcgatctcc | gtgataatcc | ctccatacat | gacaactaca | ccgtactcca tctattaaca | 1200 |
| cctcgtctac | cctcattta | gtttttgtca | gtcaccctct | cagtcaccta tcaccactcc | 1260 |
| atcccacacc | ctcccgtcct | cttaccctgc | ccgtcatac | ctcaccctct ccccaccaac | 1320 |
| tcccctttctc | accgctcgc | tccccctccc | ccccactcaa | ctcttccgtc ctccgtctgt | 1380 |
| ccccaccgtc | acccctctcc | attctcccta | cttcacccta | tacctcctgc attcctctcc | 1440 |
| ccctctatac | tcactcacca | cgatgctacg | aactactnnn | nnnnnnnnn nnnnnnnnn | 1500 |
| nnnnnnnnn | nnnnnnnnn | nnnnnnnnn | nnnnnnnnn | nnnnnnnnn nnnnnnnnn | 1560 |
| nnnnnnnnn | nnnnnnccg | tggtgaagac | aaaggtttcg | ttcgaccctg cgtgtgattt | 1620 |
| gctgatttcg | gttggagacc | ttgttgaccg | cggcgcggaa | aacgtcgagt gcctggagct | 1680 |
| gattactatg | ccttggttcc | gggctgtgcg | aggtaaccat | gagcagatga tgattgatgg | 1740 |
| gctatcggag | tatggaaacg | ttaaccactg | gctggaaaac | ggcggcgtgt ggttcttcag | 1800 |
| tcttgattat | gaaaagagg | tgctggctaa | ggctctggtt | cataaatcgg ccagcctgcc | 1860 |
| attcgtcatc | gagctggtta | ccgctgaacg | taaaatcgtt | atctgccacg ctgactaccc | 1920 |
| gcataacgaa | tatgcgttcg | acaagccggt | cccgaaagac | atggtcatct ggaatcgtga | 1980 |
| acgggttagc | gacgctcagg | acggcattgt | ctcgccgata | gctggtgctg atctgtttat | 2040 |
| cttcggccac | acccctgcgc | gccagcccct | gaagtatgcc | aaccagatgt acatcgatac | 2100 |
| tggtgccgtg | ttctgcggaa | acctcacgct | ggtacaggtt | caaggtggtg cccatgcgta | 2160 |
| aaccatcccg | ccgtaagtgc | aaagtatgcg | gtgaatactt | cgtgccgaaa ttccacgaca | 2220 |
| tccggatccg | gtggtgcagc | ccggagcatg | gcgcaatcct | cgcaatggaa gaacgcaaga | 2280 |

```
aggacaacgt gaaagccgcg gctaagcgca tcaaggagca aaaagaggct gaaaaggacg    2340
ggcgcaaacg ccgcaaggag cggctggcag agctcaggcc agacggatac tacaaggctc    2400
aggctcagaa agctttcaac gcctttatcc gtgcgcgcga cgccgatttg ccatgcatca    2460
gctgcggcga gaccaatccg cctgatctgc atggtggcca gtgggattgc ggccatttca    2520
agacagtagg tgcttaccct gaactgcgct ttgaagaacg caacgcccat aagcagtgca    2580
aatcctgtaa tgccggagct ggcaagtaca ccgccaaaga ggcgaccgtg gcgcagcaat    2640
acgaagctgg gttggtcgct cgttacggtc agggatacgt caactggctc aatggtcccc    2700
acgaaatgac caactaccgc cgtgaagact tcatccggat ccgggatgag taccgcgaca    2760
agctcaaagc actgaaacag cgggaggcag catga                               2795
```

<210> SEQ ID NO 4
<211> LENGTH: 21
<212> TYPE: DNA
<213> ORGANISM: Homo sapiens

<400> SEQUENCE: 4
aaccatgagc agatgatgat t                                              21

<210> SEQ ID NO 5
<211> LENGTH: 21
<212> TYPE: RNA
<213> ORGANISM: Homo sapiens

<400> SEQUENCE: 5
ccaugagcag augaugauuu u                                              21

<210> SEQ ID NO 6
<211> LENGTH: 21
<212> TYPE: RNA
<213> ORGANISM: Homo sapiens

<400> SEQUENCE: 6
uugguacucg ucuacuacua a                                              21

<210> SEQ ID NO 7
<211> LENGTH: 21
<212> TYPE: DNA
<213> ORGANISM: Homo sapiens

<400> SEQUENCE: 7
aaacgttaac cactggctgg a                                              21

<210> SEQ ID NO 8
<211> LENGTH: 21
<212> TYPE: RNA
<213> ORGANISM: Homo sapiens

<400> SEQUENCE: 8
acguuaacca cuggcuggau u                                              21

<210> SEQ ID NO 9
<211> LENGTH: 21
<212> TYPE: RNA
<213> ORGANISM: Homo sapiens

<400> SEQUENCE: 9
uuugcaauug gugaccgacc u                                              21

```
<210> SEQ ID NO 10
<211> LENGTH: 21
<212> TYPE: DNA
<213> ORGANISM: Homo sapiens

<400> SEQUENCE: 10
aacgttaacc actggctgga a                                              21

<210> SEQ ID NO 11
<211> LENGTH: 21
<212> TYPE: RNA
<213> ORGANISM: Homo sapiens

<400> SEQUENCE: 11
cguuaaccac uggcuggaau u                                              21

<210> SEQ ID NO 12
<211> LENGTH: 21
<212> TYPE: RNA
<213> ORGANISM: Homo sapiens

<400> SEQUENCE: 12
uugcaauugg ugaccgaccu u                                              21

<210> SEQ ID NO 13
<211> LENGTH: 21
<212> TYPE: DNA
<213> ORGANISM: Homo sapiens

<400> SEQUENCE: 13
aaggctctgg ttcataaatc g                                              21

<210> SEQ ID NO 14
<211> LENGTH: 21
<212> TYPE: RNA
<213> ORGANISM: Homo sapiens

<400> SEQUENCE: 14
ggcucugguu cauaaaucgu u                                              21

<210> SEQ ID NO 15
<211> LENGTH: 21
<212> TYPE: RNA
<213> ORGANISM: Homo sapiens

<400> SEQUENCE: 15
uuccgagacc aaguauuuag c                                              21

<210> SEQ ID NO 16
<211> LENGTH: 21
<212> TYPE: DNA
<213> ORGANISM: Homo sapiens

<400> SEQUENCE: 16
aaatcgttat ctgccacgct g                                              21

<210> SEQ ID NO 17
<211> LENGTH: 21
<212> TYPE: RNA
<213> ORGANISM: Homo sapiens

<400> SEQUENCE: 17
aucguuaucu gccacgcugu u                                              21
```

```
<210> SEQ ID NO 18
<211> LENGTH: 21
<212> TYPE: RNA
<213> ORGANISM: Homo sapiens

<400> SEQUENCE: 18
uuuagcaaua gacggugcga c                                              21

<210> SEQ ID NO 19
<211> LENGTH: 21
<212> TYPE: DNA
<213> ORGANISM: Homo sapiens

<400> SEQUENCE: 19
aatcgttatc tgccacgctg a                                              21

<210> SEQ ID NO 20
<211> LENGTH: 21
<212> TYPE: RNA
<213> ORGANISM: Homo sapiens

<400> SEQUENCE: 20
ucguuaucug ccacgcugau u                                              21

<210> SEQ ID NO 21
<211> LENGTH: 21
<212> TYPE: RNA
<213> ORGANISM: Homo sapiens

<400> SEQUENCE: 21
uuagcaauag acggugcgac u                                              21

<210> SEQ ID NO 22
<211> LENGTH: 21
<212> TYPE: DNA
<213> ORGANISM: Homo sapiens

<400> SEQUENCE: 22
aacgaatatg cgttcgacaa g                                              21

<210> SEQ ID NO 23
<211> LENGTH: 21
<212> TYPE: RNA
<213> ORGANISM: Homo sapiens

<400> SEQUENCE: 23
cgaauaugcg uucgacaagu u                                              21

<210> SEQ ID NO 24
<211> LENGTH: 21
<212> TYPE: RNA
<213> ORGANISM: Homo sapiens

<400> SEQUENCE: 24
uugcuuauac gcaagcuguu c                                              21

<210> SEQ ID NO 25
<211> LENGTH: 21
<212> TYPE: DNA
<213> ORGANISM: Homo sapiens

<400> SEQUENCE: 25
```

```
aaagacatgg tcatctggaa t                                           21

<210> SEQ ID NO 26
<211> LENGTH: 21
<212> TYPE: RNA
<213> ORGANISM: Homo sapiens

<400> SEQUENCE: 26
agacaugguc aucuggaauu u                                           21

<210> SEQ ID NO 27
<211> LENGTH: 21
<212> TYPE: RNA
<213> ORGANISM: Homo sapiens

<400> SEQUENCE: 27
uuucuguacc aguagaccuu a                                           21

<210> SEQ ID NO 28
<211> LENGTH: 21
<212> TYPE: DNA
<213> ORGANISM: Homo sapiens

<400> SEQUENCE: 28
aagacatggt catctggaat c                                           21

<210> SEQ ID NO 29
<211> LENGTH: 21
<212> TYPE: RNA
<213> ORGANISM: Homo sapiens

<400> SEQUENCE: 29
gacaugguca ucuggaaucu u                                           21

<210> SEQ ID NO 30
<211> LENGTH: 21
<212> TYPE: RNA
<213> ORGANISM: Homo sapiens

<400> SEQUENCE: 30
uucuguacca guagaccuua g                                           21

<210> SEQ ID NO 31
<211> LENGTH: 21
<212> TYPE: DNA
<213> ORGANISM: Homo sapiens

<400> SEQUENCE: 31
aagtatgcca accagatgta c                                           21

<210> SEQ ID NO 32
<211> LENGTH: 21
<212> TYPE: RNA
<213> ORGANISM: Homo sapiens

<400> SEQUENCE: 32
guaugccaac cagauguacu u                                           21

<210> SEQ ID NO 33
<211> LENGTH: 21
<212> TYPE: RNA
<213> ORGANISM: Homo sapiens

<400> SEQUENCE: 33
```

-continued uucauacggu uggcuacau g                                    21

<210> SEQ ID NO 34
<211> LENGTH: 21
<212> TYPE: DNA
<213> ORGANISM: Homo sapiens

<400> SEQUENCE: 34
aaccagatgt acatcgatac t                                   21

<210> SEQ ID NO 35
<211> LENGTH: 21
<212> TYPE: RNA
<213> ORGANISM: Homo sapiens

<400> SEQUENCE: 35
ccagauguac aucgauacuu u                                   21

<210> SEQ ID NO 36
<211> LENGTH: 21
<212> TYPE: RNA
<213> ORGANISM: Homo sapiens

<400> SEQUENCE: 36 uuggcuaca uguagcuaug a                                    21

<210> SEQ ID NO 37
<211> LENGTH: 21
<212> TYPE: DNA
<213> ORGANISM: Homo sapiens

<400> SEQUENCE: 37
aaacctcacg ctgtgcaaag t                                   21

<210> SEQ ID NO 38
<211> LENGTH: 21
<212> TYPE: RNA
<213> ORGANISM: Homo sapiens

<400> SEQUENCE: 38
accucacgcu gugcaaaguu u                                   21

<210> SEQ ID NO 39
<211> LENGTH: 21
<212> TYPE: RNA
<213> ORGANISM: Homo sapiens

<400> SEQUENCE: 39
uuuggagugc gacacguuuc a                                   21

<210> SEQ ID NO 40
<211> LENGTH: 21
<212> TYPE: DNA
<213> ORGANISM: Homo sapiens

<400> SEQUENCE: 40
aacctcacgc tgtgcaaagt a                                   21

<210> SEQ ID NO 41
<211> LENGTH: 21
<212> TYPE: RNA
<213> ORGANISM: Homo sapiens

```
<400> SEQUENCE: 41
ccucacgcug ugcaaaguau u                                              21

<210> SEQ ID NO 42
<211> LENGTH: 21
<212> TYPE: RNA
<213> ORGANISM: Homo sapiens

<400> SEQUENCE: 42
uuggagugcg acacguuuca u                                              21

<210> SEQ ID NO 43
<211> LENGTH: 21
<212> TYPE: DNA
<213> ORGANISM: Homo sapiens

<400> SEQUENCE: 43
aaagtatgcg gtgaatactt c                                              21

<210> SEQ ID NO 44
<211> LENGTH: 21
<212> TYPE: RNA
<213> ORGANISM: Homo sapiens

<400> SEQUENCE: 44
aguaugcggu gaauacuucu u                                              21

<210> SEQ ID NO 45
<211> LENGTH: 21
<212> TYPE: RNA
<213> ORGANISM: Homo sapiens

<400> SEQUENCE: 45
uuucauacgc cacuuaugaa g                                              21

<210> SEQ ID NO 46
<211> LENGTH: 21
<212> TYPE: DNA
<213> ORGANISM: Homo sapiens

<400> SEQUENCE: 46
aagtatgcgg tgaatacttc g                                              21

<210> SEQ ID NO 47
<211> LENGTH: 21
<212> TYPE: RNA
<213> ORGANISM: Homo sapiens

<400> SEQUENCE: 47
guaugcggug aauacuucgu u                                              21

<210> SEQ ID NO 48
<211> LENGTH: 21
<212> TYPE: RNA
<213> ORGANISM: Homo sapiens

<400> SEQUENCE: 48
uucauacgcc acuuaugaag c                                              21

<210> SEQ ID NO 49
<211> LENGTH: 21
<212> TYPE: DNA
<213> ORGANISM: Homo sapiens
```

-continued

<400> SEQUENCE: 49
aatacttcgt gccgaaattc c                                              21

<210> SEQ ID NO 50
<211> LENGTH: 21
<212> TYPE: RNA
<213> ORGANISM: Homo sapiens

<400> SEQUENCE: 50
uacuucgugc cgaaauuccu u                                              21

<210> SEQ ID NO 51
<211> LENGTH: 21
<212> TYPE: RNA
<213> ORGANISM: Homo sapiens

<400> SEQUENCE: 51
uuaugaagca cggcuuuaag g                                              21

<210> SEQ ID NO 52
<211> LENGTH: 21
<212> TYPE: DNA
<213> ORGANISM: Homo sapiens

<400> SEQUENCE: 52
aaattccacg acatccggat c                                              21

<210> SEQ ID NO 53
<211> LENGTH: 21
<212> TYPE: RNA
<213> ORGANISM: Homo sapiens

<400> SEQUENCE: 53
auuccacgac auccggaucu u                                              21

<210> SEQ ID NO 54
<211> LENGTH: 21
<212> TYPE: RNA
<213> ORGANISM: Homo sapiens

<400> SEQUENCE: 54
uuuaaggugc uguaggccua g                                              21

<210> SEQ ID NO 55
<211> LENGTH: 21
<212> TYPE: DNA
<213> ORGANISM: Homo sapiens

<400> SEQUENCE: 55
aatcctcgca atggaagaac g                                              21

<210> SEQ ID NO 56
<211> LENGTH: 21
<212> TYPE: RNA
<213> ORGANISM: Homo sapiens

<400> SEQUENCE: 56
uccucgcaau ggaagaacgu u                                              21

<210> SEQ ID NO 57
<211> LENGTH: 21
<212> TYPE: RNA

<213> ORGANISM: Homo sapiens

<400> SEQUENCE: 57
uuaggagcgu uaccuucuug c                                              21

<210> SEQ ID NO 58
<211> LENGTH: 21
<212> TYPE: DNA
<213> ORGANISM: Homo sapiens

<400> SEQUENCE: 58
aatggaagaa cgcaagaagg a                                              21

<210> SEQ ID NO 59
<211> LENGTH: 21
<212> TYPE: RNA
<213> ORGANISM: Homo sapiens

<400> SEQUENCE: 59
uggaagaacg caagaaggau u                                              21

<210> SEQ ID NO 60
<211> LENGTH: 21
<212> TYPE: RNA
<213> ORGANISM: Homo sapiens

<400> SEQUENCE: 60
uuaccuucuu gcguucuucc u                                              21

<210> SEQ ID NO 61
<211> LENGTH: 21
<212> TYPE: DNA
<213> ORGANISM: Homo sapiens

<400> SEQUENCE: 61
aagaacgcaa gaaggacaac g                                              21

<210> SEQ ID NO 62
<211> LENGTH: 21
<212> TYPE: RNA
<213> ORGANISM: Homo sapiens

<400> SEQUENCE: 62
gaacgcaaga aggacaacgu u                                              21

<210> SEQ ID NO 63
<211> LENGTH: 21
<212> TYPE: RNA
<213> ORGANISM: Homo sapiens

<400> SEQUENCE: 63
uucuugcguu cuccuguug c                                               21

<210> SEQ ID NO 64
<211> LENGTH: 21
<212> TYPE: DNA
<213> ORGANISM: Homo sapiens

<400> SEQUENCE: 64
aacgcaagaa ggacaacgtg a                                              21

<210> SEQ ID NO 65
<211> LENGTH: 21

```
<212> TYPE: RNA
<213> ORGANISM: Homo sapiens

<400> SEQUENCE: 65
cgcaagaagg acaacgugau u                                              21

<210> SEQ ID NO 66
<211> LENGTH: 21
<212> TYPE: RNA
<213> ORGANISM: Homo sapiens

<400> SEQUENCE: 66
uugcguucuu ccuguugcac u                                              21

<210> SEQ ID NO 67
<211> LENGTH: 21
<212> TYPE: DNA
<213> ORGANISM: Homo sapiens

<400> SEQUENCE: 67
aagaaggaca acgtgaaagc c                                              21

<210> SEQ ID NO 68
<211> LENGTH: 21
<212> TYPE: RNA
<213> ORGANISM: Homo sapiens

<400> SEQUENCE: 68
gaaggacaac gugaaagccu u                                              21

<210> SEQ ID NO 69
<211> LENGTH: 21
<212> TYPE: RNA
<213> ORGANISM: Homo sapiens

<400> SEQUENCE: 69
uucuuccugu ugcacuuucg g                                              21

<210> SEQ ID NO 70
<211> LENGTH: 21
<212> TYPE: DNA
<213> ORGANISM: Homo sapiens

<400> SEQUENCE: 70
aaagctttca acgcctttat c                                              21

<210> SEQ ID NO 71
<211> LENGTH: 21
<212> TYPE: RNA
<213> ORGANISM: Homo sapiens

<400> SEQUENCE: 71
agcuuucaac gccuuuaucu u                                              21

<210> SEQ ID NO 72
<211> LENGTH: 21
<212> TYPE: RNA
<213> ORGANISM: Homo sapiens

<400> SEQUENCE: 72
uuucgaaagu ugcggaaaua g                                              21

<210> SEQ ID NO 73
```

-continued

```
<211> LENGTH: 21
<212> TYPE: DNA
<213> ORGANISM: Homo sapiens

<400> SEQUENCE: 73
aagctttcaa cgcctttatc c                                              21

<210> SEQ ID NO 74
<211> LENGTH: 21
<212> TYPE: RNA
<213> ORGANISM: Homo sapiens

<400> SEQUENCE: 74 gcuucaacg ccuuuauccu u                                               21

<210> SEQ ID NO 75
<211> LENGTH: 21
<212> TYPE: RNA
<213> ORGANISM: Homo sapiens

<400> SEQUENCE: 75
uucgaaaguu gcggaaauag g                                              21

<210> SEQ ID NO 76
<211> LENGTH: 21
<212> TYPE: DNA
<213> ORGANISM: Homo sapiens

<400> SEQUENCE: 76
aactgcgctt tgaagaacgc a                                              21

<210> SEQ ID NO 77
<211> LENGTH: 21
<212> TYPE: RNA
<213> ORGANISM: Homo sapiens

<400> SEQUENCE: 77
cugcgcuuug aagaacgcau u                                              21

<210> SEQ ID NO 78
<211> LENGTH: 21
<212> TYPE: RNA
<213> ORGANISM: Homo sapiens

<400> SEQUENCE: 78
uugacgcgaa acuucuugcg u                                              21

<210> SEQ ID NO 79
<211> LENGTH: 21
<212> TYPE: DNA
<213> ORGANISM: Homo sapiens

<400> SEQUENCE: 79
aagcagtgca aatcctgtaa t                                              21

<210> SEQ ID NO 80
<211> LENGTH: 21
<212> TYPE: RNA
<213> ORGANISM: Homo sapiens

<400> SEQUENCE: 80
gcagugcaaa uccuguaauu u                                              21
```

```
<210> SEQ ID NO 81
<211> LENGTH: 21
<212> TYPE: RNA
<213> ORGANISM: Homo sapiens

<400> SEQUENCE: 81
uucgucacgu uuaggacauu a                                              21

<210> SEQ ID NO 82
<211> LENGTH: 21
<212> TYPE: DNA
<213> ORGANISM: Homo sapiens

<400> SEQUENCE: 82
aaatcctgta atgccggagc t                                              21

<210> SEQ ID NO 83
<211> LENGTH: 21
<212> TYPE: RNA
<213> ORGANISM: Homo sapiens

<400> SEQUENCE: 83
auccuguaau gccggagcuu u                                              21

<210> SEQ ID NO 84
<211> LENGTH: 21
<212> TYPE: RNA
<213> ORGANISM: Homo sapiens

<400> SEQUENCE: 84
uuuaggacau uacggccucg a                                              21

<210> SEQ ID NO 85
<211> LENGTH: 21
<212> TYPE: DNA
<213> ORGANISM: Homo sapiens

<400> SEQUENCE: 85
catgagcaga tgatgattga t                                              21

<210> SEQ ID NO 86
<211> LENGTH: 21
<212> TYPE: RNA
<213> ORGANISM: Homo sapiens

<400> SEQUENCE: 86
ugagcagaug augauugauu u                                              21

<210> SEQ ID NO 87
<211> LENGTH: 21
<212> TYPE: RNA
<213> ORGANISM: Homo sapiens

<400> SEQUENCE: 87
uuacucgucu acuacuaacu a                                              21

<210> SEQ ID NO 88
<211> LENGTH: 21
<212> TYPE: DNA
<213> ORGANISM: Homo sapiens

<400> SEQUENCE: 88
cattcgtcat cgagctggtt a                                              21
```

```
<210> SEQ ID NO 89
<211> LENGTH: 21
<212> TYPE: RNA
<213> ORGANISM: Homo sapiens

<400> SEQUENCE: 89
uucgucaucg agcugguuau u                                              21

<210> SEQ ID NO 90
<211> LENGTH: 21
<212> TYPE: RNA
<213> ORGANISM: Homo sapiens

<400> SEQUENCE: 90
uuaagcagua gcucgaccaa u                                              21

<210> SEQ ID NO 91
<211> LENGTH: 21
<212> TYPE: DNA
<213> ORGANISM: Homo sapiens

<400> SEQUENCE: 91
cataacgaat atgcgttcga c                                              21

<210> SEQ ID NO 92
<211> LENGTH: 21
<212> TYPE: RNA
<213> ORGANISM: Homo sapiens

<400> SEQUENCE: 92
uaacgaauau gcguucgacu u                                              21

<210> SEQ ID NO 93
<211> LENGTH: 21
<212> TYPE: RNA
<213> ORGANISM: Homo sapiens

<400> SEQUENCE: 93
uuauugcuua uacgcaagcu g                                              21

<210> SEQ ID NO 94
<211> LENGTH: 21
<212> TYPE: DNA
<213> ORGANISM: Homo sapiens

<400> SEQUENCE: 94
catggtcatc tggaatcgtg a                                              21

<210> SEQ ID NO 95
<211> LENGTH: 21
<212> TYPE: RNA
<213> ORGANISM: Homo sapiens

<400> SEQUENCE: 95
uggucaucug gaaucgugau u                                              21

<210> SEQ ID NO 96
<211> LENGTH: 21
<212> TYPE: RNA
<213> ORGANISM: Homo sapiens

<400> SEQUENCE: 96
uuaccaguag accuuagcac u                                              21
```

<210> SEQ ID NO 97
<211> LENGTH: 21
<212> TYPE: DNA
<213> ORGANISM: Homo sapiens

<400> SEQUENCE: 97
caaccagatg tacatcgata c                                    21

<210> SEQ ID NO 98
<211> LENGTH: 21
<212> TYPE: RNA
<213> ORGANISM: Homo sapiens

<400> SEQUENCE: 98
accagaugua caucgauacu u                                    21

<210> SEQ ID NO 99
<211> LENGTH: 21
<212> TYPE: RNA
<213> ORGANISM: Homo sapiens

<400> SEQUENCE: 99
uuuggucuac auguagcuau g                                    21

<210> SEQ ID NO 100
<211> LENGTH: 21
<212> TYPE: DNA
<213> ORGANISM: Homo sapiens

<400> SEQUENCE: 100
cagatgtaca tcgatactgg t                                    21

<210> SEQ ID NO 101
<211> LENGTH: 21
<212> TYPE: RNA
<213> ORGANISM: Homo sapiens

<400> SEQUENCE: 101
gauguacauc gauacugguu u                                    21

<210> SEQ ID NO 102
<211> LENGTH: 21
<212> TYPE: RNA
<213> ORGANISM: Homo sapiens

<400> SEQUENCE: 102
uucuacaugu agcuaugacc a                                    21

<210> SEQ ID NO 103
<211> LENGTH: 21
<212> TYPE: DNA
<213> ORGANISM: Homo sapiens

<400> SEQUENCE: 103
catcgatact ggtgccgtgt t                                    21

<210> SEQ ID NO 104
<211> LENGTH: 21
<212> TYPE: RNA
<213> ORGANISM: Homo sapiens

<400> SEQUENCE: 104
ucgauacugg ugccguguuu u                           21

<210> SEQ ID NO 105
<211> LENGTH: 21
<212> TYPE: RNA
<213> ORGANISM: Homo sapiens

<400> SEQUENCE: 105
uuagcuauga ccacggcaca a                           21

<210> SEQ ID NO 106
<211> LENGTH: 21
<212> TYPE: DNA
<213> ORGANISM: Homo sapiens

<400> SEQUENCE: 106
caaagtatgc ggtgaatact t                           21

<210> SEQ ID NO 107
<211> LENGTH: 21
<212> TYPE: RNA
<213> ORGANISM: Homo sapiens

<400> SEQUENCE: 107
aaguaugcgg ugaauacuuu u                           21

<210> SEQ ID NO 108
<211> LENGTH: 21
<212> TYPE: RNA
<213> ORGANISM: Homo sapiens

<400> SEQUENCE: 108
uuuucauacg ccacuuauga a                           21

<210> SEQ ID NO 109
<211> LENGTH: 21
<212> TYPE: DNA
<213> ORGANISM: Homo sapiens

<400> SEQUENCE: 109
caatcctcgc aatggaagaa c                           21

<210> SEQ ID NO 110
<211> LENGTH: 21
<212> TYPE: RNA
<213> ORGANISM: Homo sapiens

<400> SEQUENCE: 110
auccucgcaa uggaagaacu u                           21

<210> SEQ ID NO 111
<211> LENGTH: 21
<212> TYPE: RNA
<213> ORGANISM: Homo sapiens

<400> SEQUENCE: 111
uuuaggagcg uuaccuucuu g                           21

<210> SEQ ID NO 112
<211> LENGTH: 21
<212> TYPE: DNA
<213> ORGANISM: Homo sapiens

<400> SEQUENCE: 112

```
caatggaaga acgcaagaag g                                              21

<210> SEQ ID NO 113
<211> LENGTH: 21
<212> TYPE: RNA
<213> ORGANISM: Homo sapiens

<400> SEQUENCE: 113
auggaagaac gcaagaaggu u                                              21

<210> SEQ ID NO 114
<211> LENGTH: 21
<212> TYPE: RNA
<213> ORGANISM: Homo sapiens

<400> SEQUENCE: 114
uuuaccuucu ugcguucuuc c                                              21

<210> SEQ ID NO 115
<211> LENGTH: 21
<212> TYPE: DNA
<213> ORGANISM: Homo sapiens

<400> SEQUENCE: 115
caagaaggac aacgtgaaag c                                              21

<210> SEQ ID NO 116
<211> LENGTH: 21
<212> TYPE: RNA
<213> ORGANISM: Homo sapiens

<400> SEQUENCE: 116
agaaggacaa cgugaaagcu u                                              21

<210> SEQ ID NO 117
<211> LENGTH: 21
<212> TYPE: RNA
<213> ORGANISM: Homo sapiens

<400> SEQUENCE: 117
uuucuuccug uugcacuuuc g                                              21

<210> SEQ ID NO 118
<211> LENGTH: 21
<212> TYPE: DNA
<213> ORGANISM: Homo sapiens

<400> SEQUENCE: 118
caggccagac ggatactaca a                                              21

<210> SEQ ID NO 119
<211> LENGTH: 21
<212> TYPE: RNA
<213> ORGANISM: Homo sapiens

<400> SEQUENCE: 119
ggccagacgg auacuacaau u                                              21

<210> SEQ ID NO 120
<211> LENGTH: 21
<212> TYPE: RNA
<213> ORGANISM: Homo sapiens
```

-continued

```
<400> SEQUENCE: 120
uuccggucug ccuaugaugu u                                              21

<210> SEQ ID NO 121
<211> LENGTH: 21
<212> TYPE: DNA
<213> ORGANISM: Homo sapiens

<400> SEQUENCE: 121
cagacggata ctacaaggct c                                              21

<210> SEQ ID NO 122
<211> LENGTH: 21
<212> TYPE: RNA
<213> ORGANISM: Homo sapiens

<400> SEQUENCE: 122
gacggauacu acaaggcucu u                                              21

<210> SEQ ID NO 123
<211> LENGTH: 21
<212> TYPE: RNA
<213> ORGANISM: Homo sapiens

<400> SEQUENCE: 123
uucugccuau gauguuccga g                                              21

<210> SEQ ID NO 124
<211> LENGTH: 21
<212> TYPE: DNA
<213> ORGANISM: Homo sapiens

<400> SEQUENCE: 124
caggctcaga aagctttcaa c                                              21

<210> SEQ ID NO 125
<211> LENGTH: 21
<212> TYPE: RNA
<213> ORGANISM: Homo sapiens

<400> SEQUENCE: 125
ggcucagaaa gcuuucaacu u                                              21

<210> SEQ ID NO 126
<211> LENGTH: 21
<212> TYPE: RNA
<213> ORGANISM: Homo sapiens

<400> SEQUENCE: 126
uuccgagucu uucgaaaguu g                                              21

<210> SEQ ID NO 127
<211> LENGTH: 21
<212> TYPE: DNA
<213> ORGANISM: Homo sapiens

<400> SEQUENCE: 127
cagaaagctt tcaacgcctt t                                              21

<210> SEQ ID NO 128
<211> LENGTH: 21
<212> TYPE: RNA
<213> ORGANISM: Homo sapiens
```

-continued

<400> SEQUENCE: 128
gaaagcuuuc aacgccuuuu u                                              21

<210> SEQ ID NO 129
<211> LENGTH: 21
<212> TYPE: RNA
<213> ORGANISM: Homo sapiens

<400> SEQUENCE: 129
uucuuucgaa aguugcggaa a                                              21

<210> SEQ ID NO 130
<211> LENGTH: 21
<212> TYPE: DNA
<213> ORGANISM: Homo sapiens

<400> SEQUENCE: 130
catttcaaga cagtaggtgc t                                              21

<210> SEQ ID NO 131
<211> LENGTH: 21
<212> TYPE: RNA
<213> ORGANISM: Homo sapiens

<400> SEQUENCE: 131
uuucaagaca guaggugcuu u                                              21

<210> SEQ ID NO 132
<211> LENGTH: 21
<212> TYPE: RNA
<213> ORGANISM: Homo sapiens

<400> SEQUENCE: 132
uuaaaguucu gucauccacg a                                              21

<210> SEQ ID NO 133
<211> LENGTH: 21
<212> TYPE: DNA
<213> ORGANISM: Homo sapiens

<400> SEQUENCE: 133
cataagcagt gcaaatcctg t                                              21

<210> SEQ ID NO 134
<211> LENGTH: 21
<212> TYPE: RNA
<213> ORGANISM: Homo sapiens

<400> SEQUENCE: 134
uaagcagugc aaauccuguu u                                              21

<210> SEQ ID NO 135
<211> LENGTH: 21
<212> TYPE: RNA
<213> ORGANISM: Homo sapiens

<400> SEQUENCE: 135
uuauucguca cguuuaggac a                                              21

<210> SEQ ID NO 136
<211> LENGTH: 21
<212> TYPE: DNA

<213> ORGANISM: Homo sapiens

<400> SEQUENCE: 136
cagtgcaaat cctgtaatgc c                                              21

<210> SEQ ID NO 137
<211> LENGTH: 21
<212> TYPE: RNA
<213> ORGANISM: Homo sapiens

<400> SEQUENCE: 137
gugcaaaucc uguaaugccu u                                              21

<210> SEQ ID NO 138
<211> LENGTH: 21
<212> TYPE: RNA
<213> ORGANISM: Homo sapiens

<400> SEQUENCE: 138
uucacguuua ggacauuacg g                                              21

<210> SEQ ID NO 139
<211> LENGTH: 21
<212> TYPE: DNA
<213> ORGANISM: Homo sapiens

<400> SEQUENCE: 139
caaatcctgt aatgccggag c                                              21

<210> SEQ ID NO 140
<211> LENGTH: 21
<212> TYPE: RNA
<213> ORGANISM: Homo sapiens

<400> SEQUENCE: 140
aauccuguaa ugccggagcu u                                              21

<210> SEQ ID NO 141
<211> LENGTH: 21
<212> TYPE: RNA
<213> ORGANISM: Homo sapiens

<400> SEQUENCE: 141
uuuuaggaca uuacggccuc g                                              21

<210> SEQ ID NO 142
<211> LENGTH: 21
<212> TYPE: DNA
<213> ORGANISM: Homo sapiens

<400> SEQUENCE: 142
cacgaaatga ccaactaccg c                                              21

<210> SEQ ID NO 143
<211> LENGTH: 21
<212> TYPE: RNA
<213> ORGANISM: Homo sapiens

<400> SEQUENCE: 143
cgaaaugacc aacuaccgcu u                                              21

<210> SEQ ID NO 144
<211> LENGTH: 21

```
<212> TYPE: RNA
<213> ORGANISM: Homo sapiens

<400> SEQUENCE: 144
uugcuuuacu gguugauggc g                                              21

<210> SEQ ID NO 145
<211> LENGTH: 21
<212> TYPE: DNA
<213> ORGANISM: Homo sapiens

<400> SEQUENCE: 145
gactagactg gctgacaaag g                                              21

<210> SEQ ID NO 146
<211> LENGTH: 21
<212> TYPE: RNA
<213> ORGANISM: Homo sapiens

<400> SEQUENCE: 146
cuagacuggc ugacaaaggu u                                              21

<210> SEQ ID NO 147
<211> LENGTH: 21
<212> TYPE: RNA
<213> ORGANISM: Homo sapiens

<400> SEQUENCE: 147
uugaucugac cgacuguuuc c                                              21

<210> SEQ ID NO 148
<211> LENGTH: 21
<212> TYPE: DNA
<213> ORGANISM: Homo sapiens

<400> SEQUENCE: 148
gactggctga caaaggtttc g                                              21

<210> SEQ ID NO 149
<211> LENGTH: 21
<212> TYPE: RNA
<213> ORGANISM: Homo sapiens

<400> SEQUENCE: 149
cuggcugaca aagguuucgu u                                              21

<210> SEQ ID NO 150
<211> LENGTH: 21
<212> TYPE: RNA
<213> ORGANISM: Homo sapiens

<400> SEQUENCE: 150
uugaccgacu guuccaaag c                                               21

<210> SEQ ID NO 151
<211> LENGTH: 21
<212> TYPE: DNA
<213> ORGANISM: Homo sapiens

<400> SEQUENCE: 151
gatttgctga tttcggttgg a                                              21

<210> SEQ ID NO 152
```

-continued

```
<211> LENGTH: 21
<212> TYPE: RNA
<213> ORGANISM: Homo sapiens

<400> SEQUENCE: 152
uuugcugauu ucgguuggau u                                              21

<210> SEQ ID NO 153
<211> LENGTH: 21
<212> TYPE: RNA
<213> ORGANISM: Homo sapiens

<400> SEQUENCE: 153
uuaaacgacu aaagccaacc u                                              21

<210> SEQ ID NO 154
<211> LENGTH: 21
<212> TYPE: DNA
<213> ORGANISM: Homo sapiens

<400> SEQUENCE: 154
gatttcggtt ggagaccttg t                                              21

<210> SEQ ID NO 155
<211> LENGTH: 21
<212> TYPE: RNA
<213> ORGANISM: Homo sapiens

<400> SEQUENCE: 155
uuucgguugg agaccuuguu u                                              21

<210> SEQ ID NO 156
<211> LENGTH: 21
<212> TYPE: RNA
<213> ORGANISM: Homo sapiens

<400> SEQUENCE: 156
uuaaagccaa ccucuggaac a                                              21

<210> SEQ ID NO 157
<211> LENGTH: 21
<212> TYPE: DNA
<213> ORGANISM: Homo sapiens

<400> SEQUENCE: 157
gagtgcctgg agctgattac t                                              21

<210> SEQ ID NO 158
<211> LENGTH: 21
<212> TYPE: RNA
<213> ORGANISM: Homo sapiens

<400> SEQUENCE: 158
gugccuggag cugauuacuu u                                              21

<210> SEQ ID NO 159
<211> LENGTH: 21
<212> TYPE: RNA
<213> ORGANISM: Homo sapiens

<400> SEQUENCE: 159
uucacggacc ucgacuaaug a                                              21
```

```
<210> SEQ ID NO 160
<211> LENGTH: 21
<212> TYPE: DNA
<213> ORGANISM: Homo sapiens

<400> SEQUENCE: 160
gagctgatta ctatgccttg g                                        21

<210> SEQ ID NO 161
<211> LENGTH: 21
<212> TYPE: RNA
<213> ORGANISM: Homo sapiens

<400> SEQUENCE: 161
gcugauuacu augccuuggu u                                        21

<210> SEQ ID NO 162
<211> LENGTH: 21
<212> TYPE: RNA
<213> ORGANISM: Homo sapiens

<400> SEQUENCE: 162
uucgacuaau gauacggaac c                                        21

<210> SEQ ID NO 163
<211> LENGTH: 21
<212> TYPE: DNA
<213> ORGANISM: Homo sapiens

<400> SEQUENCE: 163
gattactatg ccttggttcc g                                        21

<210> SEQ ID NO 164
<211> LENGTH: 21
<212> TYPE: RNA
<213> ORGANISM: Homo sapiens

<400> SEQUENCE: 164
uuacuaugcc uugguuccgu u                                        21

<210> SEQ ID NO 165
<211> LENGTH: 21
<212> TYPE: RNA
<213> ORGANISM: Homo sapiens

<400> SEQUENCE: 165
uuaaugauac ggaaccaagg c                                        21

<210> SEQ ID NO 166
<211> LENGTH: 21
<212> TYPE: DNA
<213> ORGANISM: Homo sapiens

<400> SEQUENCE: 166
gaggtaacca tgagcagatg a                                        21

<210> SEQ ID NO 167
<211> LENGTH: 21
<212> TYPE: RNA
<213> ORGANISM: Homo sapiens

<400> SEQUENCE: 167
gguaaccaug agcagaugau u                                        21
```

```
<210> SEQ ID NO 168
<211> LENGTH: 21
<212> TYPE: RNA
<213> ORGANISM: Homo sapiens

<400> SEQUENCE: 168
uuccauuggu acucgucuac u                                              21

<210> SEQ ID NO 169
<211> LENGTH: 21
<212> TYPE: DNA
<213> ORGANISM: Homo sapiens

<400> SEQUENCE: 169
gagtatggaa acgttaacca c                                              21

<210> SEQ ID NO 170
<211> LENGTH: 21
<212> TYPE: RNA
<213> ORGANISM: Homo sapiens

<400> SEQUENCE: 170
guauggaaac guuaaccacu u                                              21

<210> SEQ ID NO 171
<211> LENGTH: 21
<212> TYPE: RNA
<213> ORGANISM: Homo sapiens

<400> SEQUENCE: 171
uucauaccuu ugcaauuggu g                                              21

<210> SEQ ID NO 172
<211> LENGTH: 21
<212> TYPE: DNA
<213> ORGANISM: Homo sapiens

<400> SEQUENCE: 172
gaaacgttaa ccactggctg g                                              21

<210> SEQ ID NO 173
<211> LENGTH: 21
<212> TYPE: RNA
<213> ORGANISM: Homo sapiens

<400> SEQUENCE: 173
aacguuaacc acuggcuggu u                                              21

<210> SEQ ID NO 174
<211> LENGTH: 21
<212> TYPE: RNA
<213> ORGANISM: Homo sapiens

<400> SEQUENCE: 174
uuuugcaauu ggugaccgac c                                              21

<210> SEQ ID NO 175
<211> LENGTH: 21
<212> TYPE: DNA
<213> ORGANISM: Homo sapiens

<400> SEQUENCE: 175
gaatatgcgt tcgacaagcc g                                              21
```

<210> SEQ ID NO 176
<211> LENGTH: 21
<212> TYPE: RNA
<213> ORGANISM: Homo sapiens

<400> SEQUENCE: 176
auaugcguuc gacaagccgu u                                              21

<210> SEQ ID NO 177
<211> LENGTH: 21
<212> TYPE: RNA
<213> ORGANISM: Homo sapiens

<400> SEQUENCE: 177
uuuauacgca agcuguucgg c                                              21

<210> SEQ ID NO 178
<211> LENGTH: 21
<212> TYPE: DNA
<213> ORGANISM: Homo sapiens

<400> SEQUENCE: 178
gaaagacatg gtcatctgga a                                              21

<210> SEQ ID NO 179
<211> LENGTH: 21
<212> TYPE: RNA
<213> ORGANISM: Homo sapiens

<400> SEQUENCE: 179
aagacauggu caucuggaau u                                              21

<210> SEQ ID NO 180
<211> LENGTH: 21
<212> TYPE: RNA
<213> ORGANISM: Homo sapiens

<400> SEQUENCE: 180
uuuucuguac caguagaccu u                                              21

<210> SEQ ID NO 181
<211> LENGTH: 21
<212> TYPE: DNA
<213> ORGANISM: Homo sapiens

<400> SEQUENCE: 181
gacatggtca tctggaatcg t                                              21

<210> SEQ ID NO 182
<211> LENGTH: 21
<212> TYPE: RNA
<213> ORGANISM: Homo sapiens

<400> SEQUENCE: 182
cauggucauc uggaaucguu u                                              21

<210> SEQ ID NO 183
<211> LENGTH: 21
<212> TYPE: RNA
<213> ORGANISM: Homo sapiens

<400> SEQUENCE: 183
uuguaccagu agaccuuagc a            21

<210> SEQ ID NO 184
<211> LENGTH: 21
<212> TYPE: DNA
<213> ORGANISM: Homo sapiens

<400> SEQUENCE: 184
gatagctggt gctgatctgt t            21

<210> SEQ ID NO 185
<211> LENGTH: 21
<212> TYPE: RNA
<213> ORGANISM: Homo sapiens

<400> SEQUENCE: 185
uagcuggugc ugaucuguuu u            21

<210> SEQ ID NO 186
<211> LENGTH: 21
<212> TYPE: RNA
<213> ORGANISM: Homo sapiens

<400> SEQUENCE: 186
uuaucgacca cgacuagaca a            21

<210> SEQ ID NO 187
<211> LENGTH: 21
<212> TYPE: DNA
<213> ORGANISM: Homo sapiens

<400> SEQUENCE: 187
gatctgttta tcttcggcca c            21

<210> SEQ ID NO 188
<211> LENGTH: 21
<212> TYPE: RNA
<213> ORGANISM: Homo sapiens

<400> SEQUENCE: 188
ucuguuuauc uucggccacu u            21

<210> SEQ ID NO 189
<211> LENGTH: 21
<212> TYPE: RNA
<213> ORGANISM: Homo sapiens

<400> SEQUENCE: 189
uuagacaaau agaagccggu g            21

<210> SEQ ID NO 190
<211> LENGTH: 21
<212> TYPE: DNA
<213> ORGANISM: Homo sapiens

<400> SEQUENCE: 190
gaagtatgcc aaccagatgt a            21

<210> SEQ ID NO 191
<211> LENGTH: 21
<212> TYPE: RNA
<213> ORGANISM: Homo sapiens

<400> SEQUENCE: 191
aguaugccaa ccagauguau u                                    21

<210> SEQ ID NO 192
<211> LENGTH: 21
<212> TYPE: RNA
<213> ORGANISM: Homo sapiens

<400> SEQUENCE: 192
uuucauacgg uuggucuaca u                                    21

<210> SEQ ID NO 193
<211> LENGTH: 21
<212> TYPE: DNA
<213> ORGANISM: Homo sapiens

<400> SEQUENCE: 193
gatgtacatc gatactggtg c                                    21

<210> SEQ ID NO 194
<211> LENGTH: 21
<212> TYPE: RNA
<213> ORGANISM: Homo sapiens

<400> SEQUENCE: 194
uguacaucga uacuggugcu u                                    21

<210> SEQ ID NO 195
<211> LENGTH: 21
<212> TYPE: RNA
<213> ORGANISM: Homo sapiens

<400> SEQUENCE: 195
uuacauguag cuaugaccac g                                    21

<210> SEQ ID NO 196
<211> LENGTH: 21
<212> TYPE: DNA
<213> ORGANISM: Homo sapiens

<400> SEQUENCE: 196
gaaacctcac gctgtgcaaa g                                    21

<210> SEQ ID NO 197
<211> LENGTH: 21
<212> TYPE: RNA
<213> ORGANISM: Homo sapiens

<400> SEQUENCE: 197
aaccucacgc ugugcaaagu u                                    21

<210> SEQ ID NO 198
<211> LENGTH: 21
<212> TYPE: RNA
<213> ORGANISM: Homo sapiens

<400> SEQUENCE: 198
uuuuggagug cgacacguuu c                                    21

<210> SEQ ID NO 199
<211> LENGTH: 21
<212> TYPE: DNA
<213> ORGANISM: Homo sapiens

```
<400> SEQUENCE: 199
gaatacttcg tgccgaaatt c                                              21

<210> SEQ ID NO 200
<211> LENGTH: 21
<212> TYPE: RNA
<213> ORGANISM: Homo sapiens

<400> SEQUENCE: 200
auacuucgug ccgaaauucu u                                              21

<210> SEQ ID NO 201
<211> LENGTH: 21
<212> TYPE: RNA
<213> ORGANISM: Homo sapiens

<400> SEQUENCE: 201
uuuaugaagc acggcuuuaa g                                              21

<210> SEQ ID NO 202
<211> LENGTH: 21
<212> TYPE: DNA
<213> ORGANISM: Homo sapiens

<400> SEQUENCE: 202
gaaattccac gacatccgga t                                              21

<210> SEQ ID NO 203
<211> LENGTH: 21
<212> TYPE: RNA
<213> ORGANISM: Homo sapiens

<400> SEQUENCE: 203
aauuccacga cauccggauu u                                              21

<210> SEQ ID NO 204
<211> LENGTH: 21
<212> TYPE: RNA
<213> ORGANISM: Homo sapiens

<400> SEQUENCE: 204
uuuuaaggug cuguaggccu a                                              21

<210> SEQ ID NO 205
<211> LENGTH: 21
<212> TYPE: DNA
<213> ORGANISM: Homo sapiens

<400> SEQUENCE: 205
gaagaacgca agaaggacaa c                                              21

<210> SEQ ID NO 206
<211> LENGTH: 21
<212> TYPE: RNA
<213> ORGANISM: Homo sapiens

<400> SEQUENCE: 206
agaacgcaag aaggacaacu u                                              21

<210> SEQ ID NO 207
<211> LENGTH: 21
<212> TYPE: RNA
<213> ORGANISM: Homo sapiens
```

<400> SEQUENCE: 207 uucuugcgu ucuuccuguu g                              21

<210> SEQ ID NO 208
<211> LENGTH: 21
<212> TYPE: DNA
<213> ORGANISM: Homo sapiens

<400> SEQUENCE: 208
gaacgcaaga aggacaacgt g                             21

<210> SEQ ID NO 209
<211> LENGTH: 21
<212> TYPE: RNA
<213> ORGANISM: Homo sapiens

<400> SEQUENCE: 209
acgcaagaag gacaacgugu u                             21

<210> SEQ ID NO 210
<211> LENGTH: 21
<212> TYPE: RNA
<213> ORGANISM: Homo sapiens

<400> SEQUENCE: 210
uuugcguucu uccuguugca c                             21

<210> SEQ ID NO 211
<211> LENGTH: 21
<212> TYPE: DNA
<213> ORGANISM: Homo sapiens

<400> SEQUENCE: 211
gacggatact acaaggctca g                             21

<210> SEQ ID NO 212
<211> LENGTH: 21
<212> TYPE: RNA
<213> ORGANISM: Homo sapiens

<400> SEQUENCE: 212
cggauacuac aaggcucagu u                             21

<210> SEQ ID NO 213
<211> LENGTH: 21
<212> TYPE: RNA
<213> ORGANISM: Homo sapiens

<400> SEQUENCE: 213
uugccuauga uguccgagu c                              21

<210> SEQ ID NO 214
<211> LENGTH: 21
<212> TYPE: DNA
<213> ORGANISM: Homo sapiens

<400> SEQUENCE: 214
gatactacaa ggctcaggct c                             21

<210> SEQ ID NO 215
<211> LENGTH: 21
<212> TYPE: RNA

-continued

<213> ORGANISM: Homo sapiens

<400> SEQUENCE: 215
uacuacaagg cucaggcucu u                                     21

<210> SEQ ID NO 216
<211> LENGTH: 21
<212> TYPE: RNA
<213> ORGANISM: Homo sapiens

<400> SEQUENCE: 216
uuaugauguu ccgaguccga g                                     21

<210> SEQ ID NO 217
<211> LENGTH: 21
<212> TYPE: DNA
<213> ORGANISM: Homo sapiens

<400> SEQUENCE: 217
gaaagctttc aacgccttta t                                     21

<210> SEQ ID NO 218
<211> LENGTH: 21
<212> TYPE: RNA
<213> ORGANISM: Homo sapiens

<400> SEQUENCE: 218
aagcuuucaa cgccuuuauu u                                     21

<210> SEQ ID NO 219
<211> LENGTH: 21
<212> TYPE: RNA
<213> ORGANISM: Homo sapiens

<400> SEQUENCE: 219
uuuucgaaag uugcggaaau a                                     21

<210> SEQ ID NO 220
<211> LENGTH: 21
<212> TYPE: DNA
<213> ORGANISM: Homo sapiens

<400> SEQUENCE: 220
gatttgccat gcatcagctg c                                     21

<210> SEQ ID NO 221
<211> LENGTH: 21
<212> TYPE: RNA
<213> ORGANISM: Homo sapiens

<400> SEQUENCE: 221
uuugccaugc aucagcugcu u                                     21

<210> SEQ ID NO 222
<211> LENGTH: 21
<212> TYPE: RNA
<213> ORGANISM: Homo sapiens

<400> SEQUENCE: 222
uuaaacggua cguagucgac g                                     21

<210> SEQ ID NO 223
<211> LENGTH: 21

```
<212> TYPE: DNA
<213> ORGANISM: Homo sapiens

<400> SEQUENCE: 223
gattgcggcc atttcaagac a                                              21

<210> SEQ ID NO 224
<211> LENGTH: 21
<212> TYPE: RNA
<213> ORGANISM: Homo sapiens

<400> SEQUENCE: 224
uugcggccau uucaagacau u                                              21

<210> SEQ ID NO 225
<211> LENGTH: 21
<212> TYPE: RNA
<213> ORGANISM: Homo sapiens

<400> SEQUENCE: 225
uuaacgccgg uaaaguucug u                                              21

<210> SEQ ID NO 226
<211> LENGTH: 42
<212> TYPE: DNA
<213> ORGANISM: Homo sapiens

<400> SEQUENCE: 226
gaactgcgct ttgaagaacg cgaactgcgc tttgaagaac gc                       42

<210> SEQ ID NO 227
<211> LENGTH: 21
<212> TYPE: RNA
<213> ORGANISM: Homo sapiens

<400> SEQUENCE: 227
acugcgcuuu gaagaacgcu u                                              21

<210> SEQ ID NO 228
<211> LENGTH: 21
<212> TYPE: RNA
<213> ORGANISM: Homo sapiens

<400> SEQUENCE: 228
uuugacgcga aacuucuugc g                                              21

<210> SEQ ID NO 229
<211> LENGTH: 21
<212> TYPE: DNA
<213> ORGANISM: Homo sapiens

<400> SEQUENCE: 229
gatacgtcaa ctggctcaat g                                              21

<210> SEQ ID NO 230
<211> LENGTH: 21
<212> TYPE: RNA
<213> ORGANISM: Homo sapiens

<400> SEQUENCE: 230
uacgucaacu ggcucaaugu u                                              21

<210> SEQ ID NO 231
```

```
<211> LENGTH: 21
<212> TYPE: RNA
<213> ORGANISM: Homo sapiens

<400> SEQUENCE: 231
uuaugcaguu gaccgaguua c                                              21

<210> SEQ ID NO 232
<211> LENGTH: 21
<212> TYPE: DNA
<213> ORGANISM: Homo sapiens

<400> SEQUENCE: 232
tagactggct gacaaaggtt t                                              21

<210> SEQ ID NO 233
<211> LENGTH: 21
<212> TYPE: RNA
<213> ORGANISM: Homo sapiens

<400> SEQUENCE: 233
gacuggcuga caaagguuuu u                                              21

<210> SEQ ID NO 234
<211> LENGTH: 21
<212> TYPE: RNA
<213> ORGANISM: Homo sapiens

<400> SEQUENCE: 234
uucugaccga cuguuuccaa a                                              21

<210> SEQ ID NO 235
<211> LENGTH: 21
<212> TYPE: DNA
<213> ORGANISM: Homo sapiens

<400> SEQUENCE: 235
taaccatgag cagatgatga t                                              21

<210> SEQ ID NO 236
<211> LENGTH: 21
<212> TYPE: RNA
<213> ORGANISM: Homo sapiens

<400> SEQUENCE: 236
accaugagca gaugaugauu u                                              21

<210> SEQ ID NO 237
<211> LENGTH: 21
<212> TYPE: RNA
<213> ORGANISM: Homo sapiens

<400> SEQUENCE: 237
uuugguacuc gucuacuacu a                                              21

<210> SEQ ID NO 238
<211> LENGTH: 21
<212> TYPE: DNA
<213> ORGANISM: Homo sapiens

<400> SEQUENCE: 238
tatcggagta tggaaacgtt a                                              21
```

```
<210> SEQ ID NO 239
<211> LENGTH: 21
<212> TYPE: RNA
<213> ORGANISM: Homo sapiens

<400> SEQUENCE: 239
ucggaguaug gaaacguuau u                                              21

<210> SEQ ID NO 240
<211> LENGTH: 21
<212> TYPE: RNA
<213> ORGANISM: Homo sapiens

<400> SEQUENCE: 240
uuagccucau accuuugcaa u                                              21

<210> SEQ ID NO 241
<211> LENGTH: 21
<212> TYPE: DNA
<213> ORGANISM: Homo sapiens

<400> SEQUENCE: 241
tatggaaacg ttaaccactg g                                              21

<210> SEQ ID NO 242
<211> LENGTH: 21
<212> TYPE: RNA
<213> ORGANISM: Homo sapiens

<400> SEQUENCE: 242
uggaaacguu aaccacuggu u                                              21

<210> SEQ ID NO 243
<211> LENGTH: 21
<212> TYPE: RNA
<213> ORGANISM: Homo sapiens

<400> SEQUENCE: 243
uuaccuuugc aauuggugac c                                              21

<210> SEQ ID NO 244
<211> LENGTH: 21
<212> TYPE: DNA
<213> ORGANISM: Homo sapiens

<400> SEQUENCE: 244
taaggctctg gttcataaat c                                              21

<210> SEQ ID NO 245
<211> LENGTH: 21
<212> TYPE: RNA
<213> ORGANISM: Homo sapiens

<400> SEQUENCE: 245
aggcucuggu ucauaaaucu u                                              21

<210> SEQ ID NO 246
<211> LENGTH: 21
<212> TYPE: RNA
<213> ORGANISM: Homo sapiens

<400> SEQUENCE: 246
uuuccgagac caaguauuua g                                              21
```

```
<210> SEQ ID NO 247
<211> LENGTH: 21
<212> TYPE: DNA
<213> ORGANISM: Homo sapiens

<400> SEQUENCE: 247
taacgaatat gcgttcgaca a                                              21

<210> SEQ ID NO 248
<211> LENGTH: 21
<212> TYPE: RNA
<213> ORGANISM: Homo sapiens

<400> SEQUENCE: 248
acgaauaugc guucgacaau u                                              21

<210> SEQ ID NO 249
<211> LENGTH: 21
<212> TYPE: RNA
<213> ORGANISM: Homo sapiens

<400> SEQUENCE: 249
uuugcuuaua cgcaagcugu u                                              21

<210> SEQ ID NO 250
<211> LENGTH: 21
<212> TYPE: DNA
<213> ORGANISM: Homo sapiens

<400> SEQUENCE: 250
tagctggtgc tgatctgttt a                                              21

<210> SEQ ID NO 251
<211> LENGTH: 21
<212> TYPE: RNA
<213> ORGANISM: Homo sapiens

<400> SEQUENCE: 251
gcuggugcug aucuguuuau u                                              21

<210> SEQ ID NO 252
<211> LENGTH: 21
<212> TYPE: RNA
<213> ORGANISM: Homo sapiens

<400> SEQUENCE: 252
uucgaccacg acuagacaaa u                                              21

<210> SEQ ID NO 253
<211> LENGTH: 21
<212> TYPE: DNA
<213> ORGANISM: Homo sapiens

<400> SEQUENCE: 253
tatgccaacc agatgtacat c                                              21

<210> SEQ ID NO 254
<211> LENGTH: 21
<212> TYPE: RNA
<213> ORGANISM: Homo sapiens

<400> SEQUENCE: 254
ugccaaccag auguacaucu u                                              21
```

```
<210> SEQ ID NO 255
<211> LENGTH: 21
<212> TYPE: RNA
<213> ORGANISM: Homo sapiens

<400> SEQUENCE: 255
uuacgguugg ucuacaugua g                                      21

<210> SEQ ID NO 256
<211> LENGTH: 21
<212> TYPE: DNA
<213> ORGANISM: Homo sapiens

<400> SEQUENCE: 256
tatgcggtga atacttcgtg c                                      21

<210> SEQ ID NO 257
<211> LENGTH: 21
<212> TYPE: RNA
<213> ORGANISM: Homo sapiens

<400> SEQUENCE: 257
ugcggugaau acuucgugcu u                                      21

<210> SEQ ID NO 258
<211> LENGTH: 21
<212> TYPE: RNA
<213> ORGANISM: Homo sapiens

<400> SEQUENCE: 258
uuacgccacu uaugaagcac g                                      21

<210> SEQ ID NO 259
<211> LENGTH: 21
<212> TYPE: DNA
<213> ORGANISM: Homo sapiens

<400> SEQUENCE: 259
tacttcgtgc cgaaattcca c                                      21

<210> SEQ ID NO 260
<211> LENGTH: 21
<212> TYPE: RNA
<213> ORGANISM: Homo sapiens

<400> SEQUENCE: 260
cuucgugccg aaauuccacu u                                      21

<210> SEQ ID NO 261
<211> LENGTH: 21
<212> TYPE: RNA
<213> ORGANISM: Homo sapiens

<400> SEQUENCE: 261
uugaagcacg gcuuuaaggu g                                      21

<210> SEQ ID NO 262
<211> LENGTH: 21
<212> TYPE: DNA
<213> ORGANISM: Homo sapiens

<400> SEQUENCE: 262
```

-continued tacaaggctc aggctcagaa a                                              21

<210> SEQ ID NO 263
<211> LENGTH: 21
<212> TYPE: RNA
<213> ORGANISM: Homo sapiens

<400> SEQUENCE: 263
caaggcucag gcucagaaau u                                              21

<210> SEQ ID NO 264
<211> LENGTH: 21
<212> TYPE: RNA
<213> ORGANISM: Homo sapiens

<400> SEQUENCE: 264
uuguuccgag uccgagucuu u                                              21

<210> SEQ ID NO 265
<211> LENGTH: 21
<212> TYPE: DNA
<213> ORGANISM: Homo sapiens

<400> SEQUENCE: 265
taagcagtgc aaatcctgta a                                              21

<210> SEQ ID NO 266
<211> LENGTH: 21
<212> TYPE: RNA
<213> ORGANISM: Homo sapiens

<400> SEQUENCE: 266
agcagugcaa auccuguaau u                                              21

<210> SEQ ID NO 267
<211> LENGTH: 21
<212> TYPE: RNA
<213> ORGANISM: Homo sapiens

<400> SEQUENCE: 267
uuucgucacg uuuaggacau u                                              21

<210> SEQ ID NO 268
<211> LENGTH: 21
<212> TYPE: DNA
<213> ORGANISM: Homo sapiens

<400> SEQUENCE: 268
tacgtcaact ggctcaatgg t                                              21

<210> SEQ ID NO 269
<211> LENGTH: 21
<212> TYPE: RNA
<213> ORGANISM: Homo sapiens

<400> SEQUENCE: 269
cgucaacugg cucaaugguu u                                              21

<210> SEQ ID NO 270
<211> LENGTH: 21
<212> TYPE: RNA
<213> ORGANISM: Homo sapiens

<400> SEQUENCE: 270
uugcaguuga ccgaguuacc a                                    21

<210> SEQ ID NO 271
<211> LENGTH: 21
<212> TYPE: DNA
<213> ORGANISM: Homo sapiens

<400> SEQUENCE: 271
aagtatgcgg tgaatacttc g                                    21

<210> SEQ ID NO 272
<211> LENGTH: 21
<212> TYPE: RNA
<213> ORGANISM: Homo sapiens

<400> SEQUENCE: 272
guaugcggug aauacuucgu u                                    21

<210> SEQ ID NO 273
<211> LENGTH: 21
<212> TYPE: RNA
<213> ORGANISM: Homo sapiens

<400> SEQUENCE: 273
uucauacgcc acuuaugaag c                                    21

<210> SEQ ID NO 274
<211> LENGTH: 21
<212> TYPE: DNA
<213> ORGANISM: Homo sapiens

<400> SEQUENCE: 274
aatcctcgca atggaagaac g                                    21

<210> SEQ ID NO 275
<211> LENGTH: 21
<212> TYPE: RNA
<213> ORGANISM: Homo sapiens

<400> SEQUENCE: 275
uccucgcaau ggaagaacgu u                                    21

<210> SEQ ID NO 276
<211> LENGTH: 21
<212> TYPE: RNA
<213> ORGANISM: Homo sapiens

<400> SEQUENCE: 276
uuaggagcgu uaccuucuug c                                    21

<210> SEQ ID NO 277
<211> LENGTH: 21
<212> TYPE: DNA
<213> ORGANISM: Homo sapiens

<400> SEQUENCE: 277
aagaacgcaa gaaggacaac g                                    21

<210> SEQ ID NO 278
<211> LENGTH: 21
<212> TYPE: RNA
<213> ORGANISM: Homo sapiens

```
<400> SEQUENCE: 278
gaacgcaaga aggacaacgu u                                       21

<210> SEQ ID NO 279
<211> LENGTH: 21
<212> TYPE: RNA
<213> ORGANISM: Homo sapiens

<400> SEQUENCE: 279
uucuugcguu cuuccuguug c                                       21

<210> SEQ ID NO 280
<211> LENGTH: 21
<212> TYPE: DNA
<213> ORGANISM: Homo sapiens

<400> SEQUENCE: 280
caatcctcgc aatggaagaa c                                       21

<210> SEQ ID NO 281
<211> LENGTH: 21
<212> TYPE: RNA
<213> ORGANISM: Homo sapiens

<400> SEQUENCE: 281
auccucgcaa uggaagaacu u                                       21

<210> SEQ ID NO 282
<211> LENGTH: 21
<212> TYPE: RNA
<213> ORGANISM: Homo sapiens

<400> SEQUENCE: 282
uuuaggagcg uuaccuucuu g                                       21

<210> SEQ ID NO 283
<211> LENGTH: 21
<212> TYPE: DNA
<213> ORGANISM: Homo sapiens

<400> SEQUENCE: 283
caggccagac ggatactaca a                                       21

<210> SEQ ID NO 284
<211> LENGTH: 21
<212> TYPE: RNA
<213> ORGANISM: Homo sapiens

<400> SEQUENCE: 284
uuccggucug ccuaugaugu u                                       21

<210> SEQ ID NO 285
<211> LENGTH: 21
<212> TYPE: RNA
<213> ORGANISM: Homo sapiens

<400> SEQUENCE: 285
ggccagacgg auacuacaau u                                       21

<210> SEQ ID NO 286
<211> LENGTH: 21
<212> TYPE: DNA
<213> ORGANISM: Homo sapiens
```

```
<400> SEQUENCE: 286
cagacggata ctacaaggct c                                    21

<210> SEQ ID NO 287
<211> LENGTH: 21
<212> TYPE: RNA
<213> ORGANISM: Homo sapiens

<400> SEQUENCE: 287
gacggauacu acaaggcucu u                                    21

<210> SEQ ID NO 288
<211> LENGTH: 21
<212> TYPE: RNA
<213> ORGANISM: Homo sapiens

<400> SEQUENCE: 288
uucugccuau gauguuccga g                                    21

<210> SEQ ID NO 289
<211> LENGTH: 21
<212> TYPE: DNA
<213> ORGANISM: Homo sapiens

<400> SEQUENCE: 289
gaacgcaaga aggacaacgt g                                    21

<210> SEQ ID NO 290
<211> LENGTH: 21
<212> TYPE: RNA
<213> ORGANISM: Homo sapiens

<400> SEQUENCE: 290
acgcaagaag gacaacgugu u                                    21

<210> SEQ ID NO 291
<211> LENGTH: 21
<212> TYPE: RNA
<213> ORGANISM: Homo sapiens

<400> SEQUENCE: 291
uuugcguucu uccuguugca c                                    21

<210> SEQ ID NO 292
<211> LENGTH: 21
<212> TYPE: DNA
<213> ORGANISM: Homo sapiens

<400> SEQUENCE: 292
gacggatact acaaggctca g                                    21

<210> SEQ ID NO 293
<211> LENGTH: 21
<212> TYPE: RNA
<213> ORGANISM: Homo sapiens

<400> SEQUENCE: 293
cggauacuac aaggcucagu u                                    21

<210> SEQ ID NO 294
<211> LENGTH: 21
<212> TYPE: RNA
```

<213> ORGANISM: Homo sapiens

<400> SEQUENCE: 294
uugccuauga uguuccgagu c                                              21

<210> SEQ ID NO 295
<211> LENGTH: 21
<212> TYPE: DNA
<213> ORGANISM: Homo sapiens

<400> SEQUENCE: 295
gatacgtcaa ctggctcaat g                                              21

<210> SEQ ID NO 296
<211> LENGTH: 21
<212> TYPE: RNA
<213> ORGANISM: Homo sapiens

<400> SEQUENCE: 296
uacgucaacu ggcucaaugu u                                              21

<210> SEQ ID NO 297
<211> LENGTH: 21
<212> TYPE: RNA
<213> ORGANISM: Homo sapiens

<400> SEQUENCE: 297
uuaugcaguu gaccgaguua c                                              21

<210> SEQ ID NO 298
<211> LENGTH: 21
<212> TYPE: DNA
<213> ORGANISM: Homo sapiens

<400> SEQUENCE: 298
tatgcggtga atacttcgtg c                                              21

<210> SEQ ID NO 299
<211> LENGTH: 21
<212> TYPE: RNA
<213> ORGANISM: Homo sapiens

<400> SEQUENCE: 299
ugcggugaau acuucgugcu u                                              21

<210> SEQ ID NO 300
<211> LENGTH: 21
<212> TYPE: RNA
<213> ORGANISM: Homo sapiens

<400> SEQUENCE: 300
uuacgccacu uaugaagcac g                                              21

<210> SEQ ID NO 301
<211> LENGTH: 21
<212> TYPE: DNA
<213> ORGANISM: Homo sapiens

<400> SEQUENCE: 301
tacgtcaact ggctcaatgg t                                              21

<210> SEQ ID NO 302
<211> LENGTH: 21

-continued

```
<212> TYPE: RNA
<213> ORGANISM: Homo sapiens

<400> SEQUENCE: 302
cgucaacugg cucaaugguu u                                        21

<210> SEQ ID NO 303
<211> LENGTH: 21
<212> TYPE: RNA
<213> ORGANISM: Homo sapiens

<400> SEQUENCE: 303
uugcaguuga ccgaguuacc a                                        21
```

What is claimed is:

1. An isolated polypeptide comprising SEQ ID NO:2.

\* \* \* \* \*

UNITED STATES PATENT AND TRADEMARK OFFICE
CERTIFICATE OF CORRECTION

PATENT NO. : 7,208,306 B2  
APPLICATION NO. : 10/691529  
DATED : April 24, 2007  
INVENTOR(S) : Wei Liu et al.

Page 1 of 1

It is certified that error appears in the above-identified patent and that said Letters Patent is hereby corrected as shown below:

On the Title Page Item (75)  
Chalsea should be Chelsea

Column 45 - lines 1-4  
<160> should read:  
NUMBER OF SEQ ID NOS: 304

Column 127, after the nucleotide sequence for SEQ ID NO:303  
add  
<210> SEQ ID NO 304  
<211> LENGTH: 168  
<212> TYPE: PRT  
<213> ORGANISM: Homo sapiens  
<400> SEQUENCE: 304

```
Asp Leu Asp Glu Leu Leu Leu Leu Leu Leu Glu Leu Leu Gly Glu Pro
 1               5                  10                  15
Lys Pro Asp Leu Val Leu Phe Leu Gly Asp Leu Val Asp Arg Gly Pro
                20                  25                  30
Pro Ser Leu Glu Val Leu Leu Leu Leu Phe Ala Leu Lys Leu Lys Leu
            35                  40                  45
Pro Gly Pro Val Tyr Leu Val Arg Gly Asn His Asp Phe Asp Ser Gly
        50                  55                  60
Asn Ser Val Leu Gly Phe Leu Leu Glu Cys Ala Gly Phe Pro Tyr Val
65                  70                  75                  80
Leu Ala Asn Val Gly Asp Leu Val Glu Ile Val Gly Leu Ser Ser Leu
                85                  90                  95
Tyr Gly Lys Gly Gly Asn Val Trp Glu Leu Phe Leu Glu Leu Phe
                100                 105                 110
Asp Leu Leu Leu Leu Ala Ala Leu Val Asp Gly Lys Ile Leu Leu Val
            115                 120                 125
His Gly Pro Leu Ser Pro Asp Leu Asp Ser Gly Asp Asp Ile Val Leu
        130                 135                 140
Phe Gly Pro Glu Val Leu Glu Glu Leu Leu Lys Lys Asn Gly Val Asp
145                 150                 155                 160
Leu Val Leu Arg Gly His Thr His
                165
```

Signed and Sealed this

Thirtieth Day of March, 2010

David J. Kappos  
*Director of the United States Patent and Trademark Office*